US011648198B2

(12) United States Patent
Menachem et al.

(10) Patent No.: US 11,648,198 B2
(45) Date of Patent: *May 16, 2023

(54) EXPANDABLE GASTRORETENTIVE DOSAGE FORM

(71) Applicant: Clexio Biosciences Ltd., Jerusalem (IL)

(72) Inventors: Avshalom Ben Menachem, Zur Izhak (IL); Ilan Zalit, Rosh Ha'ayin (IL)

(73) Assignee: CLEXIO BIOSCIENCES LTD., Jerusalem (IL)

( * ) Notice: Subject to any disclaimer, the term of this patent is extended or adjusted under 35 U.S.C. 154(b) by 190 days.

This patent is subject to a terminal disclaimer.

(21) Appl. No.: 17/015,700

(22) Filed: Sep. 9, 2020

(65) Prior Publication Data

US 2020/0405635 A1  Dec. 31, 2020

Related U.S. Application Data

(63) Continuation of application No. 16/450,076, filed on Jun. 24, 2019, now Pat. No. 11,285,102, which is a continuation of application No. 14/728,986, filed on Jun. 2, 2015, now Pat. No. 10,485,758.

(60) Provisional application No. 62/093,763, filed on Dec. 18, 2014, provisional application No. 62/006,541, filed on Jun. 2, 2014.

(51) Int. Cl.
*A61K 9/00* (2006.01)
*A61K 9/20* (2006.01)
*A61M 31/00* (2006.01)

(52) U.S. Cl.
CPC .......... *A61K 9/0065* (2013.01); *A61K 9/2013* (2013.01); *A61K 9/2031* (2013.01); *A61K 9/2054* (2013.01); *A61K 9/2072* (2013.01); *A61M 31/002* (2013.01)

(58) Field of Classification Search
CPC .................................................... A61K 9/0065
See application file for complete search history.

(56) References Cited

U.S. PATENT DOCUMENTS

| 1,318,259 A | 10/1919 | Bohne |
| 3,844,285 A | 10/1974 | Laby |
| 4,220,153 A | 9/1980 | Dresback |
| (Continued) | | |

FOREIGN PATENT DOCUMENTS

| EP | 0202159 A2 | 11/1986 |
| EP | 0344939 A2 | 12/1989 |
| (Continued) | | |

OTHER PUBLICATIONS

Definition of "disengage". Accessed online on Nov. 16, 2020 at https://www.merriam-webster.com. (Year: 2020).*

(Continued)

*Primary Examiner* — Johann R Richter
*Assistant Examiner* — Casey S Hagopian
(74) *Attorney, Agent, or Firm* — Morgan, Lewis & Bockius LLP

(57) ABSTRACT

An oral gastro-retentive delivery device is provided which unfolds rapidly upon contact with gastric juice. The device is configured in a collapsed configuration for oral intake and unfolding for gastric retention for a predetermined period of time and eventually reducing in size for passage through the rest of the GI track.

15 Claims, 38 Drawing Sheets

(56) References Cited

U.S. PATENT DOCUMENTS

| | | | |
|---|---|---|---|
| 4,735,804 A * | 4/1988 | Caldwell | A61M 31/002 |
| | | | 424/452 |
| 4,767,627 A | 8/1988 | Caldwell et al. | |
| 5,002,772 A | 3/1991 | Curatolo et al. | |
| 5,443,843 A | 8/1995 | Curatolo et al. | |
| 5,780,057 A | 7/1998 | Conte et al. | |
| 6,488,962 B1 | 12/2002 | Berner et al. | |
| 6,685,962 B2 | 2/2004 | Friedman et al. | |
| 6,723,340 B2 | 4/2004 | Gusler et al. | |
| 6,753,011 B2 | 6/2004 | Faour | |
| 7,976,870 B2 | 7/2011 | Berner et al. | |
| 8,298,574 B2 | 10/2012 | Tsabari et al. | |
| 8,329,215 B2 | 12/2012 | Berner et al. | |
| 8,460,706 B2 | 6/2013 | Vergnault et al. | |
| 8,586,083 B2 | 11/2013 | Mohammad | |
| 8,609,136 B2 | 12/2013 | Tsabari et al. | |
| 8,753,678 B2 | 6/2014 | Tsabari et al. | |
| 10,485,758 B2 * | 11/2019 | Menachem | A61K 9/0065 |
| 11,147,766 B2 * | 10/2021 | Zalit | A61K 9/0065 |
| 2005/0202090 A1 | 9/2005 | Clarke | |
| 2008/0299197 A1 | 12/2008 | Toneguzzo et al. | |
| 2009/0324694 A1 | 12/2009 | Mohammad | |
| 2010/0112053 A1 | 5/2010 | Momose et al. | |
| 2011/0066175 A1 | 3/2011 | Gross | |
| 2011/0117190 A1 | 5/2011 | Brown et al. | |
| 2011/0117192 A1 | 5/2011 | Navon et al. | |
| 2011/0268666 A1 | 11/2011 | Friedman et al. | |
| 2011/0301129 A1 | 12/2011 | Berner et al. | |
| 2012/0021009 A1 | 1/2012 | Prinderre et al. | |
| 2012/0263792 A1 | 10/2012 | Lim et al. | |
| 2012/0321706 A1 | 12/2012 | Masri et al. | |
| 2013/0072869 A1 | 3/2013 | Cutchis et al. | |
| 2013/0164377 A1 | 6/2013 | Berner et al. | |
| 2013/0197441 A1 | 8/2013 | Tsabari et al. | |
| 2014/0017303 A1 | 1/2014 | Navon et al. | |
| 2014/0148840 A1 | 5/2014 | Mintchev et al. | |

FOREIGN PATENT DOCUMENTS

| | | |
|---|---|---|
| EP | 0415671 B1 | 3/1995 |
| GB | 1318259 A | 5/1973 |
| JP | 62-026215 A | 2/1987 |
| JP | 02-029268 A | 1/1990 |
| JP | 03-163011 | 7/1991 |
| WO | 2003/057197 A1 | 7/2003 |
| WO | 2006/072948 A2 | 7/2006 |
| WO | 2007/093999 A1 | 8/2007 |
| WO | 2007/106960 A1 | 9/2007 |
| WO | 2009/144558 A1 | 12/2009 |
| WO | 2010/035273 A2 | 4/2010 |
| WO | 2011/048494 A2 | 4/2011 |
| WO | 2011/090724 A3 | 11/2011 |
| WO | 2012/006961 A1 | 1/2012 |
| WO | 2012/006963 A1 | 1/2012 |
| WO | 2012/059815 A1 | 5/2012 |
| WO | 2013/054285 A1 | 4/2013 |
| WO | 2015/191920 A1 | 12/2015 |
| WO | 2015/191922 A1 | 12/2015 |

OTHER PUBLICATIONS

Definition of "detach". Accessed online on Nov. 16, 2020 at https://www.merriam-webster.com. (Year: 2020).*

Rowe et al., Handbook of Pharmaceutical Excipients, "Cellulose Acetate Phthalate", 6th ed., 2009, Pharmaceutical Press, pp. 191-193. (Year: 2009).*

Rowe et al., Handbook of Pharmaceutical Excipients, "Hypromellose Phthalate", 6th ed., 2009, Pharmaceutical Press, pp. 333-336. (Year: 2009).*

McLauchlan et al. "Comparison of gastric body and antral pH: a 24 hour ambulatory study in healthy volunteers" Gut, Oct. 1989, 30, pp. 573-578. (Year: 1989).*

Cardinal et al., "Gastric Retentive Drug Delivery Systems", Oral Bioavailability, 2011, 329-341.

Fix et al., "Controlled Gastric Emptying, III. Gastric Residence Time of a Nondisintegrating Geometric Shape in Human Volunteers", Pharmaceutical Research, 1993, 10, 7, 1087-1089.

International Preliminary Report on Patentability dated May 20, 2016 in Corresponding International Application No. PCT/US15/33850, 12 pages.

International Search Report dated Oct. 23, 2015 in corresponding International Application No. PCT/US15/33850.

Klausner et al., "Expandable Gastrorentetive Dosage Forms", Journal of Controlled Release, 2003, 90, 143-162.

Lopes et al., "Overview on Gastroretentive Drug Delivery Systems for Improving Drug Bioavailability", International Journal of Pharmaceutics, 2016, 144-158.

Sakshi, "Gastroretentive Drug Delivery Systems: An Overview", IPS, 2013, 37-45.

Shivram et al., "Gastro Rententive Drug Delivery System: A Review", IJPRAS, 2012, 1-13.

Tibbitt, "Emerging Frontiers in Drug Delivery", JACS, 2016, 138, 704-717.

Zema, L. et al., "Gastroresistant Capsular Device Prepared By Injection Molding," International Journal of Pharmaceuticals, Jan. 2013, pp. 264-272, vol. 440.

Zema, L. et al., "Injection Molding and its Application to Drug Delivery," Journal of Controlled Release, May 2012, pp. 324-331, vol. 159, Issue 3.

* cited by examiner

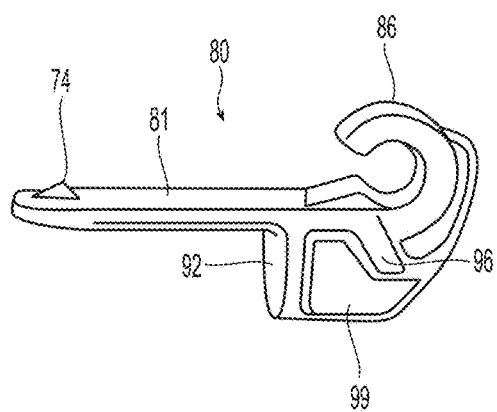
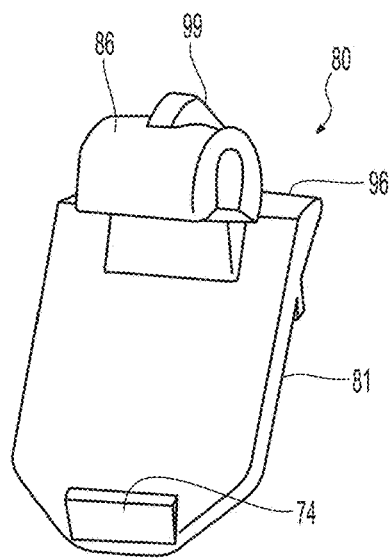
Fig. 24A
Fig. 24B
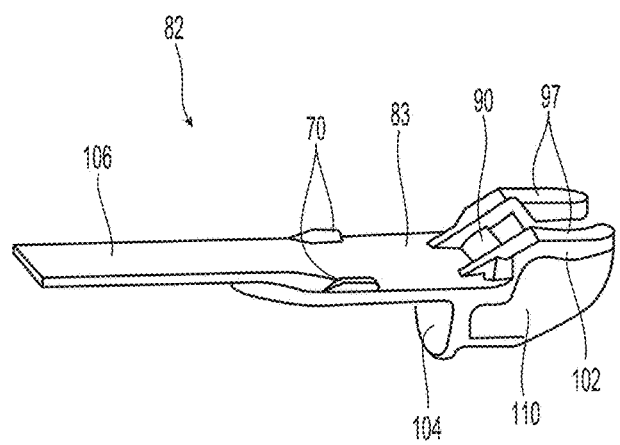
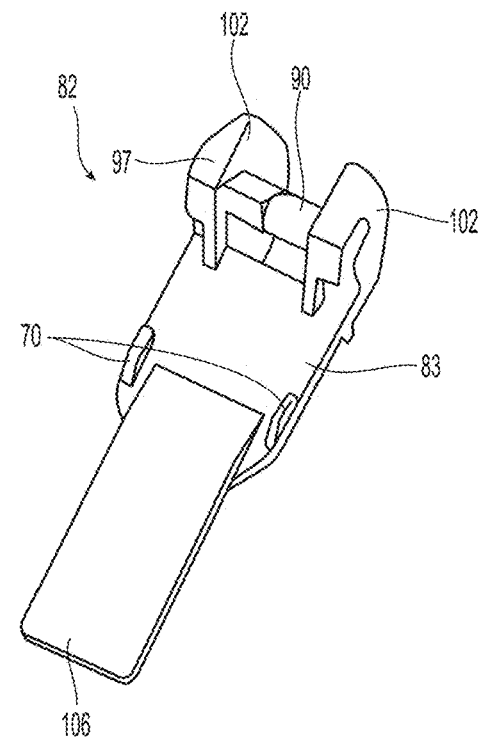
Fig. 25A
Fig. 25B

EXPANDABLE GASTRORETENTIVE DOSAGE FORM

CROSS REFERENCE TO RELATED APPLICATIONS

The present application is a continuation application of U.S. patent application Ser. No. 16/450,076, filed on Jun. 24, 2019, which is a continuation application of U.S. patent application Ser. No. 14/728,986, filed on Jun. 2, 2015, now U.S. Pat. No. 10,485,758, which claims the benefit of and priority to U.S. Provisional Application Ser. No. 62/006,541, filed on Jun. 2, 2014 and U.S. Provisional Application Ser. No. 62/093,763, filed on Dec. 18, 2014, the entire contents of which are incorporated herein by reference.

FIELD OF THE DISCLOSURE

The present disclosure relates to a pharmaceutical product. More particularly, the present disclosure relates to an oral pharmaceutical or gastric retentive dosage form and formulations relating thereto.

BACKGROUND

There has been extensive research in the area of gastric retentive drug delivery systems and dosage forms. These systems and dosage forms are particularly useful for the delivery of drugs that:

(1) have a "narrow absorption window" in the gastrointestinal tract, for example, drugs that are preferentially absorbed in the duodenum and/or jejunum over ileum and/or colon, or have better solubility in upper parts of the gastrointestinal tract (GI);

(2) are intended for local treatment of proximal parts of the gastrointestinal tract (stomach and/or duodenum); and/or (3) degrade in the colon or in the intestines, etc.

Gastric retentive drug delivery systems or dosage forms have focused research in three areas of technology: namely, floating systems; systems with expanding geometry through swelling or unfolding; and bioadhesive systems.

The general concept of the expandable gastroretentive systems and dosage forms is that the system or dosage form starts in a condition or configuration suitable for swallowing. The system or dosage form then expands in the stomach to prevent gastric emptying. Eventually, the system or dosage form reduces in size to pass through the pylorus or disintegrates. Some of the original formulations with this approach are known from the veterinary world. For example, U.S. Pat. No. 3,844,285 discloses the concept of a pill that can be swallowed with wings taped down that eventually expand once water-degradable tape disintegrates. Such veterinary gastroretentive devices and formulations are sold under the tradenames Captec® and Ivomec® SR Bolus. In the area of commercialized animal products, Paratect Flex® bolus is a trilaminate sheet with a central polymeric matrix and drug load which is rolled up and held by a piece of water-soluble adhesive tape in the form of a cylindrical pill.

In the area of human oral application, U.S. Pat. No. 5,002,772 discloses a device with a plurality of compressible retention arms attached to a controlled release device which, in the expanded configuration, resists gastrointestinal transit. U.S. Pat. Nos. 4,735,804 and 4,767,627 disclose a series of substantially planar geometric shapes, e.g., a tetrahedron formed of a bioerodible polymer that may be compressed and collapsed for oral administration. U.S. Pat. No. 8,298,574 discloses an "Accordion pill", a sheet with a length of more than 20 mm, folded like an accordion and placed in a capsule.

There have been many challenges in designing gastric retentive dosage forms relating to ability to scale up/manufacture/assemble, drug loading capacity, retention during fasted state, the inclusion of an emergency release mechanism to expel the delivery system or dosage form in an emergency situation, using pharmaceutically acceptable ingredients etc. Improvements concerning any one of these challenges would provide a significant contribution to the area of gastric retentive drug delivery systems and dosage forms.

SUMMARY OF THE DISCLOSURE

Improvements concerning any one of these challenges and needs would provide a significant contribution to the area of gastric retentive drug delivery systems and dosage forms. The present disclosure relates to a gastroretentive dosage form (GRDF) that includes one or more of the following characteristics:

Rapidly unfolds within less than 3 min. to maximum gastric retentive size;

Maintains a sufficient size integrity and rigidity throughout the time period under gastric physiology or conditions; and/or Delays gastric emptying for a specific time dependent on the extent of API According to an aspect of the present disclosure a gastroretentive dosage form (GRDF) for extended retention in a stomach is provided which includes: a body configured to transform between a collapsed configuration for ingestion, an expanded configuration for retention within the stomach and a third configuration wherein after a predetermined time period has elapsed, the GRDF disassembles into two or more parts such that each of the disassembled parts of the GRDF is sized for exiting the stomach; and an active pharmaceutical ingredient (API) or diagnostic. In aspects, the third configuration is induced by at least a partial release of the API or diagnostic or compositions thereof.

In any of the aspects described herein, the body is configured to transform between a collapsed configuration for ingestion and an expanded configuration suitable for gastric retention within less than 5 minutes, in aspects, less than 4 minutes, in aspects, less than 3 minutes. In aspects described herein, a method is provided for gastric retention wherein a GRDF transforms to an expanded configuration for gastric retention within less than 5 minutes, in aspects, less than 4 minutes, in aspects, less than 3 minutes. Once the capsule at least partially dissolves, the body automatically transitions to the expanded configuration.

In any of the aspects, after a pre-determined period of time, the GRDFs described herein will eventually lose their mechanical integrity as a single unit, disassemble and pass from the stomach for subsequent evacuation. There are many possible mechanisms to achieve this result, all of which are encompassed by the present disclosure.

In any of the aspects described herein, the predetermined period of time is more than about 4 hours, in aspects, more than about 6 hours, in aspects, more than about 7 hours, in aspects more than 12 hours, in aspects more than 24 hs.

In any of the aspects described herein, transforming to the third configuration occurs when more than 70% of the active pharmaceutical ingredient is released, in aspects, when more than 75% of the active pharmaceutical ingredient is released, in aspects, when more than 80% of the active pharmaceutical ingredient is released, in aspects, when more than 85% of the active pharmaceutical ingredient is released, in aspects, when more than 90% of the active pharmaceutical ingredient is released, in aspects, when more than 95% of the active pharmaceutical ingredient is released, in aspects, when 100% of the active pharmaceutical ingredient is released.

It should be understood that any method or mechanism that is configured to transition or open the GRDF to the expanded configuration is encompassed by the present disclosure.

In one aspect, a superporous hydrogel system may be incorporated into the inner part of the arms which expands upon exposure to the gastric environment thereby forcing the two arms apart and to the expanded configuration. In another aspect, a leaf spring (similar to those described above) springs outwards and extends from the inner area of one or both of the arms once the expanding configuration is initiated or once the mechanical integrity of the collapsed condition has been compromised, e.g., capsule is dissolved. In other aspects, various mechanisms may be employed to lock the arms in an expanded configuration until the insert has sufficiently erodes to disassemble the GRDF.

For example, in any of the aspects described herein, an inner facing surface of one of the arms may include a locking mechanism to lock the leaf spring in place in the expanded configuration. Alternatively and in addition to the hinge assemblies described above, the hinge assembly may include one or more mechanical interfaces or mechanisms, gear, spring, cam, etc. that are configured to maintain or lock the GRDF in an expanded configuration until disassembly. In aspects, the leaf spring may simply be configured to bias the GRDF from the collapsed configuration and not necessarily lock to maintain the GRDF in the expanded configuration but may be configured to simply prevent the GRDF from transitioning back to the collapsed configuration.

In any of the aspects described herein, the leaf spring or biasing mechanism may be configured to lock the two arms in the expanded configuration until disassembly. One or more locking mechanisms may be employed for this purpose, or, alternatively, the leaf spring may be configured to engage one of the arms to keep the two arms apart until disassembly. In other aspects, the biasing mechanism, e.g., leaf spring, may be configured to engage the opposing arm to keep the two arms and separated as the insert slowly erodes. As the insert erodes (API is released), the bias of the leaf spring gradually lessens or the leaf spring regresses into the arm such that the angle β between the two arms and lessens to a point when the size or formation (e.g., triangular shape) of the GRDF is small enough to pass through the pyloric valve in the stomach. As can be appreciated, in this instance the GRDF does not necessarily need to disassembly for it to safely pass through the pyloric valve.

In any of the aspects described herein, the GRDF further comprises a biasing element configured to maintain the two arms apart once the two arms transition to the expanded configuration. In aspects, the biasing element is configured to transition the two arms from the collapsed configuration.

In aspects according to the present disclosure, the body may include at least two arms, or in other aspects, two arms. In any of the aspects described herein, two arms are capable of providing a size relevant for gastric retention. In any of the aspects described herein, the GRDF further comprises a biasing element configured to maintain the two arms apart once the two arms transition to the expanded configuration. In aspects, the biasing element is configured to transition the two arms from the collapsed configuration. Once in expanded position, the length between the tips of two arms is about 26-30 mm in length.

In aspects described herein, the biasing element forms part of the hinge assembly.

In any of the aspects described herein a size of at least one of the two arms is substantially maintained during transition between configurations. For example, even after 24 hr exposure to simulated gastric fluids—there is less than 10% preferably less than 5% change in weight, length and thickness of each arm, hinge etc.

In any of the aspects described herein, one of the at least two arms includes a cavity defined therein configured to engage the hinge assembly and the API or diagnostic or composition thereof. In any of the aspects described herein, at least a portion of the hinge assembly, may be sandwiched between at least one of the at least two arms of the body and the API or diagnostic or composition thereof hold one and other in place. Thus, any erosion or partial release of any of the API or API composition, the hinge assembly, arm or diagnostic will result in release from expanded state or end of gastric retention. For example, the hinge assembly, may be configured to disengage from the at least one arm upon partial release of the API. In another example, the hinge, API or arm may be coated or partially comprise a pH or temperature sensitive polymer which may be caused to erode via change in environment.

In any of the aspects described herein, in the expanded configuration, the at least two arms define an interior angle between about 45 degrees and about 90 degrees, in aspects, the at least two arms define an interior angle between about 45 degrees and about 80 degrees. In any of the aspects described herein, in the expanded configuration, the at least two arms define an interior angle of less than about 90° therebetween.

In any of the aspects described herein, at least one of the at least two arms may be configured to releasably engage the API or diagnostic. In any of the aspects described herein, the API or diagnostic is positioned within a cavity defined in the body. In any of the aspects described herein, the API may be positioned within the cavity in the form of a composition. The cavity may be formed for example, using injection molding, 3D printing, etc. In any of the aspects described herein, the at least two arms may be pivotably connected together or in articulated relationship by a hinge assembly and may be configured to disengage from one another due to partial degradation of at least one of the at least two arms or hinge assembly or partial release of the API or diagnostic. The partial degradation of at least one of the at least two arms or hinge assembly or partial release the API or diagnostic may be due to a pH dependent polymer. In any of the aspects described herein, the pH dependent polymer may be configured to erode in a basic environment.

In any of the aspects described herein, the API or diagnostic is encased or positioned within a cavity within the at least one of the at least two arms.

In any of the aspects described herein, the API or diagnostic is released via an opening defined within at least one of the two arms.

In any of the aspects described herein, the API or diagnostic is in the form of an insert tablet shaped to fit within a cavity defined in at least one of the at least two arms.

In any of the aspects described herein, the GRDFs are designed to maximize the volume and/or weight ratio of API to total excipients, in an effort to maximize the drug volume and/or weight load to be processed in the stomach while minimizing the volume of non-drug material that must pass through the gastrointestinal tract although any relevant amount of API is encompassed by the present disclosure. According to one aspect of the disclosure, a ratio of the weight of the active pharmaceutical ingredients to the weight of total excipients is from about 0.8 to about 0.05, in embodiments, from about 0.7 to about 0.3, and in other embodiment, from about 0.6 to about 0.4 or 0.5 to about 0.95. According to one aspect of the disclosure, a ratio of the weight of excipient to the weight of the API or the diagnostic is from about 0.8 to about 0.05, in embodiments, from about 0.7 to about 0.3, and in other embodiment, from about 0.6 to about 0.4. The total excipients may include the arms, the hinge, the excipients in the insert, and the capsule. In embodiments, the load of the excipients may be from about 500 mg to about 2000 mg. In any of the aspects described herein, the amount of API present in the insert may be an amount greater than 400 mg, 600 mg, 800 mg, 1000 mg, or 1500 mg. Alternatively, in aspects, the API drug load is about 400 milligrams to about 1.5 grams, in aspects, the API drug load is about 0.1 mg to about 2 grams or 10 mg to about 1.8 grams or 500 milligrams to about 1.5 grams. In aspects, the API drug load is about 600 milligrams to about 1.5 grams. The amount of API may depend on a variety of factors such as the need for additional excipients and the size of tablet. In aspects, the amount of API in the GRDF is a therapeutically effective amount for treating a particular disease or condition over a prescribed time period, e.g., hourly (q1h), q2h-q8h, b.d.s., and o.d.

In any of the aspects described herein, the body may include at least two arms.

In any of the aspects described herein, the at least two arms may be pivotably connected to one another about a hinge assembly.

In any of the aspects described herein, at least one of the at least two arms comprises a cavity defined therein configured to receive at least a first portion of the API or diagnostic. In aspects, the cavity includes a volume ranging from about 100 mm$^3$ to about 2000 mm$^3$ or from about 200 mm$^3$ to about 1800 mm$^3$. In aspects, the volume of the body may range from about 500 mm$^3$ to about 1500 mm$^3$. In embodiments, the volume of the body may range from about 800 mm$^3$ to about 1200 mm$^3$. In aspects, the volume of the body may be about 950 mm$^3$. In aspects, the at least one arm that includes the cavity includes an opening defined therein which may be in communication with the gastric environment. This hole would be distally located from the hinge assembly.

In any of the aspects described herein, at least one of the at least two arms may be configured to releasably engage the API or diagnostic. In any of the aspects described herein, the API or diagnostic is positioned within a cavity defined in the body. In any of the aspects described herein, the API may be positioned within the cavity in the form of a composition. In any of the aspects described herein the API positioned in the cavity is released at a controlled rate over more than 6 hours, in aspects, over more than 8 hours, in aspects, over more than 10 hours.

In aspects according to the present disclosure, the body may include two arms.

In any of the aspects described herein, the body comprising the at least one arm, hinge and cavity may be is produced by for example, using injection molding, 3D printing, etc. In any of the aspects described herein, the body injection molding or 3D printing. In any of the aspects described herein, the biasing element, the at least one of the at least two arms, and hinge assembly is manufactured from pharmaceutically acceptable excipients as listed in IIG guidelines.

In any of the aspects described herein, the body is maintained in the collapsed configuration by a retention mechanism and the body is transitioned to the expanded configuration by a hinge assembly. It should be understood that any retention method or mechanism that is configured to maintain the collapsed configuration of the GRDF prior to swallowing is envisioned. Several different aspects have been described herein and include a capsule that erodes or dissolves upon contact with gastric fluid. In another aspects, in a case where the natural state of the GRDF is open (natural or biased configuration of one of the hinge assemblies described herein is open to expand the GRDF), there may be a material holding the GRDF closed which dissolves or erodes in the presence of gastric fluid thereby releasing the GRDF to an expanded configuration. In other aspects, the material may be in the shape of an erodible band which encompasses the arms to maintain the GRDF in a collapsed configuration until the band erodes allowing expansion of the GRDF. Still other aspects include a glue-like material that keeps the two arms together until the glue-like material erodes allowing expansion of the GRDF. In another aspect, the retention mechanism may be a capsule which maintains the closed state and dissolves when introduced to a fluid environment, may be the capsule itself In any of the aspects described herein, the oral pharmaceutical further comprises a capsule configured to encompass the body when disposed in the collapsed configuration, the capsule configured to at least partially dissolve upon introduction to fluid to expose and release the body from the collapsed configuration.

In any of the aspects described herein, the GRDF maintains a shelf life durability or shelf life stability for more than 2 years under accelerated conditions.

In any of the aspects described herein, each arm may include a cavity defined therein configured to receive an API or diagnostic.

In any of the aspects described herein, the at least two arms are movable or pivotable about a hinge assembly.

In aspects, the at least two arms and the hinge assembly are releasable engaged to one another.

In any of the aspects described herein, the at least two arms detach from the hinge assembly at the predetermined period of time.

In any of the aspects described herein, the at least two arms detach from the hinge assembly when the API or diagnostic has been substantially released.

In any of the aspects described herein, the at least two arms include a first arm comprising a first API or diagnostic and a second arm comprising a second API or diagnostic. In aspects, the second API or diagnostic is incompatible with the first API or diagnostic.

In any of the aspects described herein, the at least two arms of the body are configured to disengage from one another upon partial release of the API. In any of the aspects described herein, the predetermined time period is at least 4 hours, in aspects, at least 6 hours, in aspects, at least 8 hours, in aspects, at least 10 hours, in aspects, at least 12 hours, in aspects, at least 18 hours. In any of the aspects described herein, the predetermined time period is in mammals such as dog or pig and preferably human.

In any of the aspects described herein, the size of each of individual arms and hinge is substantially maintained during transition between configurations. In aspects, there is less than 10%, in aspects, less than 5% change in size of each of the parts which make up the body, i.e., the hinge, arms etc. In aspects, this is so after exposure to 24 hrs simulated gastric conditions. In any of the aspects described herein, the size of at least one of the at least two arms is substantially maintained during transition between the first and second and then the second and third configurations.

In any of the aspects described herein, the hinge assembly may be made from one or more pharmaceutically acceptable ingredients. In any of the aspects described herein, the hinge assembly can include two interconnected hinge portions that are pivotably coupled to each other, each hinge portion being connected to one of the at least two arms. In aspects, each hinge portion is connected to one of the at least two arms by a mechanically engaging component such as the inner wall of the cavity in the arm. In aspects, the hinge assembly or portions are configured to rotate with respect to each other within a limited range of motion that is less than or equal to 90 degrees. In any of the aspects described herein, the hinge assembly is a unitary component.

In any of the aspects described herein, after the predetermined time period has lapsed, the hinge assembly is configured to disengage from the at least two arms for release from the stomach. In any of the aspects described herein, the hinge assembly can disengage from the at least two arms once the API is substantially released or the API composition is substantially eroded. Substantially released or eroded may be more than 70%, more than 75% or more than 80%. In aspects, the hinge assemblies or other connection mechanisms composed of one or more base-sensitive materials can begin to disintegrate or erode once exposed to the proximal end of the arm's internal matrix (the API release system or API composition) which includes basic material. In other aspects, the hinge assemblies or other connection mechanisms composed of one or more time sensitive polymers can begin to disintegrate at a certain point in time. In yet other aspects, the hinge assemblies or other connection mechanisms are connected to the arms in a certain mechanical fashion, with a certain mechanical shape or by one or more mechanical features such that once the arms, insert tablet or hinge assembly erode via the introduction of gastric fluids, the mechanical integrity of the hinge assembly or arms (or parts thereof) is compromised due to a change of shape of one or more mechanical elements and, as a result, the mechanical engagement is lost.

In any of the aspects described herein, the hinge assembly may be environment-sensitive, for example pH sensitive or preferably base sensitive, and is configured to deteriorate prior to expiration of the predetermined period of time once the hinge assembly is exposed to a basic solution.

In any of the aspects described herein, at least a portion of the hinge assembly is manufactured using injection molded materials.

In aspects, the partial degradation of at least one of the at least two arms or hinge assembly or partial release the API or diagnostic may be due to a pH dependent polymer. In any of the aspects described herein, the pH dependent polymer may be configured to erode in a basic environment. In another aspect, a method is provided for ending gastric retention of the GRDF by inducing a change in a basic environment. In any of the aspects described herein, as long as the hinge assembly engagement with the arms is environment sensitive, and the environment changes or can be induced to change, one can induce an end to gastric retention. In aspects, the pH dependent polymer may be coating or involved in physical make up of an arm or hinge assembly.

In any of the aspects described herein, the body is produced by injection molding or 3D printing.

According to an aspect of the present disclosure, a gastroretentive dosage form (GRDF) for extended retention in a stomach is provided and includes: a body including a hinge assembly, the body configured to move between a collapsed configuration for ingestion to an expanded configuration for retention in the stomach; and at least one insert retained within a portion of the body and comprising an active pharmaceutical ingredient (API) and an excipient, wherein a ratio of the API to a total load of the both the API and the excipient is from about 0.5 to about 0.95.

In any of the aspects described herein, the insert includes excipients for immediate release. According to another aspect of the disclosure, the ratio of the weight of the active pharmaceutical ingredients to the weight of the total weight of the insert tablet in the insert is from about 0.1 to about 0.99, in aspects, from about 0.5 to about 0.95, and in other aspects, from about 0.7 to about 0.9.

According to an aspect of the present disclosure, a pharmaceutical formulation suitable for retention in the stomach is provided and includes: a cellulose ester and a plasticizer combined in a ratio ranging from about 3:1 to about 8:1, wherein the pharmaceutical formulation is retained in the stomach for a time period of more than 4 hours.

In any of the aspects described herein, the pharmaceutical formulation is retained in the stomach for a time period of more than 6 hours, in aspects, for a time period of more than 8 hours, in aspects, for a time period of more than 12 hours, in aspects, for a time period of more than 18 hours, in aspects, for a time period of more than 24 hours, in aspects, for a time period of more than 36 hours. In any aspect, the period of time is under fasted conditions or after a light meal.

In any of the aspects described herein, the GRDF is folded and positioned in a capsule. In any of the aspects described herein the formulation further comprises retention arms or a hinge assembly.

According to an aspect of the present disclosure, a gastroretentive dosage form (GRDF) is provided that includes: a pharmaceutically acceptable material folded inside a capsule, wherein the pharmaceutical acceptable material unfolds into a size suitable for gastric retention in a time period of less than 5 minutes. In aspects, the time period for unfolding of the pharmaceutically acceptable material into a size suitable for gastric retention is less than 4 minutes, in aspects, less than 3 minutes, in aspects, less than 2 minutes.

In any of the aspects described herein, the GRDF further comprises an active pharmaceutical ingredient According to an aspect of the present disclosure, a gastroretentive dosage form (GRDF) is provided that includes: a pharmaceutically acceptable material folded inside a capsule and including an active pharmaceutical ingredient, wherein an end to gastric retention of the dosage form is controlled by a release of the active pharmaceutical ingredient.

In any of the aspects described herein, the end to gastric retention occurs when more than 70% of the active pharmaceutical ingredient is released, in aspects, when more than 75% of the active pharmaceutical ingredient is released, in aspects, when more than 80% of the active pharmaceutical ingredient is released, in aspects, when more than 85% of the active pharmaceutical ingredient is released, in aspects, when more than 90% of the active pharmaceutical ingredient is released, in aspects, when more than 95% of the active pharmaceutical ingredient is released, in aspects, when 100% of the active pharmaceutical ingredient is released.

According to an aspect of the present disclosure, a gastroretentive dosage form (GRDF) is provided that includes: a body including two arms transitionable between a collapsed configuration and an expanded configuration for retaining the GRDF within the stomach for a predetermined time period; and an active pharmaceutical ingredient (API) or diagnostic at least partially positioned within the body.

In any of the aspects described herein, a biasing element is configured to maintain the two arms apart once the two arms transition to the expanded configuration. In aspects, the biasing element is configured to transition the two arms from the collapsed configuration.

According to an aspect of the present disclosure, a gastroretentive dosage form (GRDF) is provided that includes a body including two arms transitionable from a first configuration swallowable by a user, a second configuration for retaining the GRDF within the stomach for a predetermined period of time, and a third configuration wherein the two arms disassemble after the elapse of the predetermined period of time.

According to an aspect of the present disclosure, a gastroretentive dosage form (GRDF) is provided that includes: at least two arms pivotably connected together and transitionable between a collapsed configuration wherein the at least two arms are disposed in close proximity relative to one another and the GRDF is suitable for swallowing and an expanded configuration wherein the at least two arms are further apart from one another; an active pharmaceutical ingredient (API) or diagnostic at least partially contained within a cavity defined in at least one of the at least two arms; and a biasing element configured to maintain the at least two arms apart once the at least two arms transition to the expanded configuration.

In any of the aspects described herein, the at least two arms are pivotable about a hinge assembly. In aspects described herein, the biasing element forms part of the hinge assembly. In aspects, the at least two arms and the hinge assembly are releasable engaged to one another.

In any of the aspects described herein, the hinge assembly is a unitary component.

In any of the aspects described herein, the hinge assembly includes two interconnected hinge portions that are pivotably coupled to each other, each hinge portion being connected to one of the at least two arms. In aspects, each hinge portion is connected to one of the at least two arms by a mechanically engaging component. In aspects, the hinge portions are configured to rotate with respect to each other within a limited range of motion that is less than or equal to 90 degrees.

According to an aspect of the present disclosure, a gastroretentive dosage form (GRDF) is provided that includes: a body including at least two arms each having a predetermined length and configured to move between a collapsed configuration for ingestion to an expanded configuration for retention in the stomach; and an active pharmaceutical ingredient positioned within at least one of the two arms, wherein the predetermined length of the at least one arm including the active pharmaceutical ingredient remains substantially the same during the release of the active pharmaceutical ingredient.

According to an aspect of the present disclosure, a gastroretentive dosage form (GRDF) is provided that includes: a body including at least two arms each having a predetermined length and configured to move between a collapsed configuration for ingestion to an expanded configuration for retention in the stomach; and an active pharmaceutical ingredient positioned within at least one of the two arms, wherein the predetermined length of at least one of the two arms remains substantially the same following disassembly of the body According to an aspect of the present disclosure, an oral pharmaceutical for extended retention in a stomach is provided that includes: a body configured to transform about a hinge assembly between a collapsed configuration for ingestion and an expanded configuration for retention within the stomach for a predetermined time period; and an active pharmaceutical ingredient (API) or diagnostic at least partially positioned within the body.

In any of the aspects described herein, another portion of the API or diagnostic is concealed by the at least one arm of the body.

According to an aspect of the present disclosure, a gastroretentive dosage form (GRDF) is provided that includes: a body comprising a pH sensitive material and including at least two arms configured to transform from a collapsed configuration for ingestion to an expanded configuration for retention in the stomach, wherein the pH sensitive material is configured to force the disassembly of the body.

According to an aspect of the present disclosure, a gastroretentive dosage form (GRDF) for extended retention in a stomach is provided that includes: a body configured to transform between a collapsed configuration for ingestion and an expanded configuration for retention within the stomach for a predetermined time period; and an active pharmaceutical ingredient (API) or diagnostic configured to releasably engage the body, wherein the body is configured to disassemble upon partial disintegration of the API, and wherein the body is made from a pharmaceutically acceptable material wherein the size, shape and durability of the body is substantially maintained while in the stomach for the predetermined period of time.

In any of the aspects described herein the API is released at a controlled rate over more than 6 hours, in aspects, over more than 8 hours, in aspects, over more than 10 hours In any of the aspects described herein, the API or diagnostic is encased by at least one of the at least two arms.

In any of the aspects described herein, the API or diagnostic is released via an opening defined within at least one of the two arms.

In any of the aspects described herein, the API or diagnostic is an insert shaped to fit within a cavity defined in at least one of the at least two arms.

In any of the aspects described herein, the insert includes excipients for immediate release.

In any of the aspects described herein, in the expanded configuration, the at least two arms define an interior angle of less than about 90° therebetween.

In any of the aspects described herein, the hinge assembly is pH sensitive and is configured to deteriorate prior to expiration of the predetermined period of time once the hinge assembly is exposed to a basic solution.

In any of the aspects described herein, in the expanded configuration, the at least two arms define an interior angle between about 45 degrees and about 90 degrees, in aspects, the at least two arms define an interior angle between about 45 degrees and about 80 degrees.

According to an aspect of the present disclosure, a gastroretentive dosage form (GRDF) is provided that includes: a body including at least two arms, the body configured to transform between a collapsed configuration for ingestion and an expanded configuration for retention within the stomach for a predetermined time period, wherein the gastroretentive dosage form maintains a mechanical strength and dimensions such that:

a. after 12 hr exposure to simulated gastric fluids [Rotating apparatus having 37° C., pH2+Xanthan gum 0.125 gr/L, 25 RPM mixing]—less than 5%, preferably less than 3% decrease in size when placed in a compression modulus with repeated force applied in the direction of refolding of 150 g/mm, up to 750 g b. after more than 8 hr exposure to simulated gastric fluids [Rotating apparatus having 37° C., pH2 Xanthan gum 0.125 gr/L, 25 RPM mixing]—size maintained to prevent passage through the 18 mm pipe test under 600 gr/F c. after more than 24 hrs in a pig stomach—size maintained d. after more than 24 hrs in a beagle dog stomach, 50% of the GRDFs maintained size e. after 24 hr exposure to simulated gastric fluids—less than 10% preferably less than 5% change in weight, length and thickness of body.

According to an aspect of the present disclosure, a gastroretentive dosage form (GRDF) is provided that includes: a hinged body configured to transform between a collapsed configuration for ingestion and an expanded configuration for retention within the stomach for a predetermined time period, wherein the gastroretentive dosage form maintains a mechanical strength and dimensions such that.

a. after 12 hr exposure to simulated gastric fluids [Rotating apparatus having 37° C., pH2+Xanthan gum 0.125 gr/L, 25 RPM mixing]—less than 5%, preferably less than 3% decrease in size when placed in a compression modulus with repeated force applied in the direction of refolding of 150 g/mm, up to 750 g b. after more than 8 hr exposure to simulated gastric fluids [Rotating apparatus having 37° C., pH2 Xanthan gum 0.125 gr/L, 25 RPM mixing]—size maintained to prevent passage through the 18 mm pipe test under 600 gr/F c. after more than 24 hrs in a pig stomach—size maintained d. after more than 24 hrs in a beagle dog stomach, 50% of the GRDFs maintained size e. after 24 hr exposure to simulated gastric fluids—less than 10% preferably less than 5% change in weight, length and thickness of body.

According to an aspect of the present disclosure, a gastroretentive dosage form (GRDF) for extended retention in a stomach is provided that includes: a non-biodegradable body including a first arm and a second arm configured to move between a collapsed configuration for ingestion to an expanded configuration for retention in the stomach, the non-biodegradable body comprising a mixture including a pharmaceutically acceptable material and a plasticizer in a ratio ranging from about 3:1 to about 12:1.

According to an aspect of the present disclosure, a gastroretentive dosage form (GRDF) for extended retention in a stomach is provided that includes: a body configured to transform between a collapsed configuration for ingestion and an expanded configuration for retention within the stomach for a predetermined time period, wherein the GRDF exhibits gastric retention for more than 24 hrs under fasted conditions in about 50% beagle dog.

According to an aspect of the present disclosure, a gastroretentive dosage form (GRDF) is provided that includes: a body configured to transform between a collapsed configuration for ingestion and an expanded configuration for retention within the stomach for a predetermined time period, wherein the GRDF does not pass the 18 mm pipe test under 300 grForce after exposure to simulated gastric conditions for 24 hrs.

According to an aspect of the present disclosure, a gastroretentive dosage form (GRDF) is provided that includes: a body made of a pharmaceutically acceptable material and including an API having a size and strength maintained after more than 85% API is release, such that it cannot pass the 18 mm pipe test under 300 grForce.

According to an aspect of the present disclosure, a gastroretentive dosage form (GRDF) is provided that includes: a body configured to transform between a collapsed configuration for ingestion and an expanded configuration for retention within the stomach for a predetermined time period, wherein the GRDF does not pass the leaf durability test under 1250 grForce and exposure to simulated gastric conditions for 12 hrs.

According to an aspect of the present disclosure, a gastroretentive dosage form (GRDF) is provided that includes: a body configured to transform between a collapsed configuration for ingestion and an expanded configuration for retention within the stomach for a predetermined time period, wherein the body displays less than 6% deformation when compressed by 350 grF after exposure to simulated gastric conditions for 12 hrs.

In any of the aspects described herein, the GRDF further comprises an active pharmaceutical ingredient. In any of the aspects described herein, the GRDFs described herein may include a body which includes a volume ranging from about 100 mm$^3$ to about 2000 mm$^3$. In aspects, the volume of the body may range from about 200 mm$^3$ to about 1800 mm$^3$. In aspects, the volume of the body may range from about 500 mm$^3$ to about 1500 mm$^3$. In embodiments, the volume of the body may range from about 800 mm$^3$ to about 1200 mm$^3$. In aspects, the volume of the body may be about 950 mm3. In any of the aspects described herein, the GRDF is folded and positioned in a capsule.

In any of the aspects described herein, any of the GRDFs described or envisioned herein may include an emergency release feature that allows the GRDF to pass through the pyloric valve for immediate removal from the stomach and gastrointestinal tract, if needed or causes immediate disassembly outside of the gastric environment. Either in the presence or upon exposure to an antidote or environment different than typical gastric, the GRDF is configured to disassemble for passage from the stomach prior to expiration of the predetermined period of time or disassemble if it has passed the gastric environment. An antidote or other triggering mechanism may be employed to initiate the emergency release of the GRDF. In aspects, the GRDF includes a hinge assembly (or any other portion thereof) that is pH sensitive (for example sensitive to a pH 5-5.5) such that under normal gastric conditions the hinge assembly (or any portion thereof) remains intact and the GRDF functions as intended. However, if needed, the environmental pH can be slightly increased (to within the above pH sensitive range or any other specified range) causing the mechanical integrity of the hinge assembly (or any portion thereof) to erode causing the hinge assembly to disassemble from one or both arms and pass through the pyloric valve for subsequent evacuation. For example, in aspects, the erosion may cause reduced mechanical pressure between the insert and the hinge assembly (or a portion thereof) to eventually release the hinge assembly from one or both arm(s) and pass from the stomach.

In any of the aspects described herein, the pH-sensitive materials making up only part of the GRDF for the emergency release may include materials which dissolve, erode, and/or degrade at a pH higher than 5, and more particularly from a pH which ranges from about 5 to 7.5. Some non-limiting examples of suitable pH-sensitive materials include polyacrylamides, phthalate derivatives (i.e., compounds with covalently attached phthalate moieties) such as acid phthalates of carbohydrates, amylose acetate phthalate, cellulose acetate phthalate, other cellulose ester phthalates, cellulose ether phthalates, hydroxypropyl cellulose phthalate, hydroxypropyl ethylcellulose phthalate, hydroxypropyl methyl cellulose phthalate, methyl cellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene and maleic acid copolymers, formalized gelatin, gluten, shellac, salol, keratin, keratin sandarac-tofu, ammoniated shellac, benzophenyl salicylate, cellulose acetate trimellitate, cellulose acetate blended with shellac, hydroxypropylmethyl cellulose acetate succinate, oxidized cellulose, polyacrylic acid derivatives such as acrylic acid and acrylic ester copolymers, methacrylic acid and esters thereof, vinyl acetate and crotonic acid copolymers.

In any of the aspects described herein, the body or the GRDF including any of the components of the GRDF, i.e., the body, arms, hinge assembly, etc., is made from at least one pharmaceutically acceptable material and preferably it is comprised of only pharmaceutically acceptable material, for example based on FDA's IIG list. In any of the aspects described herein, the formulation may be non-biodegradable or biodegradable or particularly suitable for the injection molding process. The choice of pharmaceutically acceptable materials for GRDFs includes all materials that will maintain stability in the gastric environment and provide enough rigidity to prevent disassembly or disintegration prior to the desired time (preferably through fasted and fed states). Any acceptable pharmaceutically approved polymeric materials such as cellulose acetate, ethocel, eudragit, or hydroxypropyl cellulose acetate succinate, with or without addition of a plactisizer, can be used for preparation of the GRDF. If the desire is a non-biodegradable formulation, one may provide, for example, a cellulose ester with plasticizer. In any aspect described herein, the materials are selected and processed in a way that will enable each of the components of the GRDF to operate according to its defined functionality (e.g., rigidity for the arms and hinge, elasticity of spring, and stability in dissolution, as defined above). Different materials may be used in order to better balance between durability and safety or eventual disintegration; pH independence and dependence, etc. For example, in aspects, the ratio of cellulose acetate (CA) to plasticiser may contribute to the durability, elasticity, reduced brittleness, independence from pH changes and decreased erodability.

In any aspect described herein, the body is in a size, shape and durability suitable for be maintained while in the stomach for the predetermined time period. For example, the body may comprise: cellulose ester, HPMC acetate succinate, ethocel, eudragit or a plasticizer. The cellulose ester may be selected from the group consisting of cellulose acetate, cellulose triacetate, hydroxypropylmethylcellulose acetate succinate, cellulose proprionate, cellulose acetate proprionate, cellulose acetate butyrate, and combinations thereof. In aspects, the cellulose ester comprises cellulose acetate. In any of the aspects described herein, the cellulose ester and the plasticizer are combined in a ratio ranging from about 3:1 to about 8:1. In aspects, the cellulose ester and the plasticizer are combined in a ratio ranging from about 4:1 to about 6:1, in aspects, the cellulose ester and the plasticizer are combined in a ratio of about 4:1. In aspects, the polymer may be selected from a listing comprising any one or more of the following: cellulose ester, HPMC acetate succinate, ethocel or eudragit. The plasticizer may be any one or more of the following: dibutyl sebacate, triethyl citrate, polyethylene glycol, polyethylene glycol monomethyl ether, acetyl tributyl citrate, triacetine, glycerin, sorbitol, sorbitan solutions, castor oil, diacetylated monoglycerides, triethyl citrate, tributyl citrate and combinations thereof. More specifically, the cellulose ester may be cellulose acetate (CA). The cellulose acetate (CA) to plasticiser ratio may be from about 3:1 to about 12:1, or in other aspects from about 3.5 to about 8:1 or in another aspect from about 4:1 to about 6:1, or specifically 4:1.

In any of the aspects described herein, the body of GRDF comprises a plasticizer selected from the group consisting dibutyl sebacate, triethyl citrate, polyethylene glycol, polyethylene glycol monomethyl ether, acetyl tributyl citrate, triacetine, glycerin, sorbitol, sorbitan solutions, castor oil, diacetylated monoglycerides, triethyl citrate, tributyl citrate and combinations thereof. In any of the aspects described herein, the body may include more than about 50 mg of the plasticizer per unit dosage form, in aspects, more than about 100 mg of the plasticizer per unit dosage form, in aspects, more than about 150 mg of the plasticizer per unit dosage form, in aspects, more than about 180 mg of the plasticizer per unit dosage form, in aspects, more than about 190 mg of the plasticizer per unit dosage form.

In any of the aspects described herein, the body may include more than about 50 mg, or more than about 200 mg of the cellulose ester per unit dosage form. In aspects, the body includes more than about 400 mg of the cellulose ester per unit dosage form, in aspects, more than about 600 mg of the cellulose ester per unit dosage form, in aspects, more than about 700 mg of the cellulose ester per unit dosage form, in aspects, more than about 750 mg of the cellulose ester per unit dosage form.

In any of the aspects described herein, the pharmaceutically acceptable material is hydroxypropylmethylcellulose and the plasticizer is triethyl citrate. In any of the aspects described herein, the pharmaceutically acceptable material is hydroxypropylmethylcellulose and the plasticizer is polyethylene glycol. In any of the aspects described herein, the pharmaceutically acceptable material is ethylcellulose and the plasticizer is triethyl citrate. In any of the aspects described herein, the pharmaceutically acceptable material includes methacrylic acid and methyl methacrylate and the plasticizer is triethyl citrate.

In any of the aspects described herein, the GRDF formulation or controlled release formulation comprises cellulose ester and triacetin and is capable of less than 10% preferably less than 5% change in weight, length and thickness after 24 hr exposure to simulated gastric fluids.

In any of the aspects described herein, the body includes an opening defined therein configured to expose the API or diagnostic to gastric fluids in the stomach once the capsule at least partially dissolves. Thus, depending on the rate of API/diagnostic release or desired end point for gastric retention, the one or more openings may increase the surface area for release and erosion of the API/diagnostic or composition thereof.

In any of the aspects described herein, the GRDF provides mechanical strength and is capable of resisting forces applied by the stomach under both fed and fasted condition. The mechanical strength is sufficient to enable, upon expansion of the GRDF, the preservation of the expanded configuration to provide gastric retention. More specifically, there is provided a GRDF with collapsed and expanded configurations which resists mechanical gastric forces even for a period of time.

In any of the aspects, the GRDFs i.e., the body, arms, hinge assembly, etc., may provide a mechanical durability to remain intact, i.e., assembled, over a period of time and is capable of resisting forces applied by the stomach under both fed and fasted condition. The mechanical strength is sufficient to enable, upon expansion of the GRDF, the preservation of the expanded configuration to provide gastric retention. More specifically, there is provided a GRDF (e.g., a non-biodegradable GRDF) with collapsed and expanded configurations which resists mechanical gastric forces wherein the gastroretentive dosage form is adapted to or capable of maintaining mechanical strength and dimensions to endure any one or more of the following:

a. after 12 hr exposure to simulated gastric fluids [Rotating apparatus having 37° C., pH2+Xanthan gum 0.125 gr/L, 25 RPM mixing]—less than 5%, preferably less than 3% decrease in size when placed in a compression modulus with repeated force applied in the direction of refolding of 150 g/mm, up to 750 g b. after more than 8 hr exposure to simulated gastric fluids [Rotating apparatus having 37° C., pH2 Xanthan gum 0.125 gr/L, 25 RPM mixing]—size maintained to prevent passage through the 18 mm pipe test under 600 gr/F c. after more than 24 hrs in a pig stomach—size maintained d. after more than 24 hrs in a beagle dog stomach, 50% of the GRDFs maintained size e. after 24 hr exposure to simulated gastric fluids—less than 10% preferably less than 5% change in weight, length and thickness of body.

In any of the aspects described herein, the body comprises a mechanical durability to remain intact over a period of time of at least 1 hour and under a repeated force of at least 400 grF. In aspects, the time period is at least 3 hours, in aspects, the time period is at least 6 hours, in aspects, the time period is at least 9 hours, in aspects, the time period to remain intact is at least 24 hours. In any of the aspects described herein, the repeated force of at least 600 grF, in aspects, the repeated force ranges from about 400 to about 3000 grF.

In any of the aspects described herein, the pharmaceutical formulation may be able to be retained in a human stomach for a time period of more than 6 hours, in aspects, for a time period of more than 8 hours, in aspects, for a time period of more than 12 hours, in aspects, for a time period of more than 18 hours, in aspects, for a time period of more than 24 hours, in aspects, for a time period of more than 36 hours. In any of the aspects described herein the formulation further comprises retention arms or a hinge assembly.

In any of the aspects described herein the formulation further comprises retention arms or a hinge assembly.

In another aspect, a method is provided for ending gastric retention of the GRDF by inducing basic environment. As long as the hinge assembly engagement with the arms is environment sensitive, and the environment changes or can be induced to change, one can induce an end to gastric retention. The pH dependent polymer may be coating or involved in physical make up of an arm or hinge assembly.

In another aspect, GRDFs may be manufactured by a number of processes including injection molding 3D printing and the like, as will be clear to one skilled in the art, such as the manufacturing techniques described in WO 2003057197 or in Zema et. al., Journal of Controlled Release, Volume 159 (2012) 324-331. For example, a mold can be constructed in the desired shape of the GRDF and filled with appropriate material(s) in liquid state and then allowed to cure by chemical processes or cooled if thermosetting material(s) are used. The GRDFs described herein or any parts thereof, e.g., arms, hinge assembly, springs, etc. may be made from pharmaceutically acceptable materials or ingredients, e.g., one or more ingredients listed in the IIG guidelines. In aspects, the GRDF may include a body which is made from at least one pharmaceutically acceptable material wherein the size, shape, and durability of the body are maintained while in the stomach for a predetermined time period of gastric retention. The use of injection molding applied to the specified ingredients in the specified molds resulted in less than 10% variation, in embodiments, less than 5% variation, in detail as small as 500 μm.

In any aspect, the GRDF may be configured for use with one or more additional APIs with different release profiles, e.g., an additional API designed for immediate release. The additional API, (e.g., an API designed for immediate release) may be located at the distal end of the insert and used with a GRDF with an opening at a distal end of one or both arms. In this instance, the configuration of the GRDF along with the API being disposed at a distal end of the insert directs the initial infusion of gastric fluids into the distal opening of the one or both arms and into immediate contact with the additional API promoting immediate release. In aspects, additional API may be included as a layer encompassing the capsule or surrounding the GRDF, or a layer encompassing one or both arms (or portions thereof).

According to an aspect of the present disclosure, a method of assembling a gastroretentive dosage form (GRDF) is provided and includes: inserting an insert tablet into a cavity of a body formed by injection molding; and combining the body with a hinge assembly.

According to an aspect of the present disclosure, a method of delivery of an API or diagnostic is provided that includes administering to a patient a GRDF of any of the previous claims in a closed configuration.

According to an aspect of the present disclosure, a method of manufacturing a dosage form for gastric retention is provided that includes forming a body of the dosage form including a cellulose ester composition.

In any aspect described herein, the cellulose ester composition includes a cellulose ester and a plasticizer. In aspects, the cellulose ester is cellulose acetate and the plasticizer is triacetin.

According to an aspect of the present disclosure, a method of forcing a disassembly of a GRDF within a patient is provided that includes: administering a GRDF to a patient; and administering an antidote to the patient, wherein the antidote increases a pH of the patient's stomach forcing the GRDF to disassemble into pieces of sufficient size to evacuate the stomach.

In aspects, the GRDF includes a body comprising a pH sensitive material which represents less than about 20% of a total weight of the body, wherein the pH sensitive material is configured to force the GRDF to disassemble.

According to an aspect of the present disclosure, use of an immediate release formulation in the manufacture of a GRDF is provided. In any of the aspects described herein, the formulation is an insert (tablet).

According to an aspect of the present disclosure, a controlled release formulation is provided that includes a body including a cavity suitable for retaining an API composition, wherein the body defines a surface area of exposure of the API composition which allows for the controlled release of the API.

In any of the aspects described herein, the API is released over more than 4 hours, in aspects, over more than 8 hours, in aspects, over more than 12 hours, in aspects, over more than 18 hours, in aspects, over more than 24 hours.

BRIEF DESCRIPTION OF THE DRAWING FIGURES

Various aspects of the present disclosure are described herein with reference to the drawings wherein like reference numerals identify similar or identical elements:

FIGS. 24A and 24B depict varying perspective views of a clip portion of the hinge assembly of FIGS. 23A through 23D;

FIGS. 25A and 25B depict varying perspective views of a post portion of the hinge assembly of FIGS. 23A through 23D;

DETAILED DESCRIPTION

Figure 1:
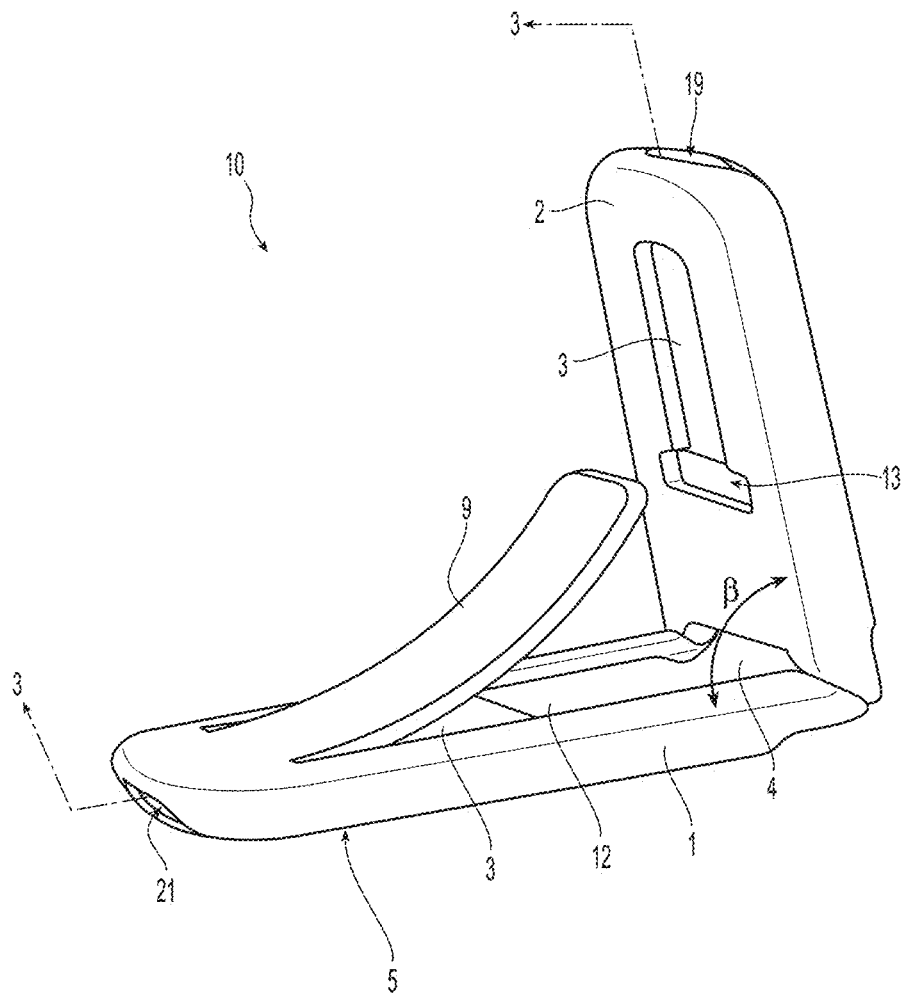
FIG. 1 depicts a perspective view of an oral pharmaceutical or gastroretentive dosage form (GRDF) shown in an expanded configuration, according to a first exemplary embodiment of the present disclosure.

All of the patent references and journals that are referenced herein are incorporated by reference herein in their entirety and for all purposes.

The wording hereinbelow is implied in the common meaning of the definitions and statements as known to those skilled in the art. However, there are several terms that should be understood in the concept of the present disclosure as follows:

"Gastroretentive dosage form(s)" (GRDF or GRDFs in the plural) refers to dosage forms which reside in the confines of the stomach for the purpose of providing a platform for the controlled release of biologically active agents or diagnostic formulations. The GRDF is also referred to herein as an oral pharmaceutical, as well as a dosage form for extended retention in a stomach.

"Gastric retention" is the maintenance or holding of a pharmaceutical in the stomach, for a time period longer than the time it would have been retained in the stomach when delivered in a free form or within a gastro-intestinal (GI) delivery vehicle which is not considered gastroretentive. Gastro-retentivity may be characterized by retention in the stomach for a period that is longer than the normal emptying time from the stomach, such as longer than about 2 hours, in some cases longer than about 3 hours, and in many cases more than about 4, 6, 8 or 10 hours. Gastro-retentivity typically means retention in the stomach for a period of time of about 3, 4, 6, 8, 10, or at times 18 hours, even up to about 21 hours or longer. Gastro-retentivity may also mean retention in the stomach for a predetermined time period of at least 4, 6, 8, 10, 12, and 18 hours.

As used herein, a size "suitable for swallowing" is any size and/or shape of a pharmaceutical unit that is capable of being swallowed by either a human or an animal.

As used herein, a "body" is meant to include any collection of parts or materials that are more or less constrained or otherwise connected to move together by translation or rotation, As used herein, "excipient" refers to a component, or mixture of components, that is used in the formulation of the compositions or inserts of the present disclosure to give desirable characteristics to the composition or insert. As used herein, the term "pharmaceutically acceptable" refers to those compounds, materials, compositions, compacts, salts, and/or dosage forms which are, within the scope of sound medical judgment, suitable for contact with the tissues of human beings and animals without excessive toxicity, irritation, allergic response, or other problematic complications over the desired duration of treatment commensurate with a reasonable benefit/risk ratio. In some embodiments, the term "pharmaceutically acceptable" means approved by a regulatory agency of the Federal or a state government or listed in the U.S. Pharmacopeia or other generally recognized international pharmacopeia for use in animals, and more particularly in humans. Various pharmaceutically acceptable excipients can be used. In some embodiments, the pharmaceutically acceptable excipient can be, but is not limited to, an alkaline agent, a stabilizer, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, Remington: The Science and Practice of Pharmacy, 21st ed. (2005). Inclusion of an excipient in a particular classification herein (e.g., "solvent") is intended to illustrate rather than limit the role of the excipient. A particular excipient can fall within multiple classifications.

As used herein, an "oral pharmaceutical" is anything administered orally whose components are made up of pharmaceutically acceptable materials.

As used herein, diagnostic or an active pharmaceutical ingredient (API) is meant to include any substance relevant for gastric retention as recognized in the art. A wide variety of APIs (which may be therapeutic, diagnostic or otherwise beneficial) may be employed in accordance with the aspects of the present disclosure. Any API which is relevant for gastric retentive delivery or as a diagnostic known in the arts is intended to be encompassed herein. Relevant APIs are not limited to, but may include the following: APIs acting locally in the stomach; APIs primarily absorbed in the stomach; APIs poorly soluble in alkaline pH; APIs with narrow windows of absorption; APIs absorbed rapidly from the GI tract; APIs that degrade in the colon; and APIs that disturb colonic microbes.

Active pharmaceutical ingredients (APIs) may include but are not limited to the following: prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, tolazamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-nor-progesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, cyclosporins such as cyclosporine A, insulin, coichicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

As used herein, the term "arm" or "arms" includes any structure that includes a length, width and thickness and aids in achieving size for gastric retention. An arm as described herein may retain an active pharmaceutical or diagnostic. It may define a cavity therein configured to retain an insert or pharmaceutical tablet (made from one or more APIs, diagnostics, excipients and/or polymers). An arm as described herein may be made from API, diagnostics, polymers, excipients, etc.

As used herein, the term "hinge assembly" includes any mechanism adapted to permit relative movement between two or more structures, e.g., arms. The hinge assembly may consist of one integral part (e.g., a living hinge) or one or more parts that are assembled in the conventional sense. The hinge assembly may be durable in the stomach for a period of time, and it may attach to one or more arms in both the collapsed and expanded configurations. The hinge assembly may be capable of, at a predetermined time or upon occurrence of a mechanical event, disengaging from the one or more arms.

As used herein, the term "mechanical event" includes any event that changes the physical properties of one or more structures over time or upon contact with another material or fluid, e.g., gastric fluid inside the body. Absorption, dissolution, melting, degradation, erosion, pH change or temperature change, etc. are all examples of mechanical events.

As used herein an "erodible" material includes any material that degrades upon introduction to a specified environment or upon contact with a specified material or fluid, e.g., a gastric environment or gastric fluid.

As used herein, the term "collapsed configuration" of the GRDF is that state prior to ingestion where the GRDF is a size suitable for swallowing.

As used herein, the term "expanded configuration" of the GRDF is that state after ingestion which is capable of maintaining the GRDF in the stomach (gastric retention) and preventing passage through the pyloric valve.

As used herein, the term "upon exposure to gastric fluid" or under simulated gastric conditions is meant to be taken literally or when needed, based on a suitable model. One example of such a suitable model includes exposure to 400 ml of 0.1N HCl and 150 gram glass beads in a 500 mL dissolution chamber, at 37° C. at 8 RPM. In another model, Xanthan gum 0.125 gr/L, pH2 is at 37° C.

As used herein, the term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The present disclosure provides a GRDF and a method of use thereof. The GRDF is swallowed in a collapsed configuration, expands in the stomach, performs its intended function for a predetermined time period, and at the end of the time period or upon occurrence of a mechanical event, disassembles and/or disintegrates for eventual passage through the pyloric valve of the stomach. After exiting the stomach, the GRDF safely passes through the rest of the gastrointestinal system and/or is simply absorbed by the body. In embodiments, the GRDF is configured to disintegrate completely. In other embodiments, the GRDF is configured to only disintegrate to an extent necessary for evacuation. In yet other embodiments, parts of the GRDF do not disintegrate and are evacuated intact for later retrieval, e.g., for diagnostic purposes or when the GRDF houses a diagnostic device.

It should be understood that the gastric retention may be attained due to the arms and/or hinge assembly, while the structure of the arms (with slight modifications of formulation of the insert depending on length of time needed) provide for the controlled release of the API or diagnostic.

Figure 16:
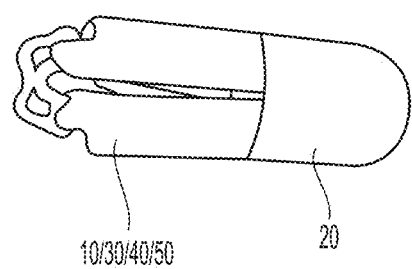
FIG. 16 depicts the GRDF of FIG. 1 in a collapsed configuration and positioned in one half of a delivery capsule, the other half of the delivery capsule being omitted to better show the collapsed condition of the hinge.

Referring now specifically to one embodiment of a GRDF generally designated by reference numeral 10 shown in FIGS. 1-8 and 16, GRDF 10 includes a body 5 having first and second arms 1 and 2, respectively, that are releasably connected to one another by a hinge assembly 4. Arms 1 and 2 are capable of pivoting about hinge assembly 4 from a collapsed configuration, as shown in FIG. 16, to an expanded configuration, as shown in FIG. 1. In embodiments, the hinge assembly 4 is made from pharmaceutically acceptable materials or ingredients.

In the expanded configuration, the arms 1 and 2 may be oriented at an internal angle $\beta$. In embodiments, angle $\beta$ is more than 90 degrees. In another envisioned embodiment, the internal angle $\beta$ between arms 1 and 2 may be between about 45 degrees and about 90 degrees. In one embodiment, the internal angle between arms 1 and 2 may be between about 45 degrees to about 80 degrees. Each arm 1 and 2 includes a substantially hollow inner cavity 24 and 25, respectively, defined therein and configured to receive an insert 3 that may include any combination of active pharmaceutical ingredients (APIs), diagnostic devices or materials and/or various excipients and polymers. It should, of course, be understood that in embodiments only one of arm 1 or arm 2 is configured to receive the insert 3.

Figure 3:
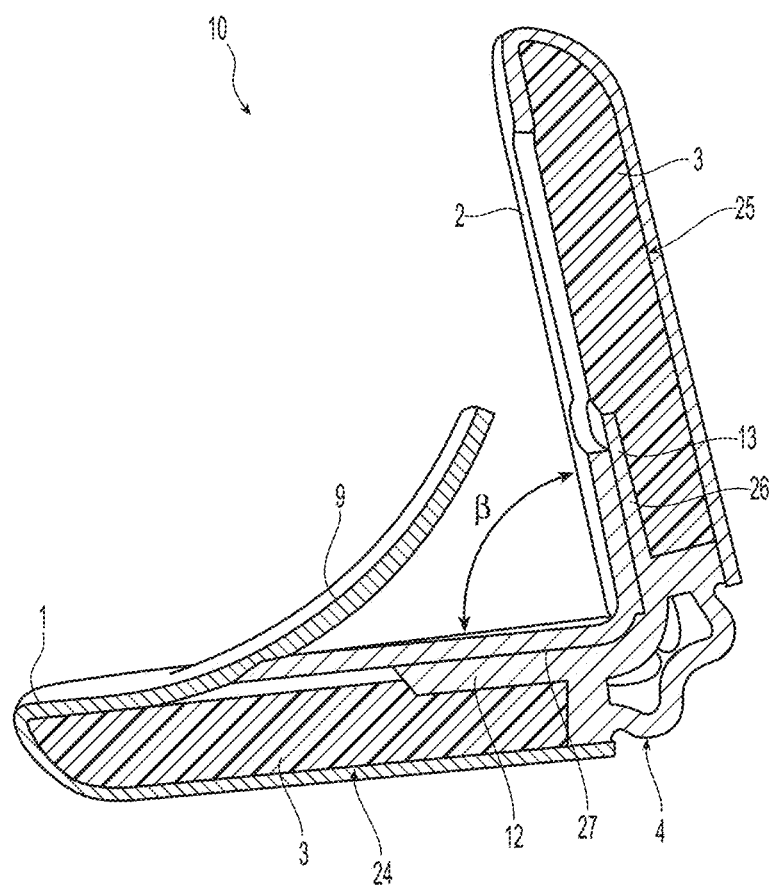
FIG. 3 depicts a cross-sectional view of the GRDF of FIG. 1 taken along line 3-3 of FIG. 1.
Figure 4:
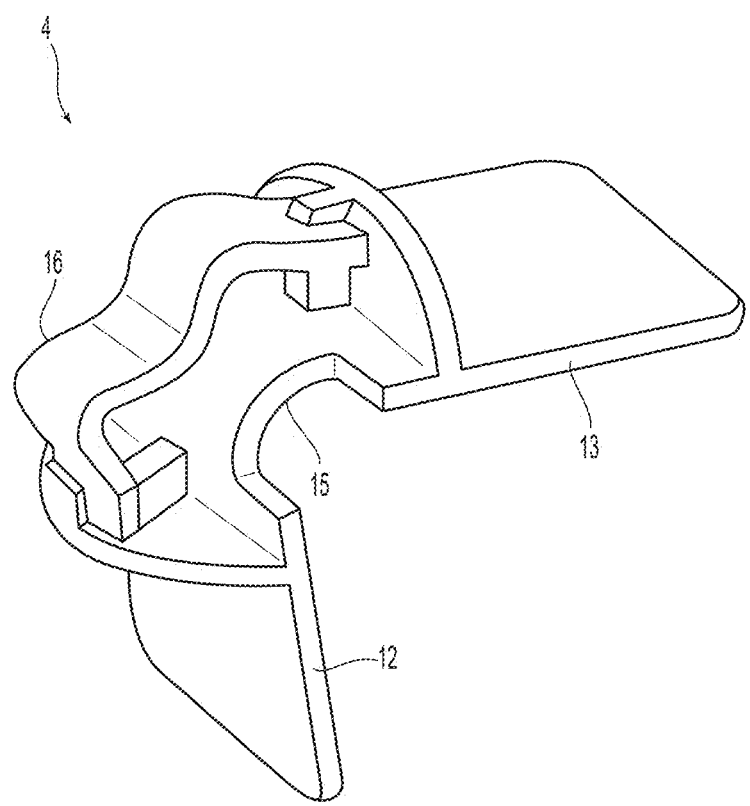
FIG. 4 depicts a perspective view of a hinge of the GRDF of FIG. 1 in an open configuration.

As shown in FIG. 4, hinge assembly 4 includes a pair of opposing biasing elements 12 and 13 that are configured to mechanically engage arms 1 and 2, respectively. Elements 12 and 13 are joined together by a living hinge 15 which includes an elastically deformable portion 16 that biases elements 12 and 13 (and, in turn, arms 1 and 2) into the expanded configuration (See FIGS. 3 and 4) once deployed as explained in more detail below. Hinge assembly 4 may be unitary, as shown, or it may include multiple components (e.g., components that separate after a predetermined period within the stomach or upon occurrence of a mechanical event—See FIGS. 17-33).

As can be appreciated, hinge assembly 4 connects arms 1 and 2, however, any physical or mechanical mechanism(s) may be employed to connect arms 1 and 2. For example, instead of hinge assembly 4, arms 1 and 2 may be connected by a clip, clamp, snap, weld, adhesive, joint, dovetail, mating surface(s), tether, post, pin, slot, recess, fastener, fixture, mechanical thread, friction, or stitch for example. The connection of the arms 1 and 2 to the hinge assembly 4 may be accomplished by adhesive/chemical bonding such as a pharmaceutical binder which functions as a glue, for example. Alternatively, the arm-to-hinge assembly interface may include any known mechanical engagement.

Figure 5A:
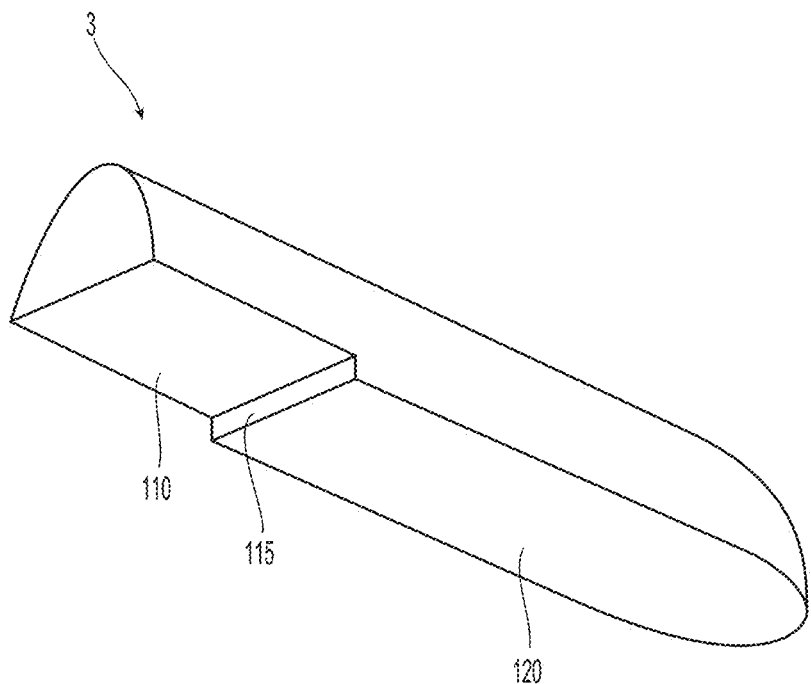
FIG. 5A depicts a perspective view of an insert of the GRDF of FIG. 1.

FIG. 5A shows a perspective view of the insert 3 which may be inserted into respective cavities 24 and 25 defined within one or both arms 1 and 2. As can be appreciated, insert 3 is structure that holds or contains the API or diagnostic. Insert 3 may include any geometric shape and the corresponding cavity, e.g., cavity 24 of arm 1, may include a complementary geometric shape to receive the insert 3 in a manner that allows mechanical separation of the arm, e.g., arm 1, after a predetermined time period or upon occurrence of a mechanical event as described in more detail below. As shown, insert 3 includes an exposed surface 120 and an engagement surface 110 separated by a ledge 115. The exposed surface 120 is that portion of the insert 3 that contains the API or diagnostic and which is exposed to the gastric fluids as described below. The engagement portion 110 and the ledge 115 cooperate to maintain engagement of the insert 3 with the hinge assembly 4 until a sufficient portion of the engagement portion 110 or the ledge 115 erodes upon exposure to gastric fluids and the mechanical integrity of the GRDF 10 fails causing disassembly. As can be appreciated, the engagement portion 110 and/or ledge 115 may be any geometric shape that together with the geometric shape of the insert 3 maintain the GRDF 10 in an assembled configuration prior to erosion.

Each insert 3 may be formulated to include one or more active pharmaceutical ingredients (APIs), various diagnostic materials or devices, or a variety of excipients and polymers depending upon a particular purpose. The API is not limited to any particular class of pharmaceutical. The diagnostic material or device may be a camera, a sensor, a microchip, a radioactive tracer, a combination of one or more chemical strips or testing fixtures, micro genetic labs or arrays and the like, e.g., commonly terms "lab-on-a-chip technologies", etc. The diagnostic may or may not be erodible. In embodiments, the diagnostic device may be retrievable or programmed to communicate with an outside source. In embodiments where it is desirous to maintain the integrity or partial integrity of the diagnostic device (such as where the diagnostic is not erodible) then either arm 1 or 2 and/or the hinge assembly 4 may be erodible to achieve disassembly of the GRDF 10.

Figure 5B:
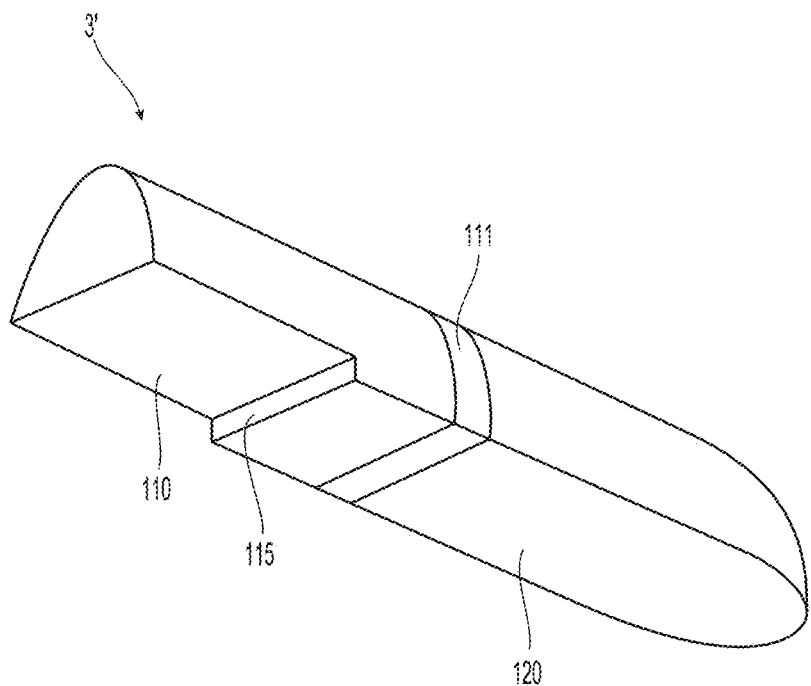
FIG. 5B depicts a perspective view of another embodiment of an insert of the GRDF of FIG. 1 including two active pharmaceutical ingredients separated by a non-active pharmaceutical ingredient.

As an alternative to the unitary insert 3 that is shown in FIG. 5A and described herein, more than one API may also be separated into separate inserts or tablets, for example, when there are incompatible chemicals that cannot be readily combined into a single unitary insert 3 or formulation. In other embodiments, the insert 3 may be compartmentalized or layered to control the rate of release of the API. For example, FIG. 5B depicts a perspective view of another embodiment of insert 3' that includes two APIs separated by a non-active pharmaceutical ingredient 111. In this instance, the insert 3' may include a portion containing an API which releases at a predetermined rate, followed by a portion containing no API (placebo or various excipients or polymers that erode at a predetermined rate), followed by a portion that includes the same or a different API. As can be appreciated, controlling the release of API in this manner can mimic a particular dosing schedule for a particular patient alleviating the need for the patient to take repeated dosages of a particular medicine at particular time periods. Moreover, depending upon the various polymers and excipients used or the shape of the insert 3 or 3', the dosage period may be lengthened considerably.

For example, a person having to take a medicine three times per day may be reduced to a once-per-day dosage. Someone having to take a medicine once-per-day may be able to take a GRDF 10 once-per-week or longer and deliver the same effective dosing. In this instance, the GRDF 10 is configured to facilitate erosion or dissolution of the insert 3 (which releases the API) in a predetermined manner or along a particular erosion pathway. It is important to note, the structure holding the API or diagnostic in place, e.g., the insert which includes an API composition including polymers and excipients, dissolves, disintegrates, erodes, etc. thereby releasing the API and/or exposing/releasing the diagnostic.

As explained in more detail below with reference to the configuration of the various openings and slots defined within the arms 1 and 2 of the GRDF 10, this may be accomplished by controlling or limiting the exposure of the insert 3 to certain areas along the arms 1 and 2, e.g., controlling the amount of surface area of the insert 3 exposed to gastric fluids along the GRDF 10. As can be appreciated, controlling the release rate of the insert 3 in any of the fashions described herein may extend the life of the insert 3 and enable one GRDF to effectively provide the necessary API over an extended period of time while being retained within the stomach.

With respect to embodiments where the insert 3 includes a diagnostic material or device, after ingestion, the GRDF 10 expands for retention within a subjects stomach for a predetermined period of time to complete the diagnostics. During this time, other portions of the GRDF 10 are exposed to gastric fluids which erode or dissolve one or more portions of the GRDF 10 (e.g., hinge assembly 4 or hinge arms 12 and 13) over the predetermined time or upon the occurrence of a mechanical event. Once eroded, the GRDF 10 disassembles and moves through the pyloric valve and through the intestinal tract for subsequent retrieval.

Figure 6:
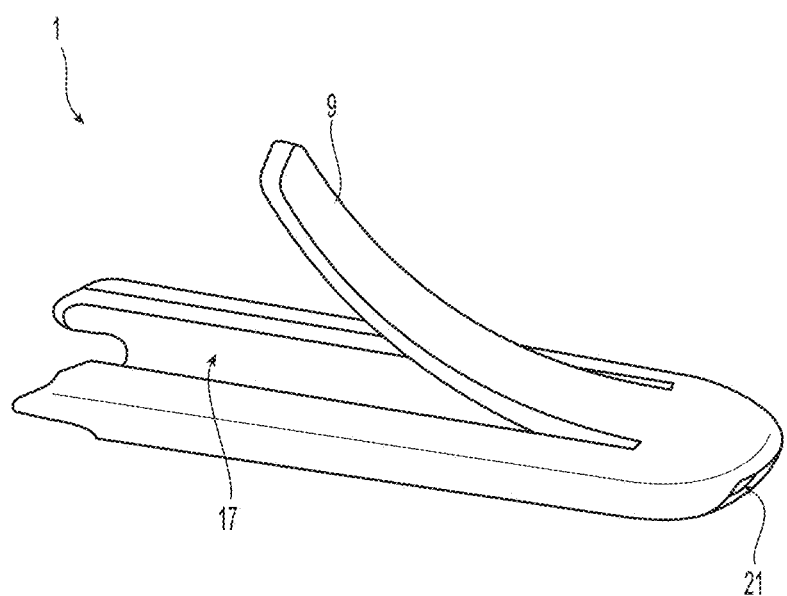
FIG. 6 depicts a perspective view of a first biasing arm of the GRDF of FIG. 1.

FIG. 6 depicts a perspective view of the first arm 1 of the GRDF 10. As noted above, the interior of arm 1 includes a cavity 24 to accommodate insert 3 that has a complementary shape to insert 3, e.g., a semi-cylindrical shape with a semi-spherical surface at a free end there of that accommodates the corresponding semi-spherical surface of insert 3. The inner facing surface of arm 1 includes an opening 17 defined therein which is configured to expose a portion of insert 3 to gastric fluids. Alternatively or in addition to opening 17, another opening 21 may be defined in the distal end of arm 1 (i.e., the end furthest from hinge assembly 4) which is configured to expose the distal-most portion of the insert 3 to gastric fluids to encourage or promote a distal-to-proximal pathway of erosion of the insert (and release of the API or diagnostic) and eventual disassembly of the of GRDF 10. A variety of slots 18 may also be defined within one or both arms 1 and 2 (See FIG. 8).

As explained in further detail below, promoting the release or erosion of the insert 3 in this fashion may facilitate mechanical disassembly of the GRDF 10 after the predetermined time period. In other words, the shape, size and location of opening 21 may influence the release timing or erosion of one or more components of the GRDF 10 which correlates to the overall time the GRDF 10 is maintained within the stomach. As can be appreciated, additional openings and or slots of varying size and shape may be defined within the arms 1 and 2 depending upon the length of gastric retention of the GRDF 10 desired or the rate of erosion desired of the insert 3 (See FIGS. 33 through 35). For example, in one embodiment, distal opening 21 may be the only area of the GRDF 10 that exposes the insert 3 to gastric fluids which, as mentioned above, may create a distal-to-proximal pathway of erosion of the insert 3. In this instance the insert 3 erodes proximally or along a proximal pathway (and release API in a controlled fashion) over a predetermined time until enough of the insert 3 is eroded and the GRDF 10 loses mechanical integrity to hold its shape and disassembles for passage through the pyloric valve.

As shown in FIG. 6, a biasing element 9 may be integral with arm 1 and elastically deformable relative thereto. Biasing element 9 is configured to bias arms 1 and 2 into the expanded configuration of the GRDF 10 as shown in FIG. 1. Once the GRDF 10 is expanded within the stomach, biasing element 9 also prevents arms 1 and 2 from returning to the collapsed configuration that is shown in FIG. 16. Biasing element 9 may be configured to engage a corresponding T-shaped slot 18 defined within arm 2 to prevent the arms 1 and 2 from returning to the collapsed configuration. According to another embodiment, biasing element 9 may be omitted, and the hinge assembly 4 may be formed of a shape memory material (SMM) such as polylactic acid or a shape memory alloy (SMA), e.g., Nitinol®, which is configured to prevent arms 1 and 2 from returning to the collapsed configuration. Other elements of the GRDF 10 may also be formed of SMMs or SMAs as explained in more detail below.

Figure 7:
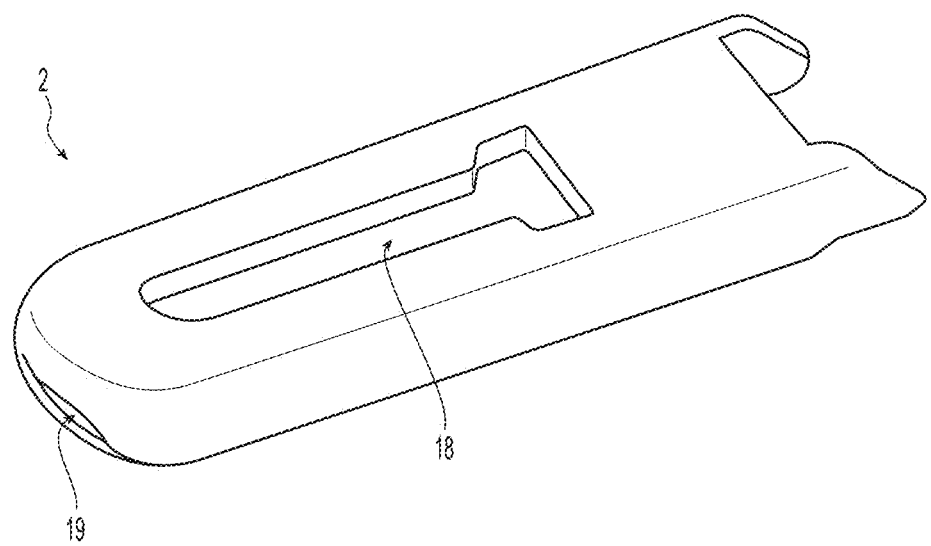
FIG. 7 depicts perspective view of a second arm of the GRDF of FIG. 1.

FIG. 7 shows a perspective view of second arm 2 of the GRDF 10. Arm 2 also includes a semi-cylindrical shape with a semi-spherical surface at one end. The interior of arm 2 also includes a cavity 25 defined therein configured to accommodate a second insert 3 (e.g., a different insert 3 than is contained within arm 1). Second insert 3 may include the same APIs as the insert in arm 1 or different APIs than the insert in arm 1 or may include one or more diagnostics. The inner facing surface of arm 2 includes a T-shaped slot 18 defined therein which is configured to expose a portion of insert 3 to gastric fluids. Any number or configuration of slots 18 may be utilized in conjunction with any number of openings (e.g., similar to opening 17 with respect to arm 1) or T-shaped slot 18 may be omitted or partially omitted depending upon a particular purpose. A distal opening 19 may be defined at the distal end of arm 2 (furthest from hinge assembly 4). Similar to the opening 21 described above, opening 19 is configured to expose a portion of insert 3 to gastric fluids in the stomach such that the insert 3 erodes in a distal-to-proximal manner. As explained above, promoting the release or erosion of the insert 3 in this fashion may facilitate mechanical disassembly of the GRDF 10 after the predetermined time period. Again, the shape, size and location of slot 18 and opening 19 influence the release of the API and the retention time of the GRDF 10 within the stomach.

Arms 1 and 2 may have a longest length of between 15 and 50 mm, in embodiments, between about 20 and 40 mm. Once in expanded state, the longest length of the GRDF 10 may be more than about 15 mm, in embodiments, more than 20 mm, in other embodiments more than 25 mm, in yet other embodiments between 26 mm and 32 mm. Without compromising other advantages of the disclosure, the longest length of arms 1 and 2 may be more than 25 mm or more than 27 mm. In a collapsed state, the longest length of the GRDF may be between 15 and 50 mm, and the diameter of the GRDF 10 (if it has a circular cross section) may be 13 mm or less. In embodiments, the diameter may be less than about 11 mm, in other embodiments less than 10 mm, in other embodiments less than 9 mm and in yet other embodiments either 9.9 mm or 8.5 mm. In the expanded configuration, the GRDF 10 is sized and shaped for retention within the stomach until disassembly. The geometric formation of arms 1 and 2 in the expanded configuration of the GRDF 10 may contribute to retention of the GRDF 10 within the stomach. In embodiments, the GRDF 10 may be triangularly-shaped to accomplish this purpose but other geometric shapes are envisioned, e.g., any polygonal shape. In this instance, additional hinge assemblies and arms may be required to shape the GRDF once expanded.

In embodiments, the arms 1 and 2, the hinge assembly 4 and/or the biasing element 9 are injection molded components. In embodiments, the arms 1 and 2 and/or hinge assembly 4 may be configured to eventually degrade in the stomach. In other embodiments, arms 1 and 2 or hinge assembly 4 may be configured to retain their size and shape in the stomach, but, once disassembled, are easily passable through the pyloric valve. In yet other embodiments, the arms 1 and 2 and the hinge assembly 4 are made from materials that erode (or degrade) over time or upon occurrence of a mechanical event to fully pass through the pyloric valve and the remainder of the gastrointestinal tract. Examples of such materials are shown in one or more tables of the Examples disclosed herein.

In a first, collapsed and stowed configuration of the GRDF 10, the GRDF 10 is of a size that is easily swallowable by a patient. As shown in FIG. 16, the GRDF 10 may be encapsulated within a dissolvable capsule 20. Any biocompatible capsule known to those skilled in the art may be used to maintain the GRDF 10 in the collapsed state. The assembly of the GRDF 10 and encapsulation can be done manually or by any suitable robotic automated machine. In FIG. 16, only one half of the dissolvable capsule 20 is shown. The other half of capsule 20 is omitted to reveal the collapsed configuration of the GRDF 10. In this configuration, the biasing element 9 of the GRDF 10 is collapsed between arms 1 and 2. Other retention mechanisms are contemplated to retain the GRDF 10 in a collapsed configuration for ingestion and then permit expansion of the GRDF 10 to the expanded configuration once ingested, e.g., a biodegradable band.

Once swallowed and ingested, the gastric fluids of the stomach dissolve the capsule 20 and the biasing element 9 urges the arms 1 and 2 apart to a second, expanded configuration of the GRDF 10, e.g., as shown in FIG. 1. Once in the expanded configuration, the GRDF 10 is of a size that prevents the GRDF 10 from passing through the pyloric valve until disassembly of the GRDF 10. In embodiments, the GRDF 10 is retained within the stomach for a predetermined amount of time irrespective of fasted or fed conditions. The predetermined amount of time may be 4 hours, 6 hours, 7 hours, 8 hours, 10 hours, or 12 hours, under fasted conditions, for example. The predetermined amount of time is at least 8 hours, in embodiments, 10 hours, under fed conditions, for example. In embodiments, the predetermined amount of time the GRDF 10 is retained within the stomach is at least 4 hours under fasted or fed conditions. In embodiments, the predetermined amount of time the GRDF 10 is retained within the stomach is less than 18 hours under fasted or fed conditions. In embodiments, the predetermined amount of time (e.g., end point of gastric retention) is dependent on the extent of API release or erosion time of the insert.

As noted above, the GRDF 10 remains in the second, expanded configuration within the stomach until the insert or inserts 3 erode. More particularly, in an assembled form of the GRDF 10, arms 12 and 13 of the hinge assembly 4 are engaged (frictionally or otherwise) between one of the inserts 3 and an interior wall 27 and 26 of cavities 24 and 25 of the arms 1 and 2, respectively. The friction provided between the sandwiched parts maintains the GRDF 10 in an assembled condition for a pre-determined amount of time inside the stomach. As the insert or inserts 3 erode and release the API (or allow the diagnostic to perform its testing), the mechanical integrity of the GRDF 10 (or more specifically the mechanical engagement of the hinge assembly 4 with the arms 1 and 2) begins to weaken and eventually fail thereby disengaging the hinge assembly 4 from the arms 1 and 2.

For example, insert 3 of arm 2 begins to erode at the distal end thereof via gastric fluids entering opening 19 and insert 3 of the arm 1 begins to erode at the distal end thereof via gastric fluids entering opening 21 in arm 1. In this instance, dissolution and erosion of each insert 3 occurs gradually from the distal end of each insert 3 to the proximal end of each insert 3 towards the mechanical connection with hinge assembly 4. As mentioned above, gastric fluids may also enter other slots or openings, e.g., slot 18 or opening 17, defined in the arms 1 and 2 at the same time or sequentially. Once the inserts 3 have sufficiently eroded, the friction force between the sandwiched components (hinge arms 12 and 13 and respective ledges 115 and engagement portions 110 of the inserts 3) is no longer sufficient to hold the individual components of the GRDF 10 together whereupon the individual components of the GRDF 10 (hinge assembly 4, arms 1 and 2) detach from each other, thereby forming a third, disassembled configuration of the GRDF 10.

The individual components of GRDF 10 are sized to pass through the pyloric valve and subsequent gastrointestinal tract as two or more separate components (e.g., arms 1 and 2, and hinge assembly 4 or arm 1 and hinge assembly 4 still joined to arm 2). As described herein, hinge assembly 4 may also include multiple components. In one embodiment, the hinge assembly 4 may be formed from and/or coated with a pH sensitive erodible material, e.g., a material sensitive to the pH of a certain portion of the gastrointestinal tract, such that the hinge assembly 4 reduces in size during transit through that portion of the gastrointestinal tract. For example, the hinge assembly 4 may include a material that reduces in size at a location of the gastroinstestinal tract beyond the stomach, e.g., small and/or large intestines, at a pH of about 5 to about 7.5. As can be appreciated, in the rare instance when the GRDF 10 is ingested and passes through the pyloric valve prior to expansion (e.g., prior to the retention mechanism (capsule 20) dissolving), constructing the hinge assembly 4 from a pH sensitive erodible material facilitates rapid erosion of the hinge assembly 4 in the gastrointestinal environment and initiates disassembly of the GRDF for safe passage through the gastrointestinal tract and eventual evacuation.

In embodiments, the pH-sensitive materials may include materials which dissolve, erode, and/or degrade at a pH higher than 5, and more particularly from a pH which ranges from about 5 to 7.5. Some non-limiting examples of suitable pH-sensitive materials include polyacrylamides, phthalate derivatives (i.e., compounds with covalently attached phthalate moieties) such as acid phthalates of carbohydrates, amylose acetate phthalate, cellulose acetate phthalate, other cellulose ester phthalates, cellulose ether phthalates, hydroxypropyl cellulose phthalate, hydroxypropyl ethylcellulose phthalate, hydroxypropyl methyl cellulose phthalate, methyl cellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene and maleic acid copolymers, formalized gelatin, gluten, shellac, salol, keratin, keratin sandarac-tofu, ammoniated shellac, benzophenyl salicylate, cellulose acetate trimellitate, cellulose acetate blended with shellac, hydroxypropylmethyl cellulose acetate succinate, oxidized cellulose, polyacrylic acid derivatives such as acrylic acid and acrylic ester copolymers, methacrylic acid and esters thereof, vinyl acetate and crotonic acid copolymers.

The pH sensitive material may represent less than 50% of the total weight of the body of the GRDF, in embodiments, the pH sensitive material may represent less than 40% of the total weight of the body of the GRDF, in embodiments, the pH sensitive material may represent less than 30% of the total weight of the body of the GRDF, in embodiments, the pH sensitive material may represent less than 20% of the total weight of the body of the GRDF, in embodiments, the pH sensitive material may represent less than 10% of the total weight of the body of the GRDF, in embodiments, the pH sensitive material may represent less than 5% of the total weight of the body of the GRDF.

According to one example, once at least 70% of one or both of inserts 3 have disintegrated or eroded, the individual components of the GRDF 10 detach from each other. In embodiments, the individual components of the GRDF 10 disassemble once 75% of one or both inserts 3 have eroded. In embodiments, the individual components of the GRDF 10 disassemble once 80% of one or both inserts 3 have eroded. Once the inserts 3 have sufficiently disintegrated or eroded, GRDF 10 converts from an expanded configuration, which has a shortest length of greater than 24 mm (for example), to a disassembled configuration including multiple detached components each having a longest length of no more than 12 mm (for example). Each of the detached components of the GRDF is sized to quickly pass through most pyloric valves.

According to one example, during disassembly, the hinge assembly may disengage from at least one arm once a majority of the API is substantially released, i.e., greater than 50% of the API is substantially released. In embodiments, the API may be substantially released from the GRDF after more than 55% of the API is released. In embodiments, the API may be substantially released from the GRDF after more than 60% of the API is released. In embodiments, the API may be substantially released from the GRDF after more than 65% of the API is released. In embodiments, the API may be substantially released from the GRDF after more than 70% of the API is released. In embodiments, the API may be substantially released from the GRDF after more than 75% of the API is released. In embodiments, the API may be substantially released from the GRDF after more than 80% of the API is released. In embodiments, the API may be substantially released from the GRDF after more than 85% of the API is released. In embodiments, the API may be substantially released from the GRDF after more than 90% of the API is released. In embodiments, the API may be substantially released from the GRDF after more than 95% of the API is released.

As mentioned above, the disassembly time of the GRDF 10 can be varied by tailoring the number, size, shape and location of the openings and slots in arms 1 and 2, respectively. For example, positioning opening 19 at the distal end of arm 2 (and omitting slot 18) delays the erosion time of the insert 3 which, in turn, increases the retention time of the GRDF 10 in the stomach since nearly the entire length of the insert 3 must erode before the proximal end of insert 3 (engagement portion 110), which is sandwiched between arm 2 and hinge assembly 4, erodes to a point where the GRDF 10 can no longer remain assembled, i.e., the GRDF loses mechanical integrity. Additional openings and slots in the arm 2 may be added to increase the rate of erosion of the insert 3 if so desired (see FIGS. 33 through 35). It is envisioned that any combination of openings and slots or any combination of differently-sized openings and slots may be utilized to expose more or less surface area of the insert 3. As can be appreciated, the exposed surface area of the insert 3 may affect the overall release rate of the API either as a directly proportional ratio or any envisioned ratio.

It is also envisioned that one opening or slot in arms 1 and 2 may be disposed in registration with the surface area of one API while another opening or slot in arms 1 and 2 may be disposed in registration with a second or different API at a second portion of the insert 3. As can be appreciated, the opening and slots may have different dimensions to control the release rate of the API as the insert erodes. The release rate of the API may be directly proportional to the exposed surface areas of the insert 3, however, the release rate of one API from insert 3 with the same exposed surface area may be different than the release rate of another API from insert 3 with the same exposed surface area. As can be appreciated the polymers, binders and/or excipients used with the API to form the insert 3 may contribute to the release rate. Moreover, different ratios of polymers, binders and/or excipients for the same API may affect the erosion rate of the insert 3 in one arm 1 compared to the erosion rate of the insert 3 in the other arm 2. Alternatively, different ratios of polymers, binders and/or excipients, etc. within a single insert 3 that is compartmentalized with multiple APIs as explained above may be used to affect erosion of the insert 3 and, hence, release of the API(s).

The period of time which the GRDF 10 remains in the stomach after it has expanded is also a function of the erosion rate of the insert 3 or the engaged portion thereof. The insert 3 may be designed to achieve a specific erosion rate using methods which are well known in the art to obtain a desired rate of erosion of insert 3. For example, the insert 3 may contain disintegration agents such as cross-linked sodium carboxymethyl cellulose or sodium starch glycolate to increase the erosion rate, while insert 3 may contain a quantity of binders such as PVP or HPC to decrease the erosion rate. Adjusting the rate of erosion of the insert 3 allows adjustment of the time until release of the GRDF 10 from the stomach, e.g., by modulating the insert release rate, gastric retention may be controlled. Those skilled in the art will recognize how to choose particular excipients to accomplish this purpose.

In embodiments, the size of the GRDF 10 does not deteriorate over time, but rather is dependent on the erosion of insert 3 to initiate disassembly, with the arms 1 and 2 and hinge assembly 4 maintaining their original dimensions.

Figure 2:
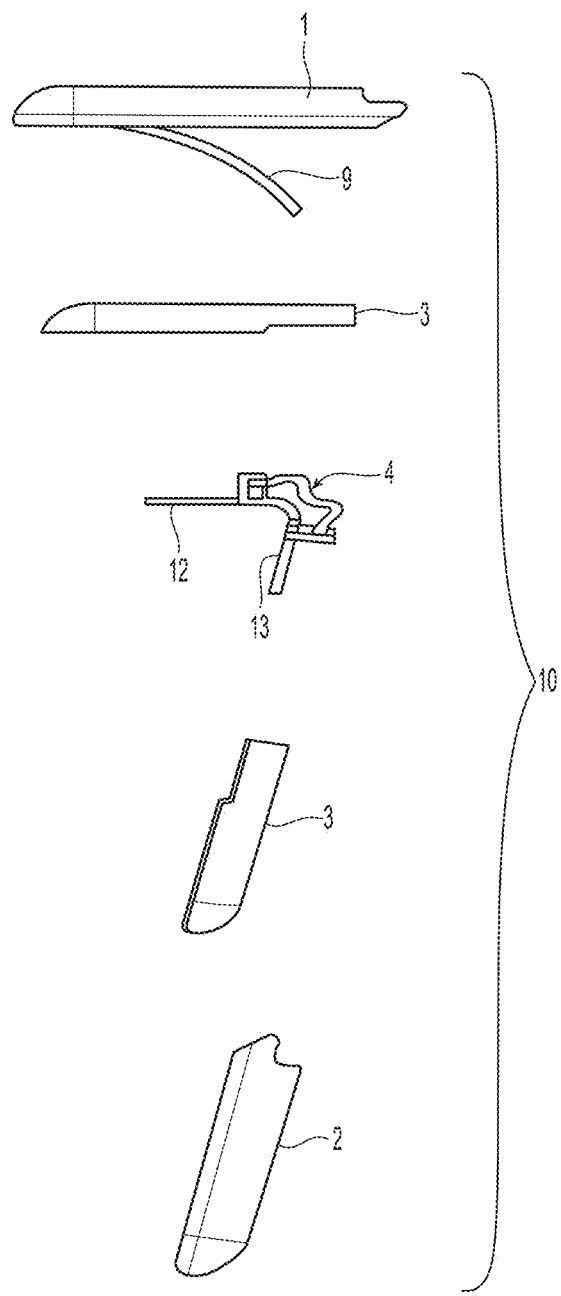
FIG. 2 depicts a side view of the GRDF of FIG. 1 with parts separated.

In addition, the API release time of the GRDF 10 may be relatively slow and constant at least, in part, because inserts 3 are only partially exposed to the gastric environment. More particularly, as shown in FIGS. 1-3, inserts 3 are contained in arms 1 and 2 such that the surface area of each insert 3 is substantially concealed by the respective arms 1 and 2, with the exception of the portion of inserts 3 that are exposed through openings/slot 17, 21 and 18, 19 in arms 1 and 2, respectively. The concealed portion of each insert 3 is not directly exposed to the chemical and mechanical effects in the gastric environment, which typically vary through time. The dissolution rate of the API in the inserts 3, which are substantially concealed by the arms 1 and 2, is not substantially influenced by the gastric environment, especially compared to the release rate of an API provided in dosage form having a surface area that is completely exposed to the gastric environment. Thus, when the GRDF 10 is contained within the stomach, the API is released in the stomach at a relatively slow and constant rate. Moreover, by varying the number of and size of the openings/slot 17, 21, 19 and 18 in the arms 1 and 2, the API may be released in a more controlled fashion for any desired release profile.

As noted previously, once any of the inserts 3 described herein erode past a certain point, the mechanical integrity of any one of the various components described herein (e.g., hinge assemblies, biasing elements, hinge arms, etc.) may be configured to fail resulting in the disassembly of the GRDF 10.

In some embodiments, the controlled-release component of the insert 3 includes a retarding polymer film. In further embodiments, the controlled-release component of the insert 3 includes a retarding polymer film and an additional excipient. In still further embodiments, the additional excipient is a parting agent. In other embodiments, the additional excipient is a pigment. In some embodiments, the retarding polymer film includes at least one polymer or copolymer, such as, but not limited to acrylic acid, acrylic acid derivatives, methacrylic acid, methacrylic acid derivatives, and combinations thereof. In some embodiments, the polymer film includes, but is not limited to: methacrylic acid and methacrylic acid esters, such as, but not limited to, EUDRAGIT® L and EUDRAGIT® S; a copolymer of acrylic and methacrylic acid esters with a small amount of trimethyl ammonium methacrylate such as EUDRAGIT® RL or EUDRAGIT® RS; a copolymer of acrylic acid and methacrylic acid, as well as their esters (ratio of free carboxylic groups to ester groups, e.g., 1:1), such as EUDRAGIT® L30D; or a copolymer made from acrylic acid ethyl and methacrylic acid methyl ester such as EUDRAGIT® NE30D; or combinations thereof. By using these polymers as controlled-release components, a homogenous and safe release rate is achieved.

Figure 8:
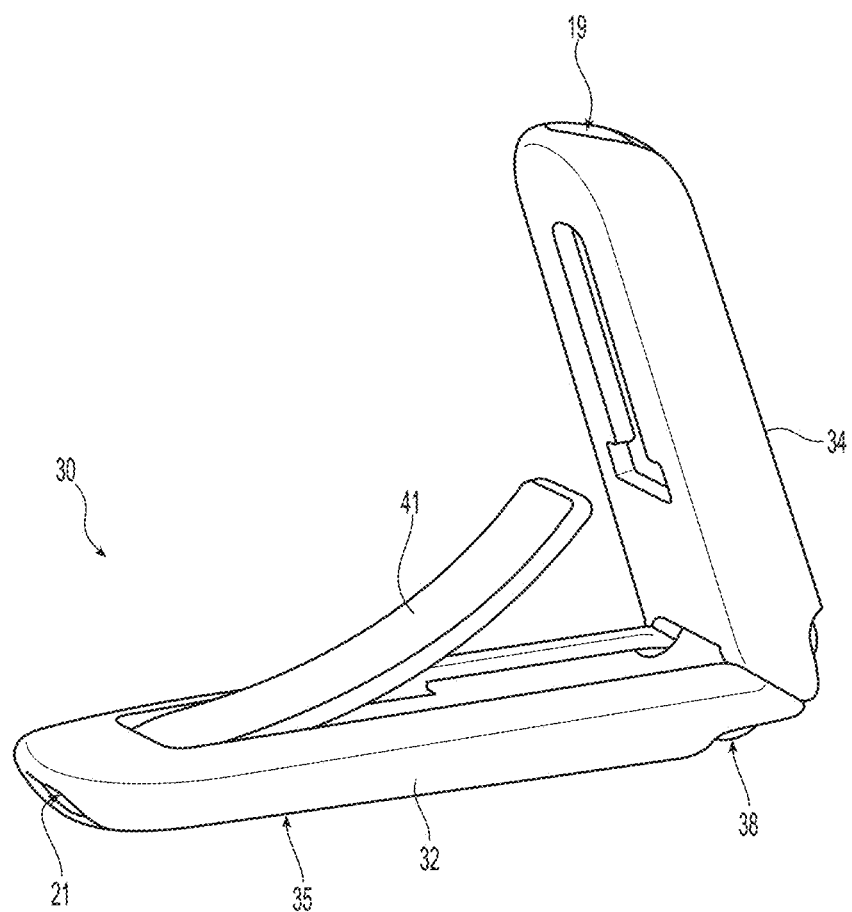
FIG. 8 depicts a perspective view of a GRDF shown in an expanded configuration, according to a second exemplary embodiment of the present disclosure.
Figure 9:
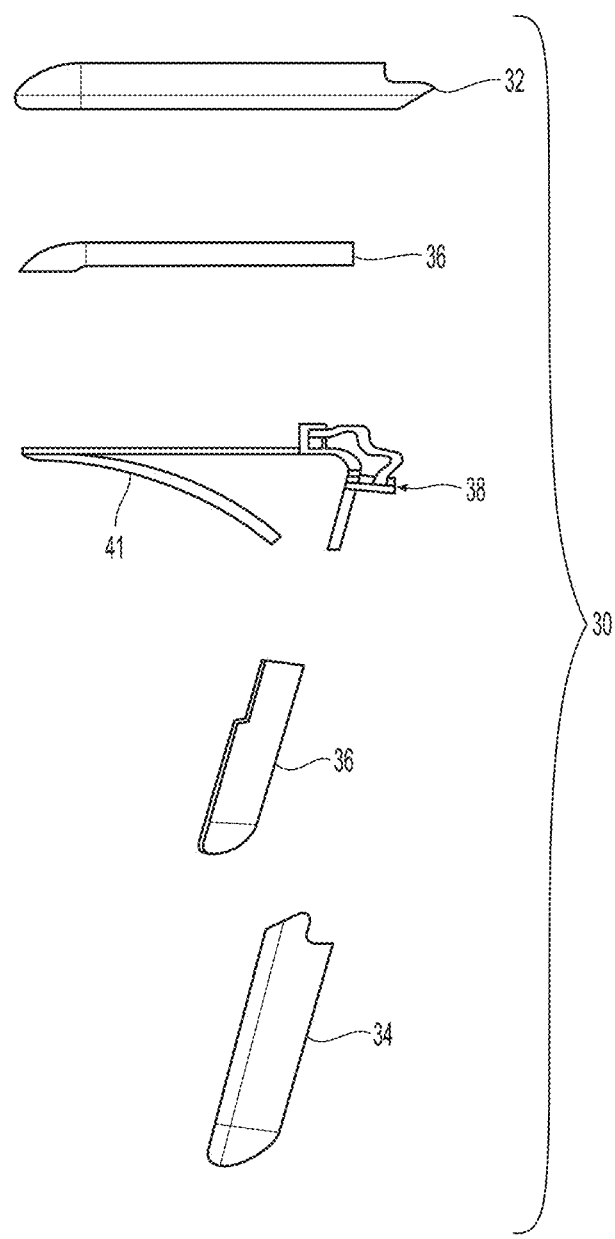
FIG. 9 depicts a side view of the GRDF of FIG. 8 with parts separated.
Figure 10:
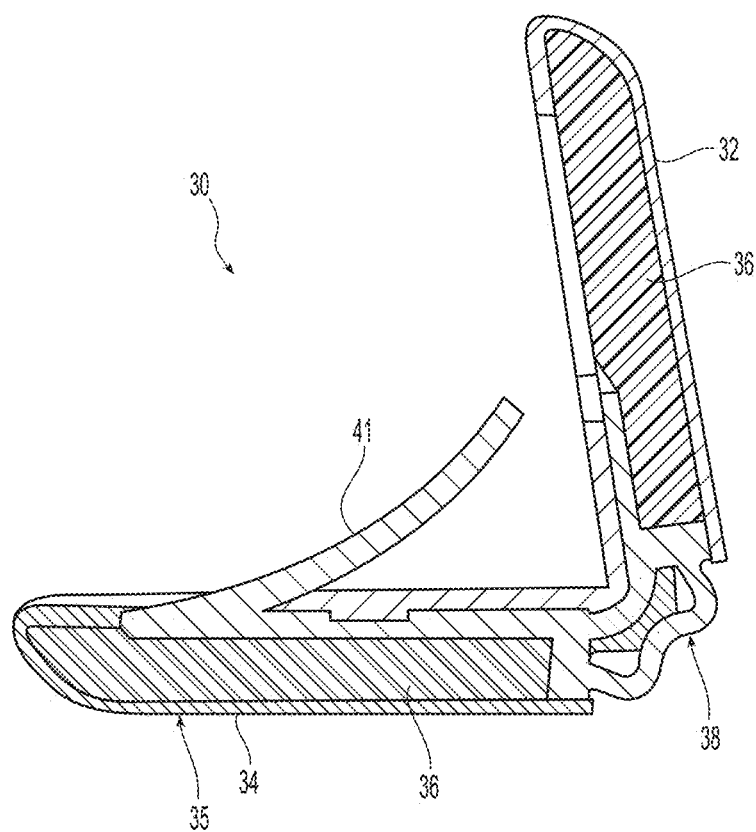
FIG. 10 depicts a cross-sectional view of the GRDF of FIG. 8.
Figure 11:
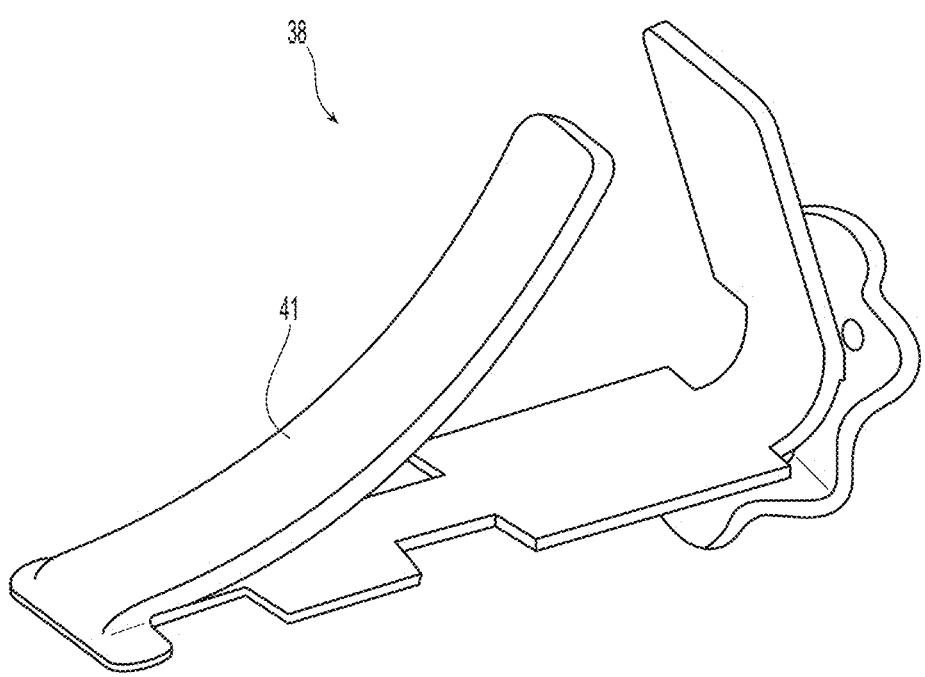
FIG. 11 depicts a perspective view of a hinge of the GRDF of FIG. 8 in an open configuration.
Figure 12:
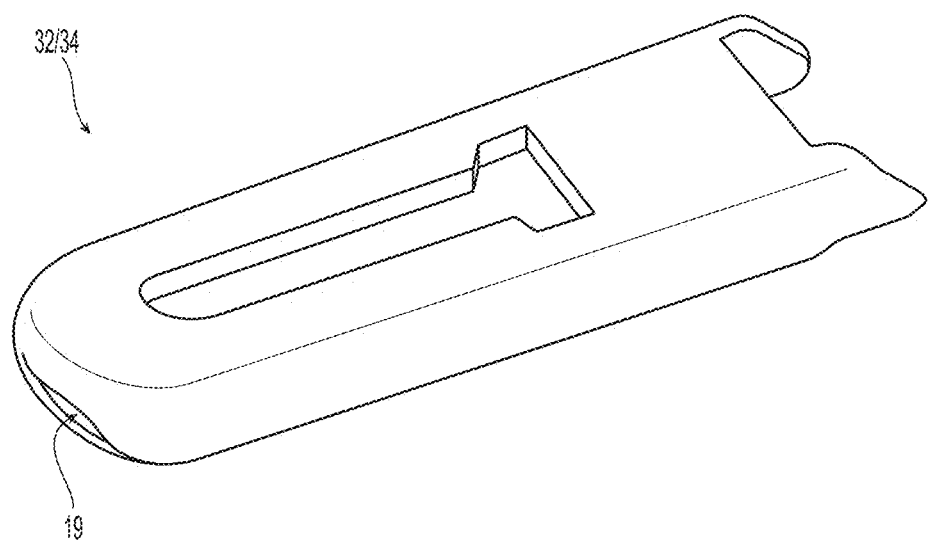
FIG. 12 depicts a perspective view of a second arm of the GRDF of FIG. 8.

FIGS. 8-10 depict another exemplary embodiment of a GRDF, which is denoted by reference numeral 30. GRDF 30 is substantially similar to the GRDF 10 and only the differences between those embodiments will be described. GRDF 30 generally includes a body 35 having two arms 32 and 34, each of which receives an insert 36 comprising an API or a diagnostic. For the purposes herein, GRDF 30 will only be described in terms of its use with an API, however, the advantages noted above with respect to the diagnostic implementations of GRDF 10 equally apply to GRDF 30 as well. Arms 32 and 34, which are also depicted in FIG. 12, may be structurally equivalent and are releasably coupled together by a hinge assembly 38. FIG. 11 depicts a perspective view of the hinge assembly 38. Unlike GRDF 10, GRDF 30 includes a biasing element 41 on the hinge assembly 38, as opposed to on arm 32. Biasing element 41 serves the same purpose as biasing element 9 of GRDF 10, e.g., to separate arms 32 and 34 once the retaining mechanism (e.g., capsule) is removed (e.g., dissolves) so that GRDF 30 can remain in the stomach for a predetermined period of time or until the occurrence of a mechanical event promoting disassembly.

Figure 13:
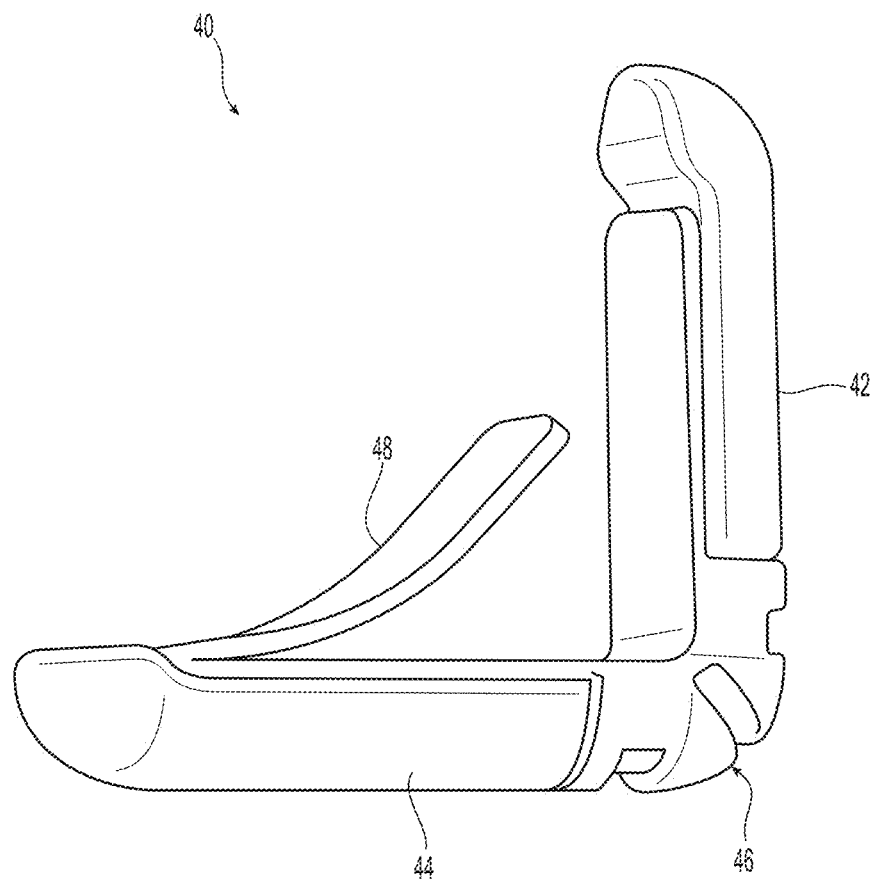
FIG. 13 depicts a perspective view of a GRDF shown in an expanded configuration, according to a third exemplary embodiment of the present disclosure.

FIG. 13 depicts another exemplary embodiment of a GRDF, which is denoted by reference numeral 40. GRDF 40 is substantially similar to GRDF 30 and only the differences between those embodiments will be described. Unlike the previous embodiments, GRDF 40 does not include injection molded arms. In GRDF 40, the inserts 42 and 44, each which are composed of an API, serve as arms. The inserts 42 and 44 are releasably connected together by a hinge assembly 46, which may be injection molded. The hinge assembly 46 includes a biasing element 48 for biasing apart inserts 42 and 44. Hinge assembly 46 conceals at least a portion of the surface area of inserts 42 and 44 so as to slow their dissolution in the stomach. The connection between hinge assembly 46 and inserts 42 and 44 will be described with reference to the similar embodiment shown in FIGS. 14 and 15.

Figure 14:
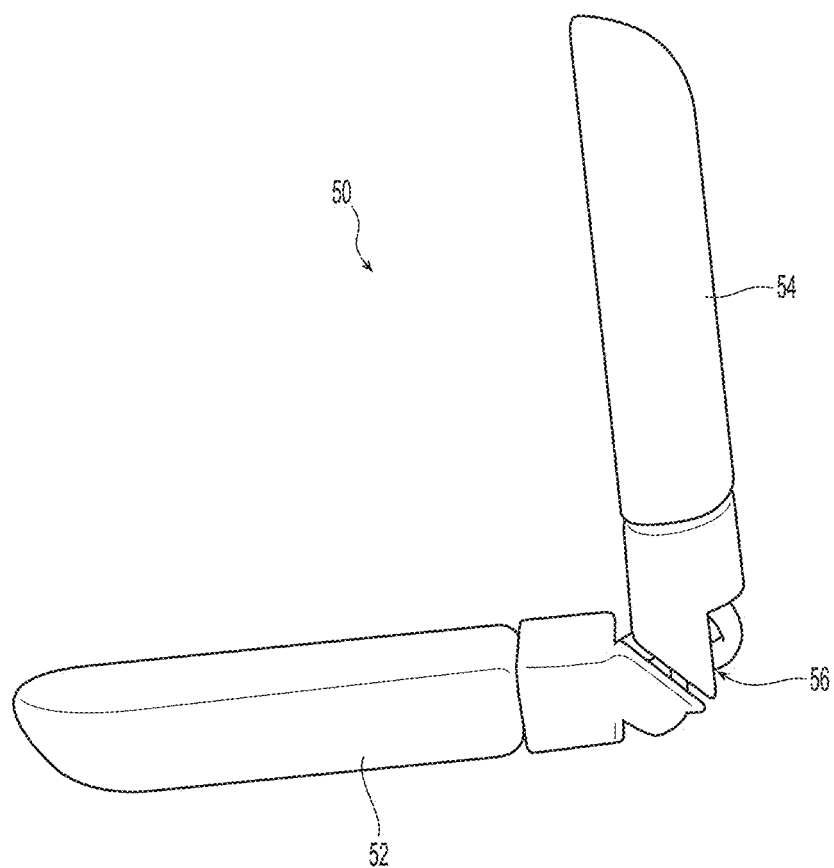
FIG. 14 depicts a perspective view of a GRDF shown in an expanded configuration, according to a fourth exemplary embodiment of the present disclosure.
Figure 15:
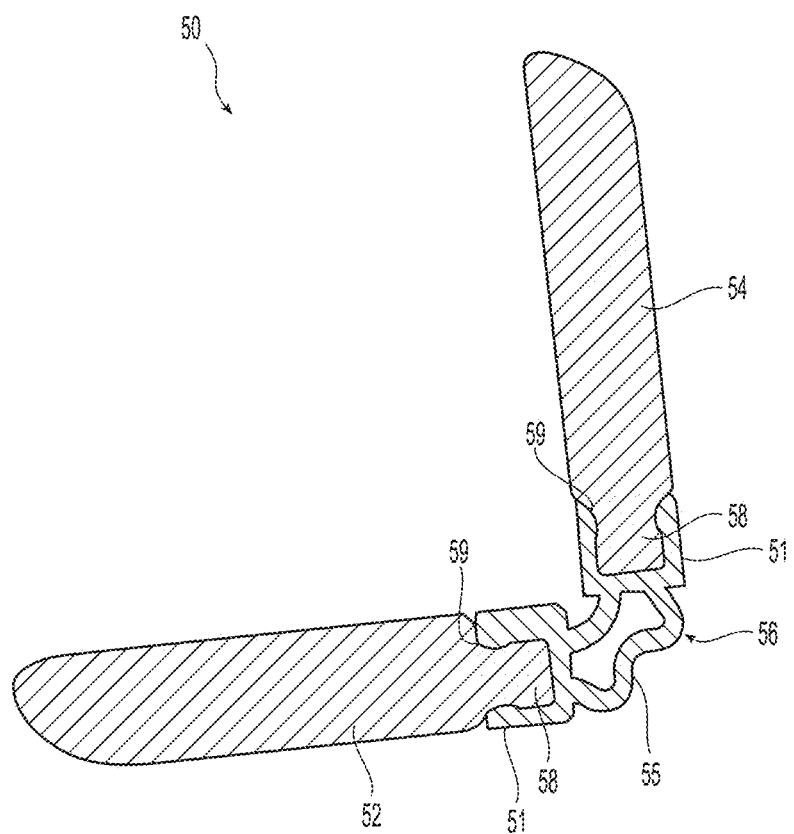
FIG. 15 depicts a cross-sectional view of the GRDF of FIG. 14.

FIGS. 14 and 15 depict yet another exemplary embodiment of a GRDF, which is denoted by reference numeral 50. GRDF 50 is substantially similar to GRDF 40 and only the differences between those embodiments will be described. GRDF 50 includes two inserts 52 and 54, which are generally structurally equivalent, and which are pivotably coupled together by a hinge assembly 56. Hinge assembly 56 includes a shape memory hinge 55 disposed between two engagement portions 51 each having a cavity 59 defined therein for receiving one of the inserts 52 and 54, respectively. As best shown in FIG. 15, each insert 52 and 54 includes a generally bulbous proximal end 58 that is mounted within the complementary-shaped recess 59 defined within each engagement portion 51 of the hinge assembly 56. Although FIG. 15 depicts the inserts including a generally bulbous proximal end 58 and the engagement portions including a complementary-shaped recess 59 on each end of hinge assembly 56, any two complementary-shaped mechanical interfaces may be employed to releasably engage the inserts 52 and 54 with the hinge assembly 56.

Unlike GRDF 40, GRDF 50 does not include a biasing element, such as element 48 of FIG. 13. The hinge assembly 56 of GRDF 50 may be composed of a shape memory material (SMM) such as polylactic acid, shape memory alloy (SMA), or any other shaped memory or polymer that is known to those skilled in the art. Shape memory alloys include copper-zinc-aluminum-nickel, copper-aluminum-nickel, and nickel-titanium, commonly referred to in the art as NITINOL® alloys. The SMM or SMA is configured for two-way shape memory effect. Thus, the SMM or SMA remembers two different shapes, a "cold" shape (e.g., an at-rest position) and a "hot" shape (e.g., an expanded position). Hinge assembly 56 initially may be in an unexpanded position. This unexpanded, or at-rest, position corresponds to the SMM or SMA being in a cold state, that is, the SMM or SMA is in a martensite state. As SMM or SMA "heats up," it eventually reaches an austenite state and begins to transition from the "cold" shape to the "hot" shape, which, in turn, causes hinge assembly 56 to expand. During the austenite phase transition, the hinge assembly 56 continues to expand until it reaches a threshold or final austenite stage. If the SMM or SMA is allowed to cool, the SMM or SMA, as its temperature decreases, will transition from the austenite stage back to the martensite stage such that the SMM or SMA will return to the unexpanded, or at-rest position. In this instance, once the capsule 20 is ingested and erodes/dissolves, the hinge assembly 56 will return to the expanded configuration and the GRDF 50 will expand for retention within the stomach. As can be appreciated, no biasing element is needed to retain the GRDF 50 in the expanded configuration to avoid passage through the pyloric valve until disassembly.

FIG. 16 shows a GRDF, which could be any of the GRDFs 10, 30, 40 or 50 that are described herein, that is encapsulated in the collapsed configuration within one half of a capsule 20. The other half of the capsule has been omitted to reveal the collapsed GRDF 10, 30, 40 or 50. The capsule 20 is configured to maintain the GRDF 10, 30, 40 or 50 in the collapsed and stowed configuration for swallowing. Once ingested, the capsule 20 sufficiently dissolves within the stomach and the GRDF 10, 30, 40 or 50 springs to a deployed and expanded configuration, as described previously. In embodiments, the capsule 20 or other retaining mechanism dissolves or otherwise disengages arms 1 and 2 to permit expansion of the GRDF 10, 30, 40 or 50 to the expanded configuration within 10 minutes of exposure to gastric fluids, in embodiments, within 5 minutes of exposure to gastric fluids, in yet other embodiments, within 2 minutes of exposure to gastric fluids. In embodiments, the GRDF automatically transitions from the collapsed configuration to the expanded configuration for gastric retention in less than 1, 2, 3, 4, 5, 6, 7, 8, 9, or 10 minutes.

Figure 20:
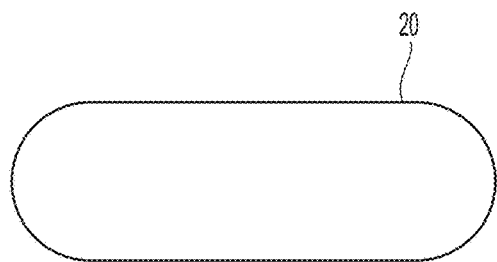
FIG. 20 depicts a side, elevational view of the GRDF of FIG. 17A (or any other disclosed GRDF) stored in a delivery capsule.

FIGS. 17A-17C and 18 depict a GRDF 60 shown in an expanded configuration, according to another exemplary embodiment of the present disclosure. GRDF 60 is substantially similar to GRDF 10 and only the differences between those embodiments will be described. For example, openings 19 and 21 may be defined within respective arms 62 and 64 of the GRDF 60. GRDF 60 includes a body 61 having two arms 62 and 64, each configured to retain an insert 65 (for example, within a cavity defined therein), and a hinge assembly 66 for connecting arms 62 and 64 together in a releasable and pivotable manner. GRDF 60 is capable of moving from a collapsed configuration (FIG. 19) to an expanded configuration (FIG. 17A) by virtue of the spring force of a biasing element 71, As shown in FIG. 20, a collapsed GRDF 60 (FIG. 19) may be encapsulated and packaged in capsule 20.

Figure 17A:
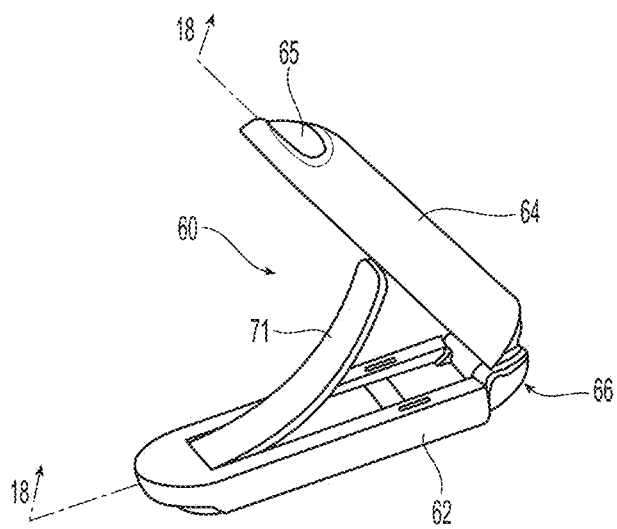
FIGS. 17A-17C depict varying views of a GRDF shown in an expanded configuration, according to a fifth exemplary embodiment of the present disclosure.
Figure 17B:
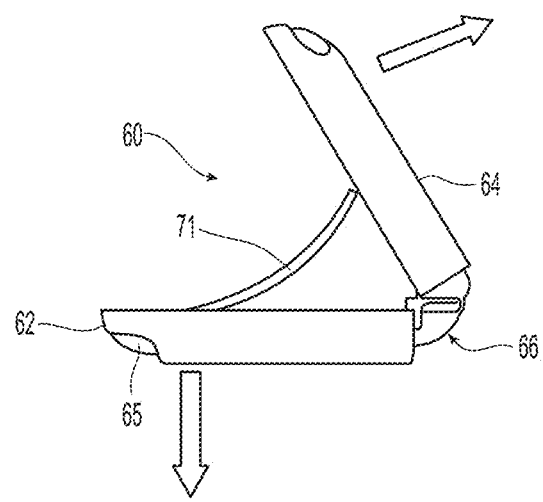
Figure 17C:
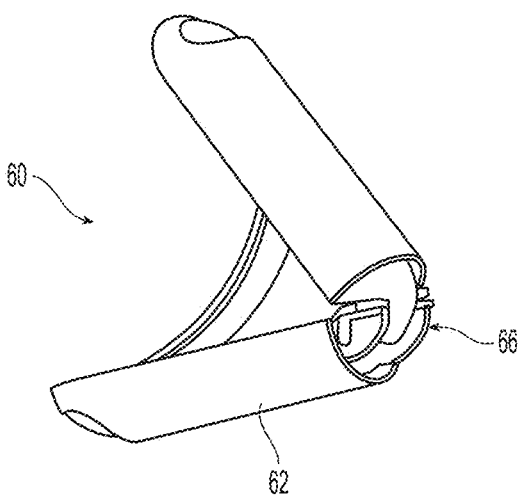
Figure 21:
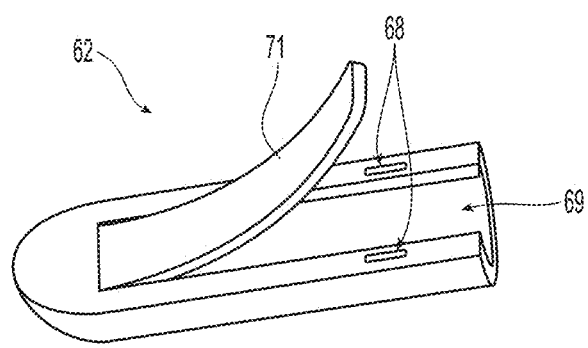
FIG. 21 depicts a perspective view of a first biasing arm of the GRDF of FIG. 17A.

FIG. 21 depicts a perspective view of biasing arm 62 of the GRDF 60 of FIG. 17A. Biasing arm 62, which includes biasing element 71, is substantially similar to arm 1 of FIG. 2 with the exception that arm 62 includes two openings 68 on either side of a rectilinear slot 69 defined within arm 62. Openings 68 are configured to engage corresponding prongs 70 (see FIG. 23A) of hinge assembly 66. Openings 68 are positioned proximal to hinge assembly 66 and on opposing sides of rectilinear slot 69 on a top-facing or inner-facing surface of arm 62 from which biasing element 71 extends. Unlike GRDF 10 of FIG. 1 which relies on friction to releasably connect arm 1 to hinge assembly 4 (e.g., insert 3 of FIG. 1 is sandwiched between hinge arm 12 and inner periphery or wall 27 of cavity 24), arm 62 is connected to hinge assembly 66 by an interference fit created by the engagement between openings 68 and prongs 70.

Figure 22A:
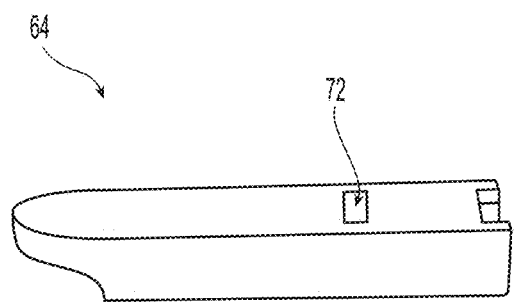
FIGS. 22A and 22B depict varying perspective views of the second arm of the GRDF of FIG. 17A.
Figure 22B:
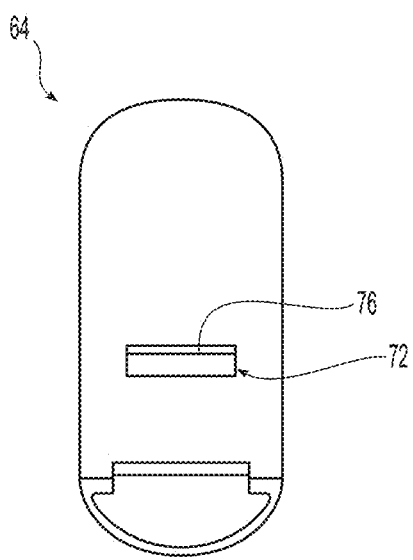

FIGS. 22A and 22B depict perspective views of arm 64 of GRDF 60. Arm 64 is substantially similar to arm 2 of FIG. 2 with the exception that arm 64 includes a narrow transverse slot 72 in lieu of the T-shaped slot 18 disposed along arm 2 of FIG. 7. Unlike T-shaped slot 18, which directly exposes the insert 3 contained within arm 2 to the gastric environment, slot 72 is not configured to expose insert 65 to the gastric environment. Rather, slot 72 releasably engages a prong 74 of hinge assembly 66 (see FIG. 23A). Also, unlike GRDF 10 of FIG. 1 which relies on friction to releasably connect arm 2 to hinge assembly 4 (e.g., insert 3 of FIG. 1 is sandwiched between hinge arm 13 and inner periphery or wall 26 of cavity 25), arm 64 is connected to hinge assembly 66 by an interference fit created by the engagement between slot 72 and prong 74. Slot 72, which may be rectilinear in shape, is positioned proximate to hinge assembly 66.

Figure 18:
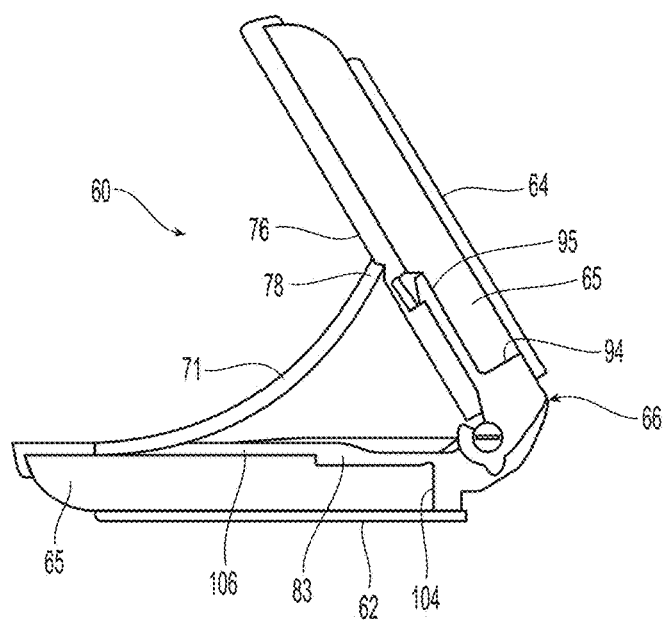
FIG. 18 depicts a cross-sectional view of the GRDF of FIG. 17A taken along line 18-18 of FIG. 17A.
Figure 19:
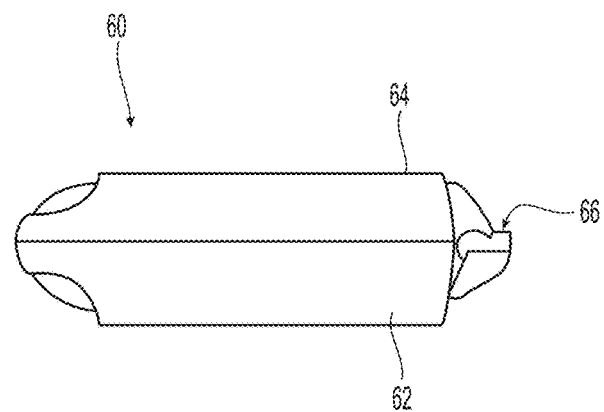
FIG. 19 depicts a side, elevational view of the GRDF of FIG. 17A shown in a collapsed configuration.

As best shown in FIG. 22B, a recess 76 is defined on the outer surface of arm 64 and surrounds slot 72. Recess 76 does not pass through the entire thickness of the top facing or inner facing surface of arm 64. As shown in FIG. 18, in an expanded configuration of the GRDF 60, a distal end 78 of the biasing element 71 engages recess 76 to prevent further movement of the biasing element 71 distally along arm 64. It is envisioned that other known mechanical elements may be employed for this purpose.

FIGS. 23A through 23D depict perspective views of hinge assembly 66 of GRDF 60. Hinge assembly 66 includes a body 75 having two interconnected components, a first or clip portion 80 that pivotably connects to a second or post portion 82. Hinge assembly 66 is shown in a rotated position in FIGS. 23A through 23D, which corresponds to the expanded configuration of the GRDF 60. FIGS. 24A and 24B depict perspective views of the clip portion 80, and FIGS. 25A and 25B depict perspective views of the post portion 82. As explained in further detail below, clip portion 80 and post portion 82 of hinge assembly 66 are mechanically engaged to one another in a clip-like fashion such that clip portion 80 and post portion 82 are capable of pivoting with respect to one another along a limited range of rotation (e.g., 90 degrees or less). Once disposed in the expanded configuration, one or both of clip portion 80 and post portion 82 may include one or more mechanical features (not shown) that prevent clip portion 80 and post portion 82 from returning the hinge assembly 66 and the GRDF 60 to the collapsed configuration.

Referring to FIGS. 24A and 24B, clip portion 80 includes a substantially rectangular body 81 including a C-shaped clip 86 extending perpendicularly from a proximal end thereof and a support rib 99 that extends perpendicularly from the proximal end thereof opposite the clip portion 86. A prong 74 is defined at a distal end of the clip portion 80 and is configured for mechanical engagement with slot 72 of arm 64. Prong 74 is generally configured in the form of a triangular ramp-like surface but any two mechanically interfacing elements are envisioned which will accomplish the same purpose, i.e., engage clip portion 80 to arm 64. For example, prong 74 may be provided on arm 64 and mating slot 72 may be provided on clip portion 80 without departing from the scope of the disclosure. Those skilled in the art will recognize that various mechanisms exist for connecting arm 64 with clip portion 80, such as clamps, clips, barbs, detents, snaps, threads, fasteners and mating surfaces.

The inner peripheral surface of C-shaped clip 86 is sized and configured to mate with a corresponding cylindrical post 90 of post portion 82 (see FIG. 25B). Upon assembly of the two-part hinge assembly 66, C-shaped clip 86 is designed to mechanically engage post 90 in a rotatably locking manner, e.g., C-shaped clip 86 snaps over post 90, The interference fit between C-shaped clip 86 and post 90 retains the two parts of hinge assembly 66 together such that those parts are not readily capable of disconnection.

Figure 23A:
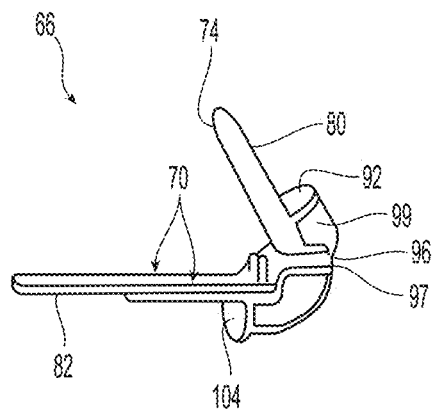
FIGS. 23A through 23D depict varying perspective views of a hinge assembly of the GRDF of FIG. 17A.
Figure 23B:
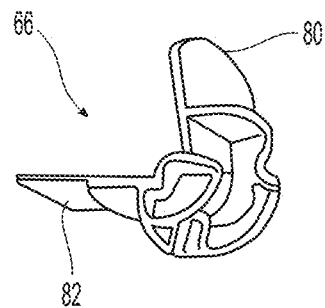
Figure 23C:
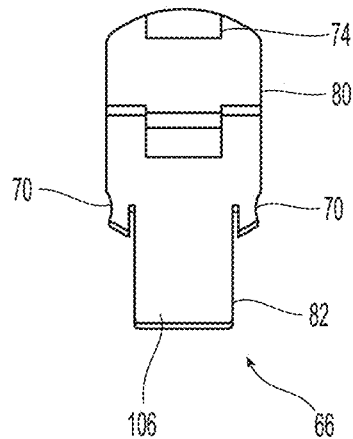
Figure 23D:
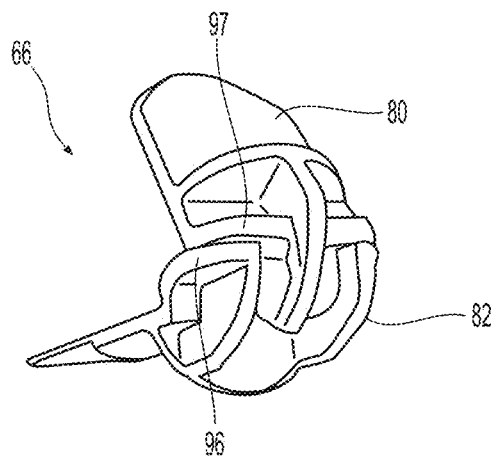

As shown in FIGS. 23A and 24A, support rib 99 includes a semi-cylindrical bearing surface 92 at a distal facing portion thereof (perpendicular to body 81) near the proximal end of clip portion 80. Bearing surface 92 and prong 74 are positioned on opposite sides of body 81. In an assembled form of the GRDF 60, the bearing surface 92 is positioned to abuttingly engage a proximal end 94 of insert 65 (see FIG. 26), and an inner facing surface 81' of body 81 of clip portion 80 (e.g., FIG. 28) is positioned against a planar surface 95 of insert 65.

As best shown in FIGS. 24A and 24B, rotation limiting surfaces 96 are positioned at the proximal end of clip portion 80 and corresponding rotation limiting surfaces 97 are positioned on a proximal end of post portion 82. In an expanded configuration of the GRDF 60, rotation limiting surfaces 96 bear on and abuttingly engage rotation limiting surfaces 97 to prevent over-rotation of clip portion 80 with respect to post portion 82, or vice versa (for example as shown previously in FIG. 17B along the direction of the arrows). Support rib 99 extends between the rotation limiting surfaces 92 and 97 to enhance the structural integrity of clip portion 80.

Referring now to FIGS. 23A through 23D, 25A and 25B, post portion 82 also includes a substantially rectangular body 83. As mentioned above, cylindrical post 90 is provided at the proximal end of body 83 and is configured to engage C-shaped clip 86 of clip portion 80. Post 90 is positioned between a pair of arms 102 that extend perpendicularly from a proximal end of body 83 of post portion 82. Each arm 102 includes the above-described rotation limiting surfaces 97 for limiting relative rotation of the post portion 82 with respect to clip portion 80 along a defined rotational range (e.g., less than 90 degrees).

Figure 31:
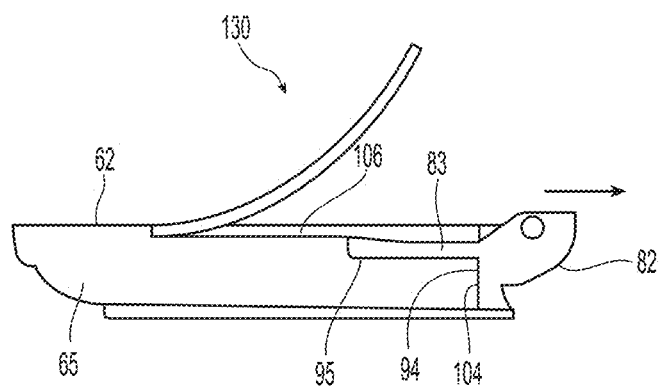
FIG. 31 depicts a side, cross-sectional view of the first biasing arm sub-assembly of FIG. 30 taken along line 31-31 of FIG. 30.

As best shown in FIGS. 18 and 23A, a semi-cylindrical bearing surface 104 is defined near the proximal end of post portion 82 and is configured to extend perpendicularly therefrom. In an assembled form of the GRDF 60, bearing surface 104 is positioned against the proximal end 94 of insert 65 and body 83 is positioned against a planar surface 95 of insert 65 (see FIGS. 26 and 31). A tab 106 at the distal end of body 83 extends over insert 65, as best shown in FIGS. 18 and 31.

Figure 32:
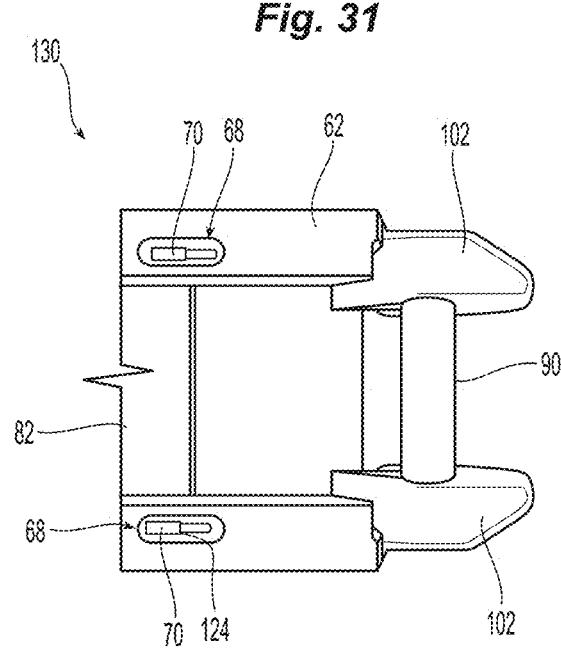
FIG. 32 depicts an enlarged, top perspective of the first biasing arm sub-assembly of FIG. 30.
Figure 33:
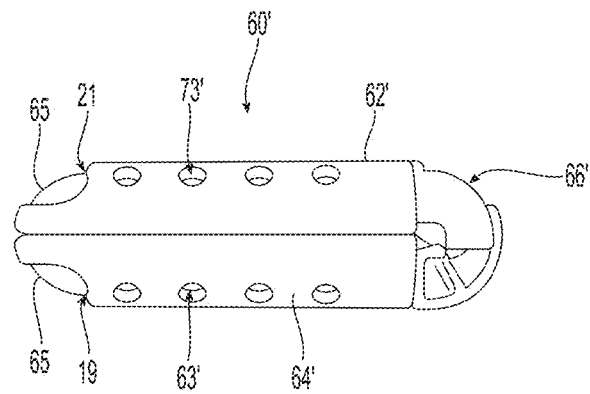
FIG. 33 depicts a side view of a GRDF according to another exemplary embodiment of the present disclosure shown in a collapsed configuration.

As best shown in FIG. 32, prongs 70 (which as mentioned above may be provided in the form of triangular ramp surfaces) are disposed on opposing sides at the center of body 83 for engaging openings 68 of arm 62. Alternatively, prongs 70 may be provided on arm 62 and the openings 68 may be provided on post portion 82 without departing from the scope of the disclosure. Those skilled in the art will recognize that various mechanical interfaces exist for connecting arm 62 with post portion 82, such as clamps, clips, threads, fasteners and mating surfaces.

Bearing surface 104 and prongs 70 are positioned on opposite sides of body 83, A structural support rib 110 (see FIG. 25A) extends between the bearing surface 104 and rotational limiting surfaces 97 to enhance the structural integrity of post portion 82.

Figure 27:
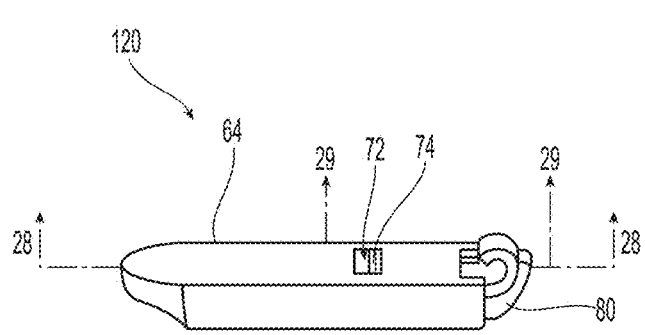
FIG. 27 depicts a top, perspective view of a second arm sub-assembly of the GRDF of FIG. 17A.
Figure 28:
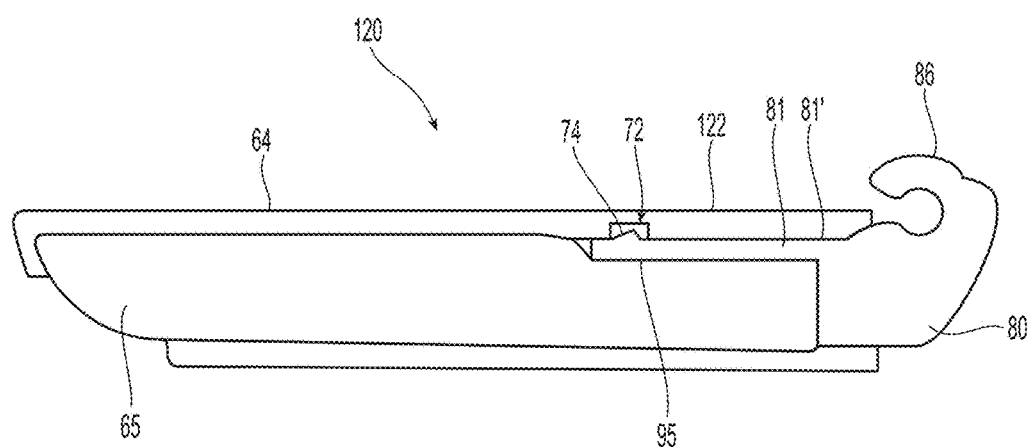
FIG. 28 depicts a side, cross-sectional view of the second arm sub-assembly of FIG. 27 taken along line 28-28 of FIG. 27.
Figure 29:
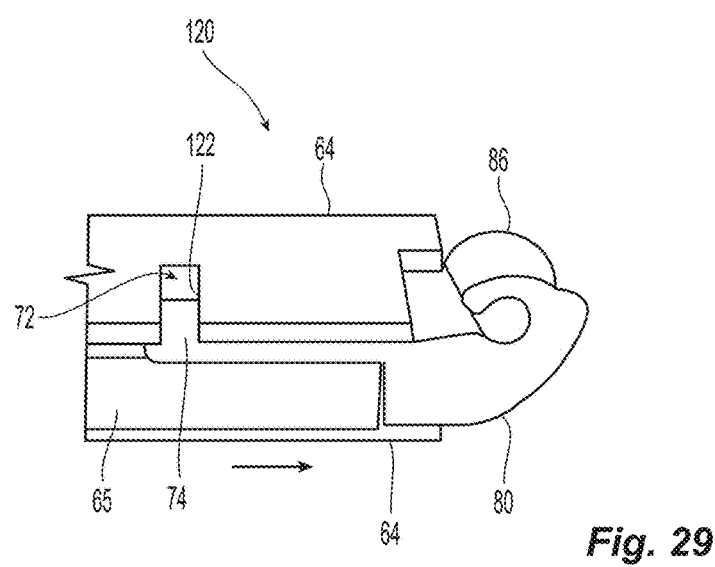
FIG. 29 depicts an enlarged, cross sectional view of the second arm sub-assembly of FIG. 27 taken along line 29-29 of FIG. 27.

FIGS. 27 through 29 depict an arm sub-assembly 120 of the GRDF 60 including arm 64, clip portion 80 and an insert 65 in an assembled configuration. The arm sub-assembly 120 is configured to mechanically engage a corresponding arm sub-assembly 130 including arm 62, post portion 82 and a second insert 65 (see FIGS. 30-32).

As best shown in FIG. 29, clip portion 80 is sandwiched between an inner peripheral surface of arm 64 and insert 65 of arm sub-assembly 120. A planar surface 122 of prong 74 is positioned against a side surface of slot 72 such that prong 74 cannot translate in the proximal direction (see arrow in FIG. 29) out of slot 72 unless and until insert 65 is sufficiently eroded. More particularly, once insert 65 has sufficiently eroded, the friction between arm 64, clip portion 80 and insert 65 is alleviated, such that those parts can detach from each other. In this manner, the insert 65 maintains the mechanical integrity of the engagement between the clip portion 80 and the arm 64 such that, once eroded, this mechanical integrity fails and the clip portion 80 and arm 64 automatically disengage from one another, As best shown in FIG. 28, to assemble arm sub-assembly 120, insert 65 is first positioned through the opening at the proximal end of arm 64 until the distal end of insert 65 bears on the semi-spherical surface at the end of the opening of arm 64, As mentioned above, the insert 65 and the inner peripheral surface of the arm 64 include complementary geometries (e.g., semi-cylindrical surfaces) to facilitate assembly although non-complementary geometries are also envisioned depending upon a particular purpose. The distal end of clip portion 80 is then inserted into the narrow space defined between insert 65 and the inner periphery or inner wall of arm 64. The inner periphery of arm 64 (which includes slot 72 defined therein) flexes to a small degree as the prong 74 of clip portion 80 slides distally along the inner periphery of arm 64 until prong 74 engages (seats within) slot 72, as shown. Once properly engaged, prong 74 prevents clip portion 80 from moving in a proximal direction as mentioned above (see arrow in FIG. 29).

Figure 30:
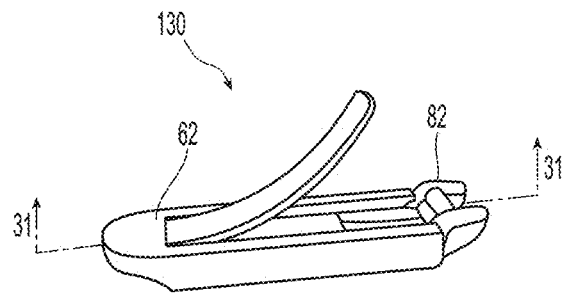
FIG. 30 depicts a perspective view of a first biasing arm sub-assembly of the GRDF of FIG. 17A.

FIGS. 30 through 32 depict arm sub-assembly 130 including arm 62, post portion 82 and a second insert 65. Post portion 82 is sandwiched between an inner periphery of arm 62 and second insert 65. A planar surface 124 of each prong 70 is positioned against a side surface of opening 68 such that prongs 70 cannot translate in the proximal direction (see arrow in FIG. 31) out of openings 68 unless and until second insert 65 is sufficiently eroded. More particularly, upon erosion of second insert 65, the friction between arm 62, post portion 82 and second insert 65 is alleviated, such that those parts can detach from each other in the stomach, Similar to arm sub-assembly 120 described above, the second insert 65 maintains the mechanical integrity of the engagement between the post portion 82 and the arm 62 such that, once eroded, this mechanical integrity fails and the post portion 82 and arm 62 automatically disengage from one another.

As best shown in FIGS. 31 and 32, to assemble arm sub-assembly 130, second insert 65 is first positioned through an opening at the proximal end of arm 62 until the distal end of second insert 65 bears on the interior semi-spherical surface at the end of the opening of arm 62. As mentioned above, the second insert 65 and the inner peripheral surface of the arm 62 include complementary geometries (e.g., semi-cylindrical surfaces) to facilitate assembly although non-complementary geometries are also envisioned depending upon a particular purpose. The distal end of post portion 82 is then inserted into the narrow space defined between second insert 65 and the inner periphery or inner wall of arm 62, The inner periphery of arm 62 (which includes openings 68 defined therein) flexes to a small degree as the prongs 70 slide distally along the inner periphery of arm 62 to eventually engage (seat within) respective openings 68, as shown. Once properly engaged, prongs 70 prevent post portion 82 from moving in a proximal direction (see arrow in FIG. 31) with respect to arm 62.

Once arm sub-assemblies 120 and 130 are assembled they are connected together by engaging (e.g., snap-fitting) C-shaped clip 86 onto post 90. The GRDF 60 is then moved to a collapsed configuration and covered with capsule 20 or otherwise releasably contained in a collapsed condition as described above. The GRDF 60 is then ready to be swallowed by a user.

FIGS. 33 through 36B depict a GRDF 60' according to another exemplary embodiment of the present disclosure. GRDF 60' is substantially similar to GRDF 60 and only the differences between those embodiments will be described. Similar to GRDF 60, GRDF 60' includes opposing arms 62' and 64' that are configured to pivot about hinge assembly 66' from a first collapsed configuration (FIG. 33) to a second expanded configuration (FIGS. 34*a* and 34B). Opposing arms 62' and 64' include a plurality of openings 73' and 63', respectively, defined therethrough configured to expose insert 65. As mentioned above, any combination of openings may be utilized to control the erosion rate of the insert(s) 65. Arm 62' may include one or more openings e.g., openings 73' and opening 21 at a distal end thereof, defined therethrough and positioned therealong and arm 64' may include one or more openings e.g., openings 63' and opening 19 at a distal end thereof, defined therethrough and positioned therealong. As can be appreciated, the number of openings and the position of the openings along the arms 62' and 64' may vary.

Figure 34A:
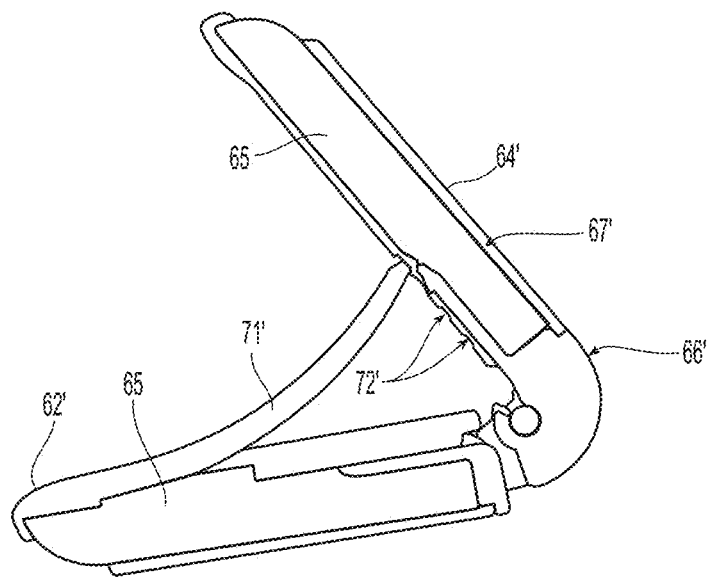
FIGS. 34A and 34B depict varying views of the GRDF of GIF. 33 disposed in an expanded configuration.
Figure 34B:
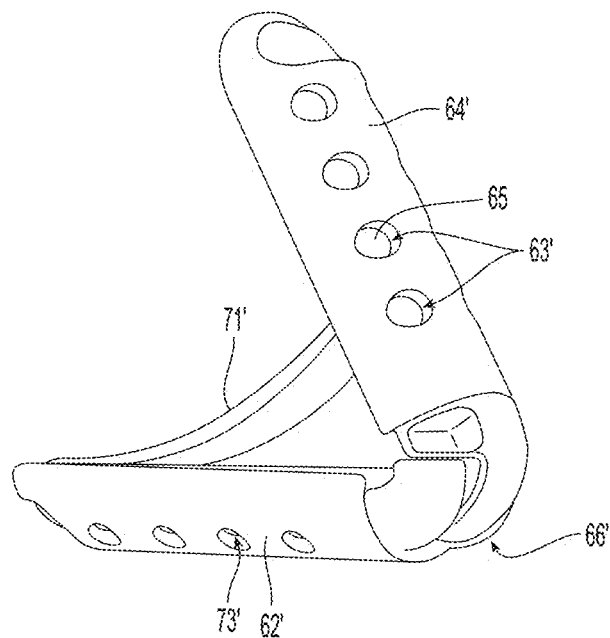

As best shown in FIGS. 34A and 34B, a biasing element 71' is included that is configured to release the GRDF 60' to the expanded configuration (e.g., once the retention element is eroded (capsule 20 is dissolved)). Similar to the embodiments described above with respect to FIGS. 1-16, biasing element 71' may act to lock the GRDF 60' in the expanded configuration until disassembly (or, alternatively, be configured to prevent the GRDF 60' from returning to the collapsed configuration). As such, once expanded, the distal end of biasing element 71' may be configured to engage one of a series of recesses or slots 72' defined within arm 64'. Once engaged, arm 64' is prevented from pivoting towards arm 62' until disassembly.

Figure 35:
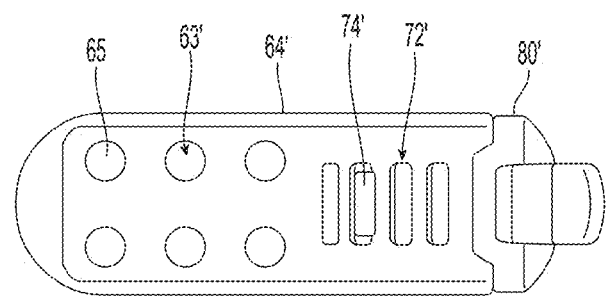
FIG. 35 depicts a top view of one arm of the GRDF of FIG. including a plurality of openings and engagement slots disposed therein.

As best shown in FIG. 35, recesses or slots 72' are also configured to receive prong 74' of clip portion 80' to releasably engage the clip portion 80' to the arm 64' as described in detail above with respect to FIGS. 1-33. It is envisioned that providing a plurality of recesses or slots 72' along the proximal end of the arm 64' may allow the clip portion 80' to engage the arm 64' at varying positions which, in turn, allows varyingly-sized inserts 65 to be utilized within cavity 67'. Varying the size the inserts 65 utilized within one or both arms 62' and 64' gives the manufacturer additional flexibility as far as dosage forms and API delivery while utilizing the same arms 62' and 64' and hinge assembly 66'.

Figure 36A:
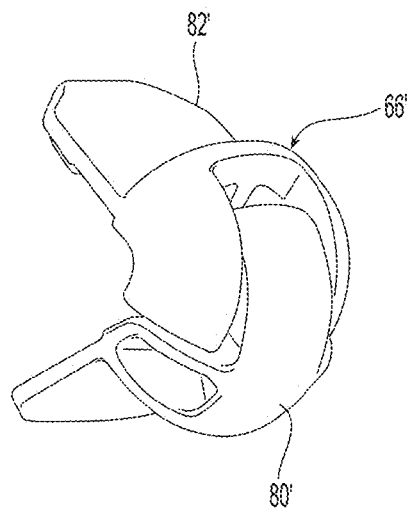
FIGS. 36A and 36B depict varying views of a hinge assembly in an assembled configuration.
Figure 36B:
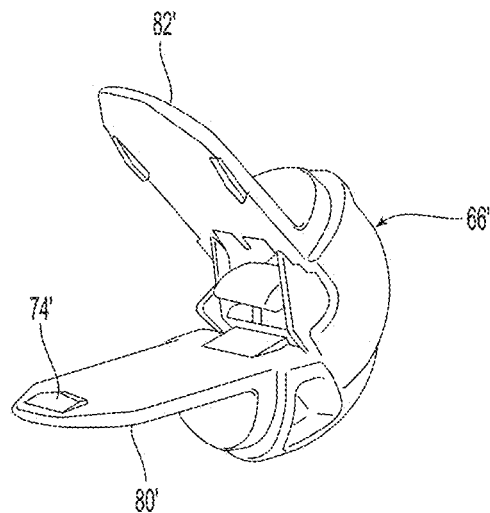

FIGS. 36A and 36B show varying views of the hinge assembly 66' including C-shaped clip portion 80' and post portion 82'. Hinge assembly 66' is configured to operate in a similar manner as described above with respect to FIGS. 17-33 and includes similar features.

Referring generally to the figures, it should be understood that any method or mechanism that is configured to maintain the collapsed configuration of the GRDF prior to swallowing is envisioned. Several different embodiments have been described above and include a capsule 20 that erodes or dissolves upon contact with gastric fluid. In another envisioned embodiment, in a case where the natural state of the GRDF is open (natural or biased configuration of one of the hinge assemblies described herein is open to expand the GRDF), there may be a material holding the GRDF closed which dissolves or erodes in the presence of gastric fluid thereby releasing the GRDF to an expanded configuration. In another embodiment, the material may be in the shape of an erodible band which encompasses the arms to maintain the GRDF in a collapsed configuration until the band erodes allowing expansion of the GRDF. Still another envisioned embodiment includes a glue-like material that keeps the two arms together until the glue-like material erodes allowing expansion of the GRDF. Another option may be the capsule itself which maintains the closed state. In embodiment, the capsule maintains a shelf life durability or shelf life stability for more than 2 years under accelerated conditions.

It should be understood that any method or mechanism that is configured to transition or open the GRDF to the expanded configuration is encompassed by the present disclosure. In one envisioned embodiment, a superporous hydrogel system may be incorporated into the inner part of the arms which expands upon exposure to the gastric environment thereby forcing the two arms apart and to the expanded configuration. In another embodiment, a leaf spring (similar to those described above) springs outwards and extends from the inner area of one or both of the arms once the expanding configuration is initiated or once the mechanical integrity of the collapsed condition has been compromised, e.g., capsule 20 is dissolved. In other embodiments, various mechanisms may be employed to lock the arms in an expanded configuration until the insert has sufficiently erodes to disassemble the GRDF. For example, as described above, an inner facing surface of one of the arms may include a locking mechanism to lock the leaf spring in place in the expanded configuration. Alternatively and in addition to the hinge assemblies described above, the hinge assembly may include one or more mechanical interfaces or mechanisms, gear, spring, cam, etc. that are configured to maintain or lock the GRDF in an expanded configuration until disassembly. The leaf spring may simply be configured to bias the GRDF from the collapsed configuration and not necessarily lock to maintain the GRDF in the expanded configuration but may be configured to simply prevent the GRDF from transitioning back to the collapsed configuration.

In embodiments described herein, the leaf spring or biasing mechanism 9 may be configured to lock the two arms in the expanded configuration until disassembly. One or more locking mechanisms may be employed for this purpose, or, alternatively, the leaf spring may be configured to engaged one of the arms to keep the two arms apart until disassembly. In other embodiments, the biasing mechanism, e.g., leaf spring 9, may be configured to engage the opposing arm 2 to keep the two arms 1 and 2 separated as the insert 3 slowly erodes. As the insert 3 erodes (API is released), the bias of the leaf spring 9 gradually lessens or the leaf spring 9 regresses into the arm 2 such that the angle $\beta$ between the two arms 1 and 2 lessens to a point when the size or formation (e.g., triangular shape) of the GRDF 10 is small enough to pass through the pyloric valve in the stomach. As can be appreciated, in this instance the GRDF does not necessarily need to disassembly for it to safely pass through the pyloric valve.

As noted above, after a pre-determined period of time, the GRDFs described herein will eventually lose their mechanical integrity as a single unit, disassemble and pass from the stomach for subsequent evacuation. There are many possible mechanisms to achieve this result, all of which are encompassed by the present disclosure. Non-limiting examples include:

- Hinge assemblies or other connection mechanisms composed of one or more base-sensitive materials which begin to disintegrate or erode once exposed to the proximal end of the arm's internal matrix (the API release system) which includes basic material.
- Hinge assemblies or other connection mechanisms composed of one or more time sensitive polymers which begin to disintegrate at a certain point in time.
- Hinge assemblies or other connection mechanisms connected to the arms in a certain mechanical fashion, with a certain mechanical shape or by one or more mechanical features such that once the arms, insert or hinge assembly erode via the introduction of gastric fluids, the mechanical integrity of the hinge assembly or arms (or parts thereof) is compromised due to a change of shape of one or more mechanical elements and, as a result, the mechanical engagement is lost.

Optionally, in an additional embodiment, any of the GRDFs described or envisioned herein may include an emergency release feature that allows the GRDF to pass through the pyloric valve for immediate removal from the stomach and gastrointestinal tract, if needed. An antidote or other triggering mechanism may be employed to initiate the emergency release of the GRDF. In one envisioned embodiment, the GRDF includes a hinge assembly (or any other portion thereof) that is pH sensitive (for example sensitive to a pH 5-5.5) such that under normal gastric conditions the hinge assembly (or any portion thereof) remains intact and the GRDF functions as intended. However, if needed, the environmental pH can be slightly increased (to within the above pH sensitive range or any other specified range) causing the mechanical integrity of the hinge assembly (or any portion thereof) to erode causing the hinge assembly to disassemble from one or both arms and pass through the pyloric valve for subsequent evacuation. For example, the erosion may cause reduced mechanical pressure between the insert and the hinge assembly (or a portion thereof) to eventually release the hinge assembly from one or both arm(s) and pass from the stomach.

As mentioned above, the GRDF may be configured for use with one or more additional APIs with different release profiles, e.g., an additional API designed for immediate release. The additional API, (e.g., an API designed for immediate release) may be located at the distal end of the insert and used with a GRDF with an opening at a distal end of one or both arms. In this instance, the configuration of the GRDF along with the API being disposed at a distal end of the insert directs the initial infusion of gastric fluids into the distal opening of the one or both arms and into immediate contact with the additional API promoting immediate release. In another embodiment, additional API may be included as a layer encompassing the capsule or surrounding the GRDF, or a layer encompassing one or both arms (or portions thereof). In embodiments, the amount of API in the GRDF is a therapeutically effective amount for treating a particular disease or condition over a prescribed time period, e.g., hourly (q1h), q2h-q8h, b.d.s., and o.d.

Any relevant amount of API is encompassed by the present disclosure. The amount of API depends on a variety of factors such as the need for additional excipients and the size of tablet. In embodiments, an amount of API contained in the GRDF may be from about 0.1 mg to about 2 grams, in embodiments from about 10 mg to about 1.8 grams. In other embodiments, the amount of API present in the insert may be an amount greater than 400 mg, 600 mg, 800 mg, 1000 mg, or 1500 mg. In embodiments, the API is in an amount of about 500 mg to about 1.5 grams.

The GRDFs described herein may include a body which includes a volume ranging from about 100 mm$^3$ to about 2000 mm$^3$. In embodiments, the volume of the body may range from about 200 mm$^3$ to about 1800 mm$^3$. In embodiments, the volume of the body may range from about 500 mm$^3$ to about 1500 mm$^3$. In embodiments, the volume of the body may range from about 800 mm$^3$ to about 1200 mm$^3$. In embodiments, the volume of the body may be about 950 mm$^3$.

The GRDFs described herein are designed to maximize the API to total excipients volume/weight ratio, in an effort to maximize the drug volume/weight load to be processed in the stomach while minimizing the volume of non-drug material that must pass through the gastrointestinal tract. According to one aspect of the disclosure, a ratio of a weight of the active pharmaceutical ingredients to a weight of total excipients is from about 0.8 to about 0.05, in embodiments, from about 0.7 to about 0.3, and in other embodiment, from about 0.6 to about 0.4. The total excipients may include the arms, the hinge, the excipients in the insert, and the capsule. In embodiments, the load of the excipients may be from about 500 mg to about 2000 mg, and the drug volume may be from about 900 mg to about 1000 mg.

The GRDFs described herein are designed to maximize the API to total excipients ratio, in an effort to maximize the drug API load (mg) while minimizing the load of non-drug material (mg) that must pass through the gastrointestinal tract. According to one aspect of the disclosure, the ratio of a load (mg) of the active pharmaceutical ingredients to a load of total load of the insert tablet (excipients+API) in the insert is from about 0.1 to about 0.99, in embodiments, from about 0.5 to about 0.95, and in other embodiments from about 0.7 to about 0.9.

One or more APIs or diagnostics for controlled release may be associated with the GRDF in a variety of ways, depending on the physical and chemical properties of the API or diagnostic and the desired release profile. In one example, the API or diagnostic may be at least partially enclosed within an external polymeric layer which forms the perimeter of the arm(s) and which at least partially defines an interior cavity configured to hold a API/diagnostic and excipients. The API/diagnostic and excipients may be contained within the polymeric layer forming the cavity. The excipients may be any pharmaceutically excipients including, but not limited to, an erodible polymer matrix or may make up a constant-flow pump, which is for example mechanically or osmotically driven. As described above, the cavity may also have openings which contribute to a controlled release effect. In another example, the controlled release effect may be achieved by another method known in the art other than a polymeric layer forming a shell. As mentioned above, the arms may also be rigid and contain API (or API and excipients). In embodiments, the API may not be contained within an insert but may, for example, the API may be formulated to simply form part of the arm itself. Similar to the various embodiments described herein, the insert can be disengaged from the arms in any a number of different ways, e.g., an erodible polymer linking the arms to the hinge that disengages the arms in a time dependent manner.

Each of the GRDFs described above provides mechanical strength and is capable of resisting forces applied by the stomach under both fed and fasted condition. The mechanical strength is sufficient to enable, upon expansion of the GRDF, the preservation of the expanded configuration to provide gastric retention. More specifically, there is provided a GRDF with collapsed and expanded configurations which resists mechanical gastric forces.

The choice of materials for GRDFs includes all materials that will maintain stability in the gastric environment and provide enough rigidity to prevent disassembly or disintegration prior to the desired time (preferably through fasted and fed states). Any acceptable pharmaceutically approved polymeric materials such as cellulose acetate, ethocel, eudragit, or hydroxypropyl cellulose acetate succinate, with or without addition of a plactisizer, can be used for preparation of the GRDF. If the desire is a non-biodegradable formulation, one may provide, for example, a cellulose ester with plasticizer. Suitable cellulose esters include for example: cellulose acetate, cellulose acetate butyrate and cellulose acetate propionate. Non-limiting examples of suitable plasticizers include, for example, dibutyl sebacate, triacetin, triethyl-citrate, acetyl tributyl citrate, acetyl triethyl citrate polyethylene glycol, polyethylene glycol monomethyl ether, glycerin, sorbitol sorbitan solutions, castor oil, diacetylated monoglycerides, triethyl citrate, tributyl citrate or others.

The materials are selected and processed in a way that will enable each of the components of the GRDF to operate according to its defined functionality (e.g., rigidity for the arms and hinge, elasticity of spring, and stability in dissolution, as defined above). Different materials may be used in order to better balance between durability and safety or eventual disintegration; pH independence and dependence, etc. For example, the ratio of cellulose acetate (CA) to triacetin may contribute to the durability, elasticity, reduced brittleness, independence from pH changes and decreased erodability. In embodiments, the cellulose acetate (CA) to triacetin ratio is 3:1 to 10:1, or in other embodiments 4:1 to 8:1.

In embodiments, the pharmaceutically acceptable material may include a composition which includes a cellulose ester and a plasticizer in a ratio ranging from about 3:1 to about 8:1, in embodiments, from about 4:1 to about 6:1, and in particular embodiments 4:1.

In embodiments, the hinge assembly and or arms may be comprised of: plasticizer and any one or more of the following: cellulose ester, HPMC acetate succinate, ethocel or eudragit. The plasticizer may be any one or more of the following: trethyl citrate, PEG 3350, triacetin and triethyl citrate. More specifically, the cellulose ester may be cellulose acetate (CA). The polymer to cellulose acetate (CA) ratio may be from about 3:1 to about 10:1, or in other embodiments from about 4:1 to about 8:1. Dibutyl Sebacate, Triacetin, Triethyl-citrate, Acetyl Tributyl Citrate, Acetyl Triethyl Citrate Polyethylene glycol, Polyethylene Glycol Monomethyl Ether, Glycerin, Sorbitol Sorbitan Solutions, Castor Oil, Diacetylated Monoglycerides, Triethyl Citrate, Tributyl Citrate.

In embodiments, the GRDF including any of the components of the GRDF, i.e., the body, arms, hinge assembly, etc., may include more than about 200 mg, 400 mg, 600 mg, 700 mg, or 750 mg of the cellulose ester per unit dosage form. In other embodiments, the GRDF including any of the components of the GRDF, i.e., the body, arms, hinge assembly, etc., may include from about 100 mg to about 800 mg of the cellulose ester per unit dosage form.

In embodiments, the GRDF including any of the components of the GRDF, i.e., the body, arms, hinge assembly, etc., may include more than 50 mg, 100 mg, 150 mg, 180 mg, 190 mg of the plasticizer per unit dosage form. In other embodiments, the GRDF including any of the components of the GRDF, i.e., the body, arms, hinge assembly, etc., may include from about 25 mg to about 250 mg of the plasticizer per unit dosage form.

The gastric retention may be attained due to the arms and hinge assembly, while the structure of the arms (with slight modifications of formulation of the insert depending on length of time needed) provide for the controlled release of the API or diagnostic.

The GRDFs may be manufactured by a number of processes including injection molding 3D printing and the like, as will be clear to one skilled in the art, such as the manufacturing techniques described in WO 2003057197 or in Zema et. al., Journal of Controlled Release, Volume 159 (2012) 324-331. For example, a mold can be constructed in the desired shape of the GRDF and filled with appropriate material(s) in liquid state and then allowed to cure by chemical processes or cooled if thermosetting material(s) are used. The GRDFs described herein or any parts thereof, e.g., arms, hinge assembly, springs, etc. may be made from pharmaceutically acceptable materials or ingredients, e.g., one or more ingredients listed in the IIG guidelines. In embodiments, the GRDF may include a body which is made from at least one pharmaceutically acceptable material wherein the size, shape, and durability of the body are maintained while in the stomach for a predetermined time period of gastric retention. The use of injection molding applied to the specified ingredients in the specified molds resulted in less than 10% variation, in embodiments, less than 5% variation, in detail as small as 500 μm.

In embodiments, the GRDF, including any of the components of the GRDF, i.e., the body, arms, hinge assembly, etc., may include a mechanical durability to remain intact, i.e., assembled, over a period of time of at least 1 hour and under the application of a repetitive force of at least 400 grF. In embodiments, the GDRF may include a mechanical durability to remain intact over a period of time of at least 2, 3, 6, 9, 12 and 24 hours and under the application of a repetitive force ranging from about 400 grF to about 3000 grF, in embodiments from about 400 grF to about 1250 grF.

In yet another embodiment there is provided a method for treating a patient in need of extended retention of an API or diagnostic in the stomach by administering an oral pharmaceutical dosage form to the patient including an API or diagnostic for extended retention in a stomach for a predetermined number of hours under fasted or fed conditions. The oral pharmaceutical dosage form may be any of the GRDFs that are described herein.

From the foregoing and with reference to the various figure drawings, those skilled in the art will appreciate that certain modifications can also be made to the present disclosure without departing from the scope of the same.

For example, the present disclosure also relates to an oral pharmaceutical that includes an API or diagnostic configured for extended retention in a stomach for at least 4 hours under fasted conditions. In embodiments, the API is configured for retention in the stomach for at least 6 hours under fasted conditions. Still, in other embodiments, the API is configured for retention in the stomach for at least 8 hours under fasted conditions, in embodiments, at least 10 hours under fasted conditions, and in yet other embodiments, at least 12 hours under fasted conditions.

The present disclosure also relates to an oral pharmaceutical that includes an API or diagnostic configured for extended retention in a stomach for at least 8 hours under fed conditions, in embodiments, at least 10 hours under fed conditions.

In embodiments, the retention in the stomach has an end point in time that is dependent on the extent of drug release. The API may be in an amount within the range of about 0.1 milligrams to about 2.0 grams, in embodiments, about 0.1 milligrams to about 2.0 grams, in embodiments, about 0.2 milligrams to about 1.9 grams, in embodiments, about 0.3 milligrams to about 1.8 grams, in embodiments, about 0.4 milligrams to about 1.7 grams, in embodiments, about 0.5 milligrams to about 1.6 grams, in embodiments, about 0.6 milligrams to about 1.5 grams, in embodiments, about 0.7 milligrams to about 1.4 grams, in embodiments, about 0.8 milligrams to about 1.3 grams, in embodiments, about 0.9 milligrams to about 1.2 grams, in embodiments, about 1 milligrams to about 1.1 grams, in embodiments, about 2 milligrams to about 1 gram, in embodiments, about 5 milligrams to about 900 milligrams, in embodiments, about 10 milligrams to about 800 milligrams, in embodiments, about 20 milligrams to about 700 milligrams, in embodiments, about 50 milligrams to about 600 milligrams, in embodiments, about 100 milligrams to about 500 milligrams, in embodiments, about 200 milligrams to about 400 milligrams, in embodiments, about 250 milligrams to about 400 milligrams, in embodiments, about 300 milligrams to about 400 milligrams. One or more controlled release excipients may be provided that control the release of the API.

The present disclosure also relates to one or more methods for treating a patient in need of extended retention of an active pharmaceutical ingredient (API) or diagnostic in the stomach and at least includes administering an oral pharmaceutical including an API or diagnostic for extended retention in a stomach for at least four hours under fasted and fed conditions.

The present disclosure also relates to a GRDF including a body having two or more arms and configured to transform between a collapsed configuration for ingestion and an expanded configuration for retention within the stomach for a predetermined time period. The arms are pivotable from the collapsed configuration to the expanded configuration within 5 minutes of ingestion to a size sufficient for gastric retention.

The present disclosure also relates to a GRDF including a hinged body configured to transform between a collapsed configuration for ingestion and an expanded configuration for retention within the stomach for a predetermined time period. The hinged body is transformable from the collapsed configuration to the expanded configuration within 5 minutes of ingestion to a size sufficient for gastric retention.

The present disclosure also relates to a GRDF including a body having at least two arms and an active pharmaceutical ingredient (API) retained within at least one of the two arms. After exposure to simulated gastric conditions for 24 hours the two arms dissemble upon a force greater 400 grF.

The present disclosure also relates to a GRDF including a body having at least one of a hinge assembly or a pair of arms and an API retained within at least one of the pair of arms. The body is configured to endure up to 3000 grF without disassembly before the release of the API. The body is configured to disassemble at a force greater than 400 grF following the release of at least 90% of the API, in embodiments, at least 80% of the API, in other embodiments, at least 70% of the API.

The present disclosure also relates to a GRDF including a body made of a pharmaceutically acceptable material and having an initial size and an initial strength, wherein the initial size and initial strength of the body is maintained after at least 24 hr under simulated gastric conditions such that the GRDF cannot pass the 18 mm pipe test (See Experiment 2 above) under 300 grForce.

The present disclosure also relates to a GRDF including a body made of a pharmaceutically acceptable material and including an API having a size and a strength that is maintained after more than 85% of the API is released, such that the GRDF cannot pass the 18 mm pipe test under 300 grForce.

The present disclosure also relates to GRDF including a body having a first arm and a second arm configured to move between a collapsed configuration for ingestion to an expanded configuration for retention in the stomach. The GRDF also includes an API retained within at least one of the two arms, wherein the body in the expanded configuration provides prolonged gastric retention, e.g., retention more than 24 hours, more than 36 hours, more than 48 hours, 2-180 days, 3-120 days, 3-90 days, etc.

The present disclosure also relates to GRDF including an immediate release composition comprising an API or diagnostic, the composition positioned in a cavity defined within a body.

The present invention also relates to a gastroretentive drug form (GRDF) for extended retention in a stomach that includes a body having first and second arms. One or both of the arms include: a cavity defined therein configured to receive an erodible insert; and one or more openings defined therein configured to expose the insert (or a portion thereof) to gastric fluids. A biasing element is included that is configured to move the first and second arms relative to one another. A hinge assembly releasably engages the first and second arms and is configured to allow the first and second arms to pivot relative to one another from a first configuration in close proximity to one another to a second configuration further from one another. The hinge assembly (or a portion thereof) is releasably engaged between at least one of the arms that includes the cavity and the insert. Upon introduction of the GRDF into the stomach, the biasing element moves the first and second arms from the first configuration and gastric fluids access the opening to erode the exposed portion of the insert over time wherein the hinge assembly (or the portion thereof that engages the insert) disengages from the insert and initiates disassembly of the first and second arms from the hinge assembly.

In embodiments, the biasing element maintains the first and second arms in the second configuration. The second configuration of the first and second arms retains the GRDF within the stomach until disassembly. The biasing element may be operably coupled to one of the first and second arms, form part of the hinge assembly, or be a portion of a living hinge. The biasing element may be a spring (e.g., leaf spring) or a superporous hydrogel.

In yet other embodiments, the GRDF may include a retention element configured to maintain the first and second arms in the first configuration prior to ingestion and release the first and second arms after ingestion. The retention element may be biodegradable, e.g., (a biodegradable capsule or band) and/or may be configured to encapsulate at least a portion of the body.

In embodiments, the first and second arms include a size and a shape such that, when disposed in the first configuration, the size and shape of the first and second arms are suitable for swallowing. When disposed in the second configuration, the first and second arms may include a size, a shape and a formation such that at least one of the size, shape and formation of the first and second arms contributes to retention of the GRDF within the stomach.

In yet further embodiments, the hinge assembly (or a portion thereof) is releasably engaged between at least one arm including the cavity and the insert is disposed at the proximal end of the arm. In still other embodiments, the hinge assembly (or a portion thereof) is frictionally engaged between the arm including the cavity and the insert. The hinge assembly (or a portion thereof) may be mechanically engaged to the arm including the cavity and frictionally engaged to the insert.

The one or more openings may be defined in a distal end of the arm such that the insert erodes in a distal-to-proximal manner. The one or more openings may be a slot defined within an inner-facing surface of one of the arms. The size, shape or position of the one or more openings may be configured to control a rate of erosion of the insert. The exposed surface area and disposition of the insert at least partially controls the rate of erosion of each active pharmaceutical ingredient of the insert.

In embodiments, the insert may include one or more active pharmaceutical ingredients. Two or more of the active pharmaceutical ingredients may have different erosion rates. In still other embodiments, one of the arms includes at least two openings defined therein which are disposed in vertical registration with at least two active pharmaceutical ingredients having the same or different erosion rates. The size, shape and position of the at least two openings at least partially controls the rate of erosion of each active pharmaceutical ingredient of the insert.

In other embodiments, the body, biasing element and/or hinge assembly are made from pharmaceutically acceptable materials. The body, biasing element and/or hinge assembly may be manufactured from injection moldable materials.

In embodiments, gastric fluids erode about 80%, or in embodiments, 70%, of the insert over a predetermined time period to initiate detachment of the insert from the hinge assembly (or a portion thereof) and disassembly of the first and second arms from the hinge assembly.

In still other embodiments, at least a portion of the hinge assembly, biasing element, and/or a portion of the body (e.g., first and second arms) is made from a pH sensitive material configured to at least partially erode in the gastrointestinal tract. At least a portion of the hinge assembly may be made from a material that erodes within a pH sensitive range such that the hinge assembly at least partially erodes and detaches from at least one of the first and second arms upon contact with a pH within the pH sensitive range.

The present disclosure also relates to a gastroretentive drug form (GRDF) for extended retention in a stomach, including a body having first and second arms. At least one of the arms includes: a cavity defined therein configured to receive an erodible insert; and one or more openings defined therein configured to expose at least a portion of the insert to gastric fluids. A hinge assembly is included that releasably engages the first and second arms and is configured to bias the first and second arms relative to one another from a first configuration in close proximity to one another to a second configuration further from one another. The hinge assembly (or a portion thereof) is configured to releasably engage between the arm including the cavity and the insert. Upon introduction of the GRDF into the stomach, the hinge assembly moves the first and second arms from the first configuration and gastric fluids access the opening to erode the exposed portion of the insert over time wherein the hinge assembly (or a portion thereof) disengages from the insert and initiates disassembly of the first and second arms from the hinge assembly.

In embodiments, the hinge assembly maintains the first and second arms in the second configuration. When in the second configuration, the first and second arms retain the GRDF within the stomach until disassembly.

In yet other embodiments, the GRDF may include a retention element configured to maintain the first and second arms in the first configuration prior to ingestion and release the first and second arms after ingestion. The retention element may be biodegradable, e.g., a biodegradable capsule or band, and/or may be configured to encapsulate at least a portion of the body.

In embodiments, the first and second arms include a size and a shape such that, when disposed in the first configuration, the size and shape of the first and second arms are suitable for swallowing. When disposed in the second configuration, the first and second arms may include a size, a shape and a formation such that at least one of the size, shape and formation of the first and second arms contributes to retention of the GRDF within the stomach.

In yet further embodiments, the hinge assembly (or a portion thereof) is releasably engaged between the arm including the cavity and the insert is disposed at the proximal end of the arm. In still other embodiments, the hinge assembly (or a portion thereof) is frictionally engaged between the arm including the cavity and the insert. The hinge assembly (or a portion thereof) may be mechanically engaged to the arm including the cavity and frictionally engaged to the insert.

The one or more openings may be defined in a distal end of the arm such that the insert erodes in a distal-to-proximal manner. The one or more openings may be a slot defined within an inner-facing surface of one of the arms. The size, shape or position of the one or more openings may be configured to control a rate of erosion of the insert. The exposed surface area and disposition of the insert at least partially controls the rate of erosion of each active pharmaceutical ingredient of the insert.

In embodiments, the insert may include one or more active pharmaceutical ingredients. Two or more of the active pharmaceutical ingredients may have different erosion rates. In still other embodiments, one of the arms includes at least two openings defined therein which are disposed in vertical registration with at least two active pharmaceutical ingredients having the same or different erosion rates. The size, shape and position of the at least two openings at least partially controls the rate of erosion of each active pharmaceutical ingredient of the insert.

In other embodiments, the body and/or hinge assembly are made from pharmaceutically acceptable materials. The body and/or hinge assembly may be manufactured from injection moldable materials.

In embodiments, gastric fluids erode about 80%, or in embodiments, 70%, of the insert over a predetermined time period to initiate detachment of the insert from the hinge assembly (or a portion thereof) and disassembly of the first and second arms from the hinge assembly.

In still other embodiments, at least a portion of the hinge assembly and/or a portion of the body (e.g., first and second arms) is made from a pH sensitive material configured to at least partially erode in the gastrointestinal tract. At least a portion of the hinge assembly may be made from a material that erodes within a pH sensitive range such that the hinge assembly at least partially erodes and detaches from at least one of the first and second arms upon contact with a pH within the pH sensitive range.

The present disclosure also relates to a gastroretentive drug form (GRDF) for extended retention in a stomach that and includes a body having one or more openings defined therein configured to expose at least a portion of an insert contained therein to gastric fluids. A hinge assembly is configured to allow the body to move from a collapsed configuration to an expanded configuration and at least a portion of the hinge assembly is releasably engaged between the body and the insert. Upon introduction of the GRDF into the stomach, the body transitions from the collapsed configuration and gastric fluids access the opening to erode the exposed portion of the insert over time wherein the at least a portion the hinge assembly disengages from the insert and initiates disassembly of the body from the hinge assembly.

In embodiments, the GRDF may include a retention element configured to maintain the body in the first configuration prior to ingestion and transition the body to the expanded configuration after ingestion. The retention element may be biodegradable, e.g., a biodegradable capsule or band, and/or may be configured to encapsulate at least a portion of the body.

In embodiments, the body includes a size and a shape such that, when disposed in the first configuration, the size and shape of the body is suitable for swallowing. When disposed in the second configuration, the body may include a size, a shape and a formation such that at least one of the size, shape and formation of the body contributes to retention of the GRDF within the stomach.

In yet further embodiments, the hinge assembly (or a portion thereof) is releasably engaged between the body (or a cavity defined within the body) and the insert. In still other embodiments, the hinge assembly (or a portion thereof) is frictionally engaged between body and the insert. The hinge assembly (or a portion thereof) may be mechanically engaged to the body and frictionally engaged to the insert.

The one or more openings may be defined in a distal end of the body such that the insert erodes in a distal-to-proximal manner. The one or more openings may be a slot defined within an inner-facing surface of the body. The size, shape or position of the one or more openings may be configured to control a rate of erosion of the insert. The exposed surface area and disposition of the insert at least partially controls the rate of erosion of each active pharmaceutical ingredient of the insert.

In embodiments, the insert may include one or more active pharmaceutical ingredients. Two or more of the active pharmaceutical ingredients may have different erosion rates. In still other embodiments, the body may include at least two openings defined therein which are disposed in vertical registration with at least two active pharmaceutical ingredients having the same or different erosion rates. The size, shape and position of the at least two openings at least partially controls the rate of erosion of each active pharmaceutical ingredient of the insert.

In other embodiments, the body and/or hinge assembly are made from pharmaceutically acceptable materials. The body and/or hinge assembly may be manufactured from injection moldable materials.

In embodiments, gastric fluids erode about 80%, or in embodiments, 70%, of the insert over a predetermined time period to initiate detachment of the insert from the hinge assembly (or a portion thereof) and disassembly of the body from the hinge assembly.

In still other embodiments, at least a portion of the hinge assembly and/or a portion of the body is made from a pH sensitive material configured to at least partially erode in the gastrointestinal tract. At least a portion of the hinge assembly may be made from a material that erodes within a pH sensitive range such that the hinge assembly at least partially erodes and detaches from the body upon contact with a pH within the pH sensitive range.

The present disclosure also relates to a gastroretentive drug form (GRDF) for extended retention in a stomach, including a body having first and second arms and including a cavity defined therein configured to receive an erodible insert. The body includes at least one opening defined therein configured to expose at least a portion of the insert to gastric fluids. Upon introduction of the GRDF into the stomach, the body transitions from a collapsed configuration to an expanded configuration and gastric fluids access the opening to erode the exposed portion of the insert over time and initiates disassembly of the first and second arms from the body.

In embodiments, at least one of the shape, size and formation of the first and second arms in the expanded configuration retains the GRDF within the stomach until disassembly.

In embodiments, the GRDF may include a retention element configured to maintain the body in the first configuration prior to ingestion and transition the body to the expanded configuration after ingestion. The retention element may be biodegradable, e.g., a biodegradable capsule or band, and/or may be configured to encapsulate at least a portion of the body.

In embodiments, the body includes a size and a shape such that, when disposed in the first configuration, the size and shape of the body is suitable for swallowing. When disposed in the second configuration, the body may include a size, a shape and a formation such that at least one of the size, shape and formation of the body contributes to retention of the GRDF within the stomach.

In yet further embodiments, the hinge assembly (or a portion thereof) is releasably engaged between the body (or a cavity defined within the body) and the insert. In still other embodiments, the hinge assembly (or a portion thereof) is frictionally engaged between body and the insert. The hinge assembly (or a portion thereof) may be mechanically engaged to the body and frictionally engaged to the insert. In yet other embodiment, the hinge assembly is a portion of a living hinge.

The one or more openings may be defined in a distal end of the body such that the insert erodes in a distal-to-proximal manner. The one or more openings may be a slot defined within an inner-facing surface of the body. The size, shape or position of the one or more openings may be configured to control a rate of erosion of the insert. The exposed surface area and disposition of the insert at least partially controls the rate of erosion of each active pharmaceutical ingredient of the insert.

In embodiments, the insert may include one or more active pharmaceutical ingredients. Two or more of the active pharmaceutical ingredients may have different erosion rates. In still other embodiments, the body may include at least two openings defined therein which are disposed in vertical registration with at least two active pharmaceutical ingredients having the same or different erosion rates. The size, shape and position of the at least two openings at least partially controls the rate of erosion of each active pharmaceutical ingredient of the insert.

In other embodiments, the body and/or hinge assembly are made from pharmaceutically acceptable materials. The body and/or hinge assembly may be manufactured from injection moldable materials.

In embodiments, gastric fluids erode about 80%, or in embodiments, 70%, of the insert over a predetermined time period to initiate detachment of the insert from the hinge assembly (or a portion thereof) and disassembly of the body from the hinge assembly.

In still other embodiments, at least a portion of the hinge assembly and/or a portion of the body is made from a pH sensitive material configured to at least partially erode in the gastrointestinal tract. At least a portion of the hinge assembly may be made from a material that erodes within a pH sensitive range such that the hinge assembly at least partially erodes and detaches from the body upon contact with a pH within the pH sensitive range.

The present disclosure also relates to a gastroretentive drug form (GRDF) for extended retention in a stomach that includes a body including first and second arms, at least the first arm having: a cavity defined therein configured to receive an erodible insert; at least one opening defined therein configured to expose at least a portion of the insert to gastric fluids; and a hinge assembly including a first portion releasably engaged to the first arm and a second portion releasably engaged to the second arm. The first and second portions are operably coupled to one another and configured to bias the first and second arms relative to one another from a first configuration in close proximity to one another to a second configuration further from one another. The first portion is releasably engaged between the first arm and the insert. Upon introduction of the GRDF into the stomach, the hinge assembly moves the first and second arms from the first configuration and gastric fluids access the opening to erode the exposed portion of the insert over time wherein the first portion disengages from the insert and initiates disassembly of the first and second arms from the hinge assembly.

In embodiments, the first portion includes a mechanical interface that matingly engages a corresponding mechanical interface disposed on the second portion to permit pivotable motion of the first portion relative to the second portion. The first portion may be a C-shaped clip and the second portion may include a post configured to receive the C-shaped clip in a snap-fit manner.

In embodiments, the first portion includes a rotation limiting surface to prevent over-rotation of the first and second portions relative to one another. At least one of the first and second portions includes a mechanical interface that is configured to releasably engage a corresponding mechanical interface disposed on at least one of the first and second arms. The mechanical interface on at least one of the first and second portions may include a prong and the corresponding mechanical interface disposed on at least one of the first and second arms may include an opening defined therein that complements the prong.

In embodiments, the amount of the API is shared evenly in each of the arms. In other embodiments, the amount of the API is not shared evenly in each of the arms.

A method of assembling a gastroretentive dosage form (GRDF) is provided in accordance with the present disclosure and includes: inserting an insert tablet into a cavity of a body formed by injection molding; and combining the body with a hinge assembly.

A method of delivery of an API or diagnostic is provided in accordance with the present disclosure that includes administering to a patient a GRDF of any of the previous claims in a closed configuration.

A method of manufacturing a dosage form for gastric retention is provided in accordance with the present disclosure that includes forming a body of the dosage form including a cellulose ester composition.

In embodiments, the cellulose ester composition includes a cellulose ester and a plasticizer. In embodiments, the cellulose ester is cellulose acetate and the plasticizer is triacetin.

A method of forcing a disassembly of a GRDF within a patient is provided in accordance with the present disclosure that includes: administering a GRDF to a patient; and administering an antidote to the patient, wherein the antidote increases a pH of the patient's stomach forcing the GRDF to disassemble into pieces of sufficient size to evacuate the stomach.

In embodiments, the GRDF includes a body comprising a pH sensitive material which represents less than about 20% of a total weight of the body, wherein the pH sensitive material is configured to force the GRDF to disassemble.

The present disclosure also includes the use of an immediate release formulation in the manufacture of a GRDF is provided. In embodiments, the formulation is an insert (tablet).

A controlled release formulation is provided in accordance with the present disclosure that includes a body including a cavity suitable for retaining an API composition, wherein the body defines a surface area of exposure of the API composition which allows for the controlled release of the API.

In embodiments, the API is released over more than 4 hours, in aspects, over more than 8 hours, in aspects, over more than 12 hours, in aspects, over more than 18 hours, in aspects, over more than 24 hours.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

EXAMPLES

Example 1—Preparation of GRDF

A. Preparation of Hot Melt Extrudant (HME)

Seven hot melt extrudants were prepared according to parameters described in Table 1.

3. After 24 hr the mixture was fed into the HME machine (e.g. by a gravimetric feeder at 1 kg/hr rate).
4. The HME machine was pre-heated to the defined temperature (e.g. 190° C. for Extrudent No. 3 in Table 1).
5. The HME snail speed was set to 100 RPM.
6. While the HME machine was fed with the material, a vacuum system attached to the HME machine was activated to enable drawing any water in the mixture.
7. As the melted material was drawn from the HME machine it was forwarded as strands onto a conveyor belt and cooled. Once cooled, the strand was chopped by a chopping machine to particles of about 1.5-2 mm size.
8. After chopping, the material was dried under vacuum at 50° C. for 5 hr to enable water evaporation (loss on drying was recorded at below 1%).

TABLE 1

Preparation on Extrudants in HME Machine

| Extrudant No. | Polymer | Plasticizer | Polymer:Plasticizer Ratio | Pre-Mixing time (min, RPM) | Hold time | Hot melt flow rate 1 kg/hr | HME temp {° C.] | HME RPM snail | Milled pellets |
|---|---|---|---|---|---|---|---|---|---|
| 1 | HPMC Acetate succinate HG | Triethyl citrate | 4:1 | 5 min, 500 RPM | 24 hr | 1 | 170 | 100 | 1.5 mm |
| 2 | HPMC Acetate succinate | PEG 3350 | 8:1 | 5 min, 500 RPM | 24 hr | 1 | 170 | 100 | 1.5 mm |
| 3 | Cellulose acetate | Triacetin | 4:1 | 2-5 min, 500 RPM | 24 hr | 1 | 190 | 100 | 1.5 mm |
| 4 | ETHOCEL ®7CP | Triethyl citrate | 4:1 | 5 min, 500 RPM | 24 hr | 1 | 160 | 100 | 1.5 mm |
| 5 | EUDRAGIT ® S | Triethyl citrate | 4:1 | 5 min, 500 RPM | 24 hr | 1 | 150 | 100 | 1.5 mm |
| 6 | HPMC Acetate succinate HG:MG 1:4 | Triethyl citrate | 12:1 | 2 min, 500 RPM | 24 hr | 1 | 170 | 100 | 1.5 mm |
| 7 | Cellulose acetate KLUCEL ® 10:1 | Triethyl citrate | 5:1 | 2 min, 500 RPM | 24 hr | 1 | 160 | 100 | 1.5 mm |

Specifically, with reference to Extrudant No. 3, the materials loaded into the injection molding machine were prepared by the following sequential steps:
1. The polymer (e.g. cellulose acetate 0.5 kg) was pre-mixed with the plasticizer (e.g. Triacetine 0.125 kg) in DIOSNA mixer (6 L) for 5 min, 500 RPM.
2. After premixing, the mixture was place at room temperature for 24 hr so that the polymer and plasticizer settled together.

B. Preparation of GRDF Mold Via Injection Molding

The relevant mold tool was placed in a suitable injection molding machine. The hot melt extrudants were applied to an injection molding machine (Wittman EcoPower 55 Ton Injection Molding Machine) and injection molded, as described above, while using the parameters listed in Table 2.

TABLE 2

| Formulation No. | Extrudant No. from Table 1 | Polymer | Plasticizer | Extrusion temp [° C.] | Screw speed [rpm] | Nozzle temp [° C.] | Ejection pressure [kg/cm2 | Mold temp [° C.]| | Cycle time [sec] |
|---|---|---|---|---|---|---|---|---|---|
| 1 | 1 | HMPC Acetate succinate HG | Triethyl citrate | 175-190 | 200 | 210 | 1200 | 40 | 17 |
| 2 | 2 | HMPC Acetate succinate | PEG 3350 | 150-180 | 200 | 185 | 1200 | 40 | 18 |
| 3 | 3 | Cellulose acetate | Triacetin | 180 to 200 | 250 | 230 | 1600 | 45 | 18 |
| 4 | 4 | ETHOCEL ® 7CP | Triethyl citrate | 160-175 | 250 | 180 | 1000 | 50 | 30 |

TABLE 2-continued

| Formulation No. | Extrudant No. from Table 1 | Polymer | Plasticizer | Extrusion temp [° C.] | Screw speed [rpm] | Nozzle temp [° C.] | Ejection pressure [kg/cm2] | Mold temp [° C.] | Cycle time [sec] |
|---|---|---|---|---|---|---|---|---|---|
| 5 | 5 | EUDRAGIT ® S | Triethyl citrate | 160-200 | 250 | 210 | 1600 | 50 | 20 |
| 6 | 6 | HMPC Acetate succinate HG:MG 1:4 | Triethyl citrate | 175-190 | 200 | 210 | 1200 | 40 | 17 |
| 7 | 7 | Cellulose acetate KLUCEL ® 10:1 | Triethyl citrate | 180 to 200 | 250 | 230 | 1600 | 45 | 18 |

C. Preparation of the Insert Tablets

Figure 54:
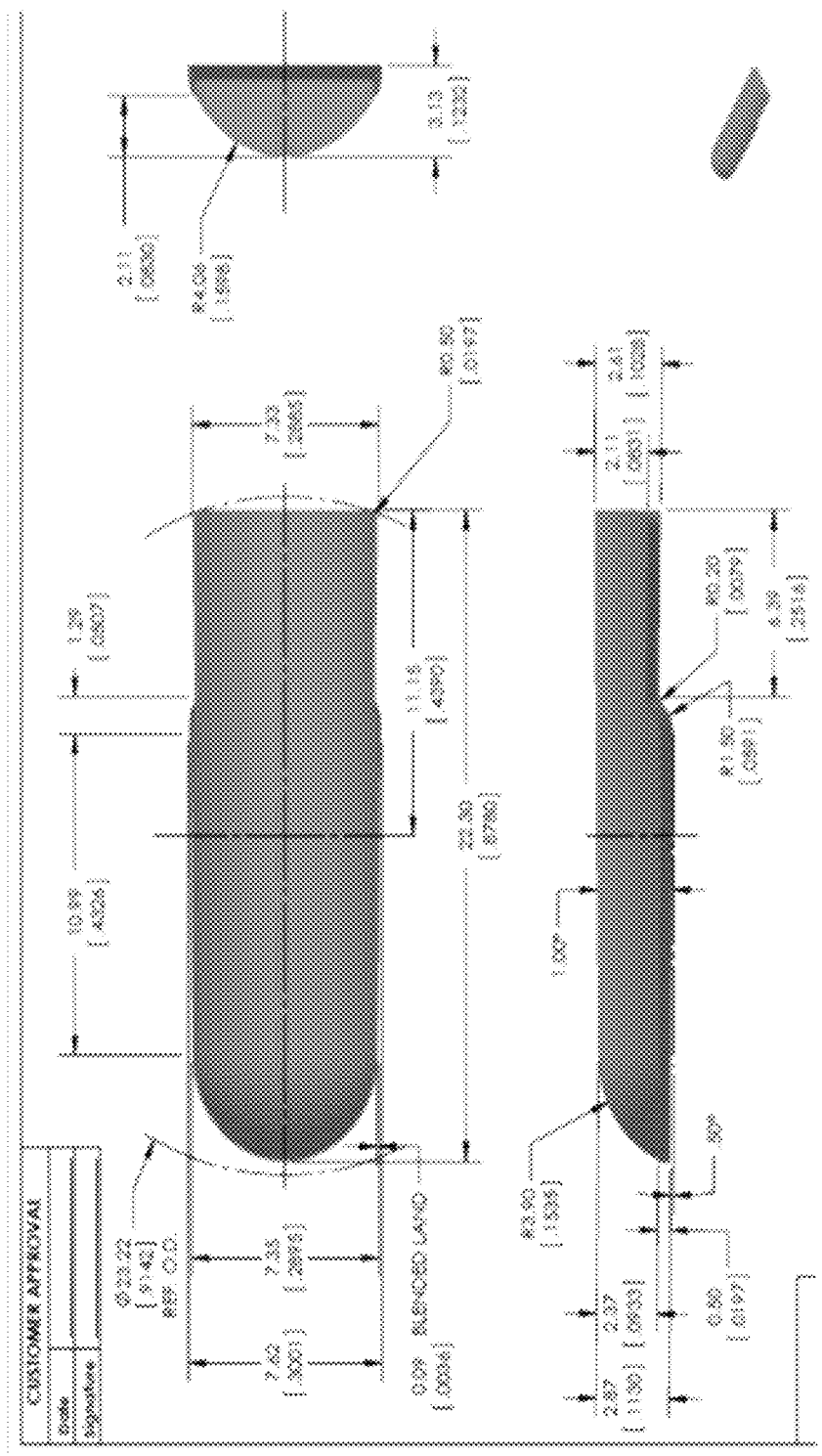
FIG. 54 depicts an insert prepared with specific dimensions according to one embodiment of the present disclosure for use with some of the Examples disclosed herein.

Punches according to the insert were prepared and include the dimensions depicted in FIG. 54.

Internal granulation ingredients were mixed thoroughly in a Ycone mixer for 5 minutes. After mixing, the ingredients were wet granulated with cold water in a diosna mixer. The granulate obtained was dried in a fluid bed drier (FBD). Later, the granulate was milled in a Erweka milling machine. After milling, extra-granulate ingredients were added and thoroughly mixed in the Ycone mixer for 5 minutes. The final blend obtained was compressed to tablets using a Bonapache D compressing machine having a 22.5×9.0 mm die. Hardness of 20 SCU was obtained. Alternatively, the final blend was compressed manually using a SPECAC compressing unit having a 2 ton force and a 6×12.5 mm die. The composition of each insert is shown in Table 3.

TABLE 3

|  | Insert Tablet 1 mg | Insert Tablet 2 mg | Insert Tablet 3 mg | Insert Tablet 4 mg |
|---|---|---|---|---|
| Internal Granulation |  |  |  |  |
| API | 500 | 370 | 370 | 370 |
| HPMC E4M | 13 | 6.6 | 9.7 | 9.7 |
| Starch 1500 | 180 | 20 | 20 | 20 |
| Wet granulation |  |  |  |  |
| Water (cold) |  |  |  |  |
| Extragranulate |  |  |  |  |
| AVICEL ® 102 | 100 | 23.4 | 28.3 | 31 |
| MgS | 7 | 4 | 4 | 4 |
| Sodium starch glycolate |  | 16 | 8 | 5.3 |
| Total Weight | 800 | 440 | 440 | 440 |

The insert was compressed using a conventional press machine to obtain tablets with a size which matches the inner side of the arms (prepared by injection molding, as described above). The distance from the insert outer surface to the inner surface of the arms wall was about 5 to 150 microns to enable proper insertion. The final adjustment of the insert size was completed by adjustment of the insert weight and the compression force.

D. Assembly of the GRDF

Insert tablet 1 was inserted into each of the two arms prepared from Formulation No. 3 (see Table 2) with a variety of insert tablet surface area exposure as in Table 4. The hinge and the arms were assembled by pushing the hinge into the arms. The obtained assembled unit was collapsed (i.e., FIG. 33 for example) and inserted into a 000 gelatine capsule, e.g., CAPSUGEL® (See FIG. 16 for example) and subjected to dissolution trials, as described below.

Example 2—Dissolution Study 1

Each assembled GRDF was placed in a Rotating apparatus [VANKEL ROTATING BOTTLE apparatus (VARIAN)] and subjected to dissolution and emptying tests. 500 ml dissolution chamber bottle was used with 400 ml HCL 0.1N at 37° C. and 150 grams of glass beads. The dissolution chamber was rotated at 8 RPM. 5 ml samples were taken after 1, 2, 3, 5, 6, and 24 hours to measure API release rate.

TABLE 4

|  | Sample 1 | Sample 2 | Sample 3 | Sample 4 |
|---|---|---|---|---|
| Formulation | Insert tablet 1 [above] | Insert tablet 1 [above] | Insert tablet 1 [above] | Insert tablet 1 [above] |
| Injection Molded Mold | Extrudant 3 | Extrudant 3 | Extrudant 3 | none |
| IM Release area | Front - see FIG. | Front - see FIG. | Front + Deck - see FIG. | none |
| Presence of beads | No beads | 150 g beads | 150 g beads | 150 g beads |

Figure 37:
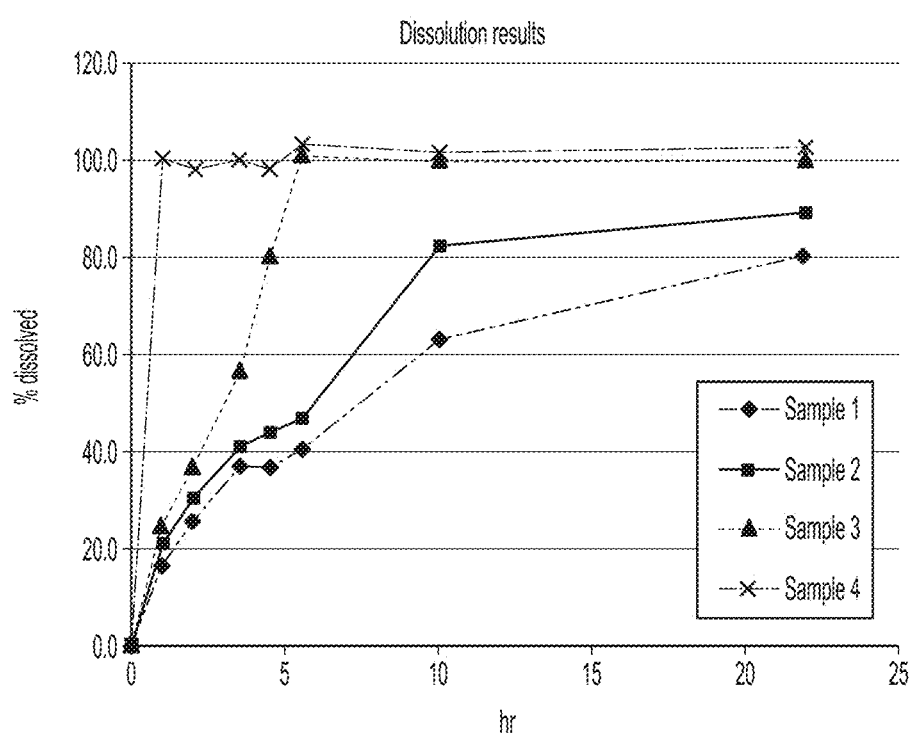
FIGS. 37-39 depict the results of various dissolution tests.

The results of the dissolution tests are shown in FIG. 37. In summary:

1. Sample 1 resulted in an extended release profile of up to 24 hr.
2. Sample 2 (wherein glass beads provided an increase in mechanical effect on the GRDF) resulted in a moderate increase in release profile but with no dose dumping effect.
3. Sample 3, having more release holes than Sample 2 (front and deck openings), resulted in an increase in release profile.
4. Sample 4 (insert only, not contained in arms) resulted in a release profile which was very fast—100% within 1 hr.

Example 3—17.5 mm Pipe Test

A 17.5 mm pipe test was performed on Sample 2 (See Table 4) to simulate exit of the GRDF components from the stomach. The pipe test was done at T=0, T=10 hr and T=24 hr. A standard bottle head was switched to a pipe having a diameter of 17.5 mm and a length of 5 cm. Content was tested for capacity to exit the bottle by manual shaking in an upside-down position.

TABLE 5

Pipe test results of standard extended release ("ER") tablet (Insert)

|  | T = 0 | T = 10 hr | T = 24 hr |
|---|---|---|---|
| Standard ER Tablet Sample 2 (See Table 4) | Exited pipe Remained in pipe | Exited pipe Remained in pipe, insert tablet 80% eroded | Exited pipe Exited pipe, insert tablet eroded |

Example 4A: Dissolution Test 2

Samples described in Table 5A below were placed in 500 ml dissolution chamber bottle (described above) where 400 ml with solution of HCL 0.1N or buffer acetate pH 4.5 at 37° C. and with or without 150 grams of glass beads which were added beforehand. The dissolution chamber was rotated in 8 RPM. 5 ml samples were taken after 1, 2, 3, 5, 6 and 24 hours to measure API release rate.

TABLE 5A

|  | Example 4a | Example 4b | Example 4c | Example 4d |
|---|---|---|---|---|
| Formulation | Standard ER tablet | Standard ER tablet | See Sample 2 | See Sample 2 |
| IM part | none | none | See Sample 2 | See Sample 2 |
| IM release area | none | none | Front | Front |
| Dissolution mechanics by | No beads | 150 g beads | No beads | 150 g beads |
| pH | 1 | 1 | 1 | 1 |

Figure 38:
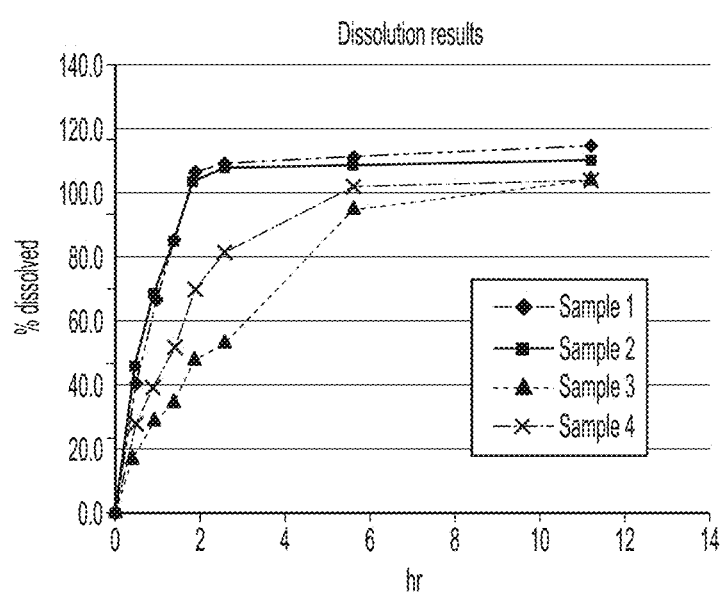

The results of this dissolution test are shown in FIG. 38. In summary:
1. Sample 4c resulted in an extended release profile of up to 12 hr.
2. Sample 4d resulted in a moderate increase in release profile with no dose dumping effect.
3. Samples 4a and 4b (i.e., standard ER tablet) resulted in complete release within 4 hr, independent of increased mechanical force applied by the glass beads.

Example 5A—Preparation of GRDF

Two GRDF configurations were made, both with the same insert formulation (see Table 6 below); Configuration 1 was made from erodible, pH dependent, injection molding parts and Configuration 2 was made from harder, non pH dependent, injection molding parts. The "inserts" were inserted into two each of the two arms (1 & 2) according to Table 6 below. The hinge assembly and the arms were assembled by pushing the hinge assembly into the arms, e.g., see FIG. 34A. The obtained assembled unit was closed and inserted into a 000 gelatine capsule (CAPSUGEL®) and subjected to dissolution trials, as described below.

TABLE 6

|  | Configuration 1 | Configuration 2 |
|---|---|---|
| IM parts | erodible, pH dependent | non erodible, non pH dependent |
| T arm * | Extrudant 6 HPMC HG:MG:Triacetin 9:3:1.2 | Extrudant 3 CA:triacetin 4:1 |
| S arm * | Extrudant 7 CA:Triacetin:klucel 10:2:1 | Extrudant 7 CA:Triacetin:klucel 10:2:1 |
| T hinge * | Extrudant 3 CA:triacetin 4:1 | Extrudant 3 CA:triacetin 4:1 |
| S hinge * | Extrudant 7 CA:Triacetin:klucel 10:2:1 | Extrudant 3 CA:triacetin 4:1 |
| Formulation |  |  |
| T arm formulation ** | Insert 2 | Insert 3 |
| S arm formulation ** | Insert 2 | Insert 3 |

\* See Table 2 above
\*\* See Table 3 above

Example 5B—Dissolution Study 3

The two assembled GRDF configurations were placed in the Rotating apparatus [VANKEL ROTATING BOTTLE apparatus (VARIAN)] and subjected to dissolution and emptying tests. 500 ml dissolution chamber bottle was used (described herein) with 400 ml HCL 0.01N (pH 2) or with buffer acetate (pH 4.5) at 37° C. The dissolution chamber was rotated at 8 RPM. 5 ml Samples were taken after 0.5, 1.5, 2.5, 4, 5.5, 8, and 22 hr to measure API release rate. After 4 hr the sampling medium was switched with fresh medium. The disassembly of the GRDF was also monitored (disassembled parts tested for passage through a pipe test tube as an indicator for gastric emptying as described herein). Unfolding time for the GRDF was monitored. Following 22 hr of exposure of Configuration 1 to pH 2, the medium was switched to buffer phosphate pH 6.5 to test erosion/dissolution time of the GRDF components.

Figure 39:
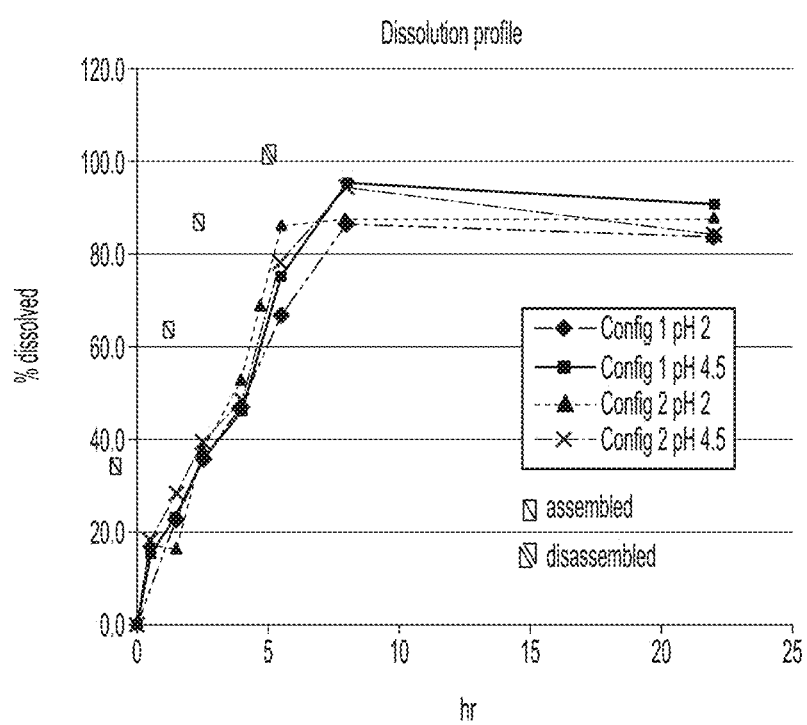

At T=0, the GRDFs were inserted into the rotating apparatus in the collapsed configuration contained within a capsule. At T=5 min, all capsules were dissolved and the GRDFs were unfolded. The results of this dissolution and disassembly study are shown in FIG. 39.

In Summary:
1. No significant difference in unfolding time, release profile, or disassembly time were observed for both configurations.
2. Unfolding was achieved in all cases in less than 5 minutes.
3. Near Zero order profile of about 8 hr was obtained.
4. The release profile was not affected significantly by pH alteration (pH 2.5 vs pH 4.5)
5. Disassembly took place after more than 8 hr, at which point more than 85% of the API was released.
6. pH dependent parts were eroded and dissolved completely within 5 hours.
7. pH dependent parts were eroded and dissolved completely within 5 hours.

Example 6: Openings and Formulation Effect on Release Profile a. Formation of GRDF Mold:
Formulation 3 from Example 1B was used to produce molds in FIGS. 34B and 35 where two parallel lines of equal number of holes run from tip to hinge along the arm.
b. Preparation of Insert
Insert composition is shown in Table 7 below.

TABLE 7

|  | Configuration 1 insert tab A [delete in final: R-11529] | Configuration 2 insert tab B [delete in final: R-11750A] |
|---|---|---|
| Ingredients |  |  |
| internal gran A |  |  |
| API | 370 | 370 |
| HPMC E4M | 9.7 | 8 |
| Starch 1500 | 20 | 20 |
| extragranulate |  |  |
| avicel 102 | 28.3 | 22 |
| SSG (sod. Starch glyc) | 8 | 16 |
| MgS | 4 | 4 |
| Total weight | 440 | 440 |

Internal granulation ingredients were mixed thoroughly in a Ycone mixer for 5 minutes. After mixing, the ingredients were wet granulated with cold water in a diosna mixer. The granulate obtained was dried in a fluid bed drier (FBD). Later, the granulate was milled in a Erweka milling machine. After milling, extra-granulate ingredients were added and thoroughly mixed in the Ycone mixer for 5 minutes. The final blend obtained was compressed to tablets using a Bonapache D compressing machine having a 22.5×9.0 mm die. Hardness of 10 SCU was obtained. Alternatively, the final blend was compressed manually using a SPECAC compressing unit having a 2 ton force and a 6×12.5 mm die.

Punches according to the insert of the tablet were prepared with the dimensions (in millimeters) as shown in FIG. 54.

Figure 26:
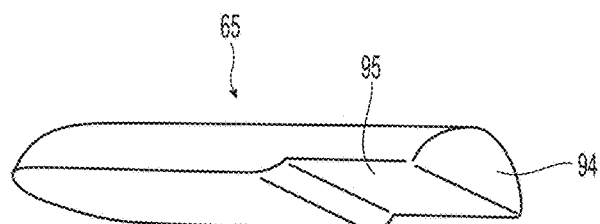
FIG. 26 depicts a perspective view of an insert of the GRDF of FIG. 17A.

The insert in FIG. 26 was compressed using a conventional press machine to obtain inserts tablets. The insert tablet was inserted into the cavity of the arm mold (as exemplified in FIG. 28-31) which on assembly was sandwiched between the hinge and the arm mold. To enable smooth insertion, a tolerance (gap) between the insert outer surface to the inner surface of the arm mold was set to about 50 to 150 μm. In addition, a final adjustment of the insert size dimensions to enable smooth insertion was done through tablet compression by adjustment of the insert weight and the compression force.

a. Assembly of the GRDF

As shown in FIG. 18, one insert was inserted into each of the two arms. The hinge assembly, hinge assembly 66, and the arms, e.g., arms 62 and 64 were assembled by pushing the hinge assembly 66 into respective cavities 62' and 64' between the insert and the hinge assembly 66.

TABLE 8

Assembled units configurations before test

| sample | Mold composition | mold holes size diameter, number of holes | inner formulation | SSG | HPMC E4M (MET) |
|---|---|---|---|---|---|
| 1 | CA Triacetine 4:1 | no holes | Insert Tab A | 1.8 | 2.2 |
| 2 | CA Triacetine 4:1 | 1.4 mm, 4holes | Insert Tab A | 1.8 | 2.2 |
| 3 | CA Triacetine 4:1 | 2 mm, 10holes | Insert Tab A | 1.8 | 2.2 |
| 4 | CA Triacetine 4:1ine | no holes | Insert Tab B | 3.6 | 1.8 |
| 5 | CA Triacetine 4:1 | 2 mm, 10holes | Insert Tab B | 3.6 | 1.8 |

The Assembled product is shown in FIG. 34B b. Dissolution Study

The two assembled GRDF configurations were placed in the Rotating apparatus [VANKEL ROTATING BOTTLE apparatus (VARIAN)] and subjected to dissolution and emptying tests. A 500 ml dissolution chamber bottle was used with 400 ml HCL 0.01N (pH 2) or with buffer acetate (pH 4.5) at 37° C. The dissolution chamber rotated in 8 RPM. 5 ml Samples were taken after 0.5, 1.5, 2.5, 4, 5.5, 8 and 22 hrs to measure API release rate. After 4 hrs, sampling medium was switch with new fresh medium.

Figure 52:
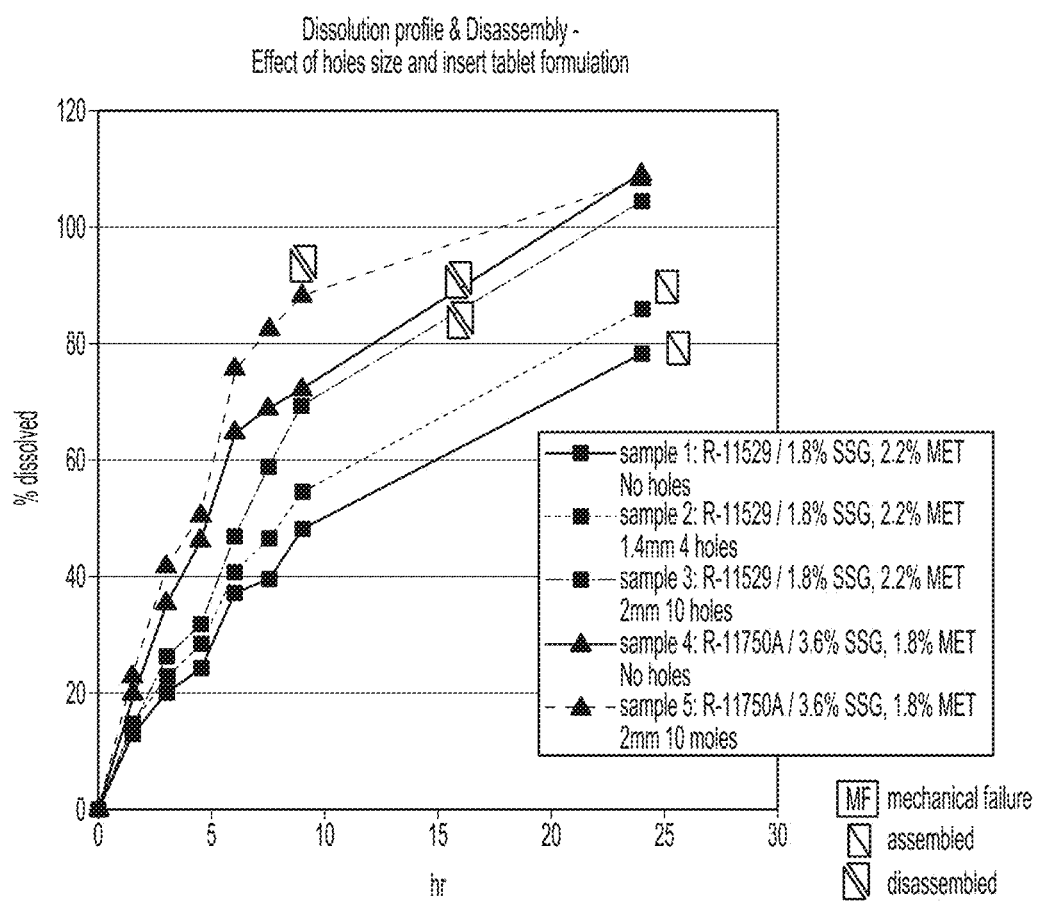
FIG. 52 is a graphical illustration of the dissolution profile and disassembly time of the GRDF with varying hole geometries.

Results:

a. Dissolution profile and disassembly time is shown in FIG. 52.

Conclusions:

a. There was no significant difference in expanding time. Unfolding was achieved with <3 min
b. Disassembly consistently occurred at about 80% API release
c. Disassembly could be shifted between about 7 hrs and at least 24 hrs by modifying holes and excipients.
  1. Mold external surface area: Increasing the diameter of the holes resulted in a faster profile
  2. Increasing the disintegrant while lowering the matrix polymer (MET) resulted in an increased profile Example 7: An 18 mm Pipe Test for Simulating Gastric Retention Under an Applied Force a. Assembly of a GRDF The molded parts, i.e., the arms, hinge assembly, and biasing element (e.g., leaf spring), of the GRDF were made of Cellulose Acetate (CA) and Triacetin combined in a 4:1 ratio, respectively. (See, Formulation No. 3 from Table 2)

Insert No. 4 was placed into each of the molded arms made from the formulation provided in Table 3. Then the arms were combined with the hinges to form a fully assembled GRDF.

b. Experiment 1—GRDF Exposure to Gastric Simulated Conditions Prior to PIPE Test (Test Done in Triplicates)

The fully assembled GRDF was placed in simulated gastric conditions i.e., at 37° C., pH2+Xanthan gum 0.125 gr/L, 25 RPM mixing. In this model, the formulation obtained a near zero order release profile for 20 hr. At T=0, 1, 3, 6, 9, 24 hr the product was taken out of the rotating apparatus and immediately subjected to a second Pipe test as described below to evaluate the 24 hr durability of the GRDF to resist passing through the pipe.

c. Experiment 2—Second [18 mm] Pipe Test Apparatus

Figure 40A:
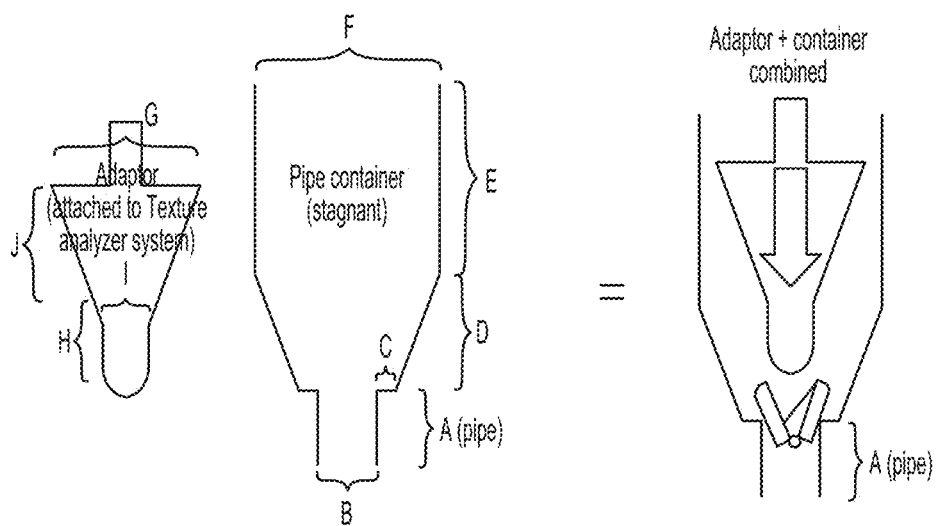
FIG. 40A depicts a schematic illustration of a pipe testing apparatus.
Figure 40B:
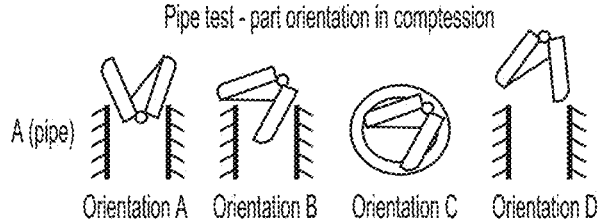
FIG. 40B depicts a schematic illustration of the GRDF in varying orientations.

The scheme of the 18 mm pipe test is depicted in FIGS. 40A and 40B. The dimensions are further described below in Table 9. In short, an adaptor was attached to a texture analyzer HD purchased from Stable Microsystem, Corp. A 5 kg load cell was used for the test.

In each interval (T=0, 1, 3, 6, 9, and 24 hr), the GRDF was extracted out of the dissolution apparatus and placed in the pipe container in 3 orientations (A, B, and C) as illustrated in FIG. 40B. In each orientation, a force of 600 grF was applied 10 times at a speed of 10 mm/sec (by the adaptor descending and ascending). In the last interval, the adaptor was forced to descend through the pipe so to measure the maximal force needed for the GRDF to pass through the pipe or to break into parts. In addition, the GRDF was randomly thrown gently into the pipe container 10 different times, and each time exposed to the same force, as provided above. The results are given below.

TABLE 9

| # | Description | Dimension (mm) |
|---|---|---|
| A | Pipe height | 30 |
| B | Pipe passkey diameter | 18 |
| C | Pipe Passkey edge | 4 |
| D | Cone height | 45 |
| E | Cylinder height | 60 |
| F | Cylinder diameter | 70 |
| G | Adaptor cone base diameter | 60 |
| H | Adaptor lead height | 30 |
| I | Adaptor lead diameter | 15 |
| J | Adaptor cone d | 40 |

Test Results

The test results are described in Table 10 below. Some specific results include the following:
1. Insert erosion was near a zero order rate (visual observation of material remained)
2. The sample GRDFs endured mechanical forces of up to 3000 grF after 24 hr without significant deformation. (at orientation B, C, and D)
3. The sample GRDFs disassembled under the application of 400 grF, when positioned in orientation D, at 24 hr, and as the insert almost completely eroded.

d. Experiment 3: In Vitro Leaf Spring Durability Test

The expanded configuration of the GRDFs described herein is highly dependent on the biasing mechanism or leaf spring durability when subjected to mechanical forces, e.g. compression that might occur in the stomach. Such forces might cause downsizing and/or folding of the GRDF resulting in premature emptying from the stomach and insufficient gastric retention.

The leaf spring durability test was used to evaluate the degree of deformation of the GRDF in response to increasing compression forces applied thereto. The compression forces were applied as described below.

The sample GDRF was tested at T=0 and immediately after exposure to simulated gastric fluids—5 RPM Rotating apparatus having 37° C., Xanthan gum [0.125 gr/L pH2] with 25 RPM mixing for 12 hrs.

Figure 41:
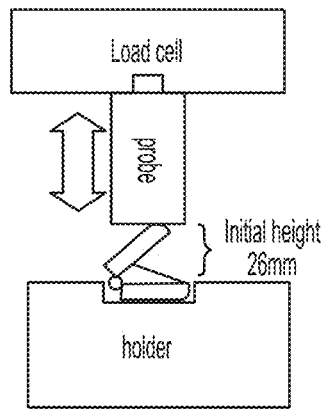
FIG. 41 depicts a schematic illustration of a spring durability testing apparatus.
Figure 42:
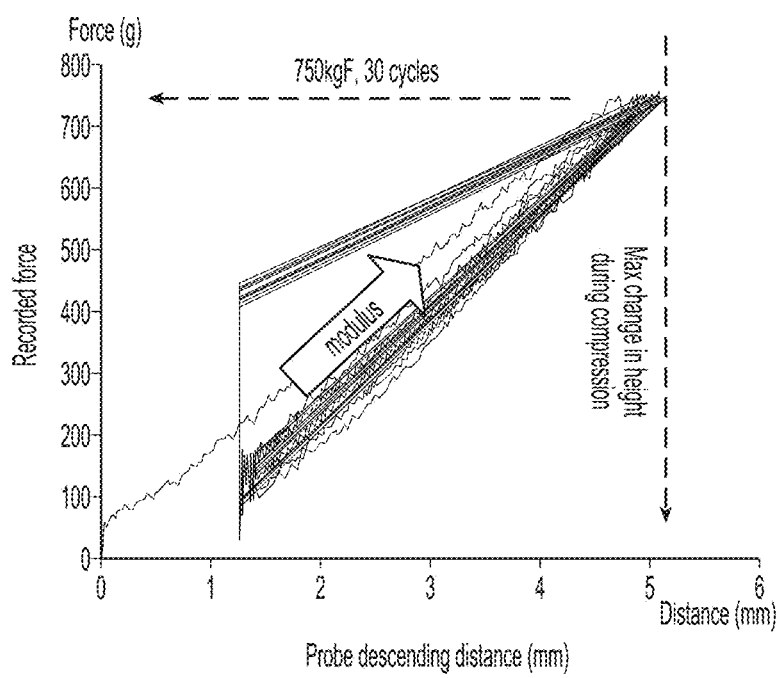
FIGS. 42 and 43 depict graphs showing the results of the spring durability test using the apparatus of FIG. 41.
Figure 43:
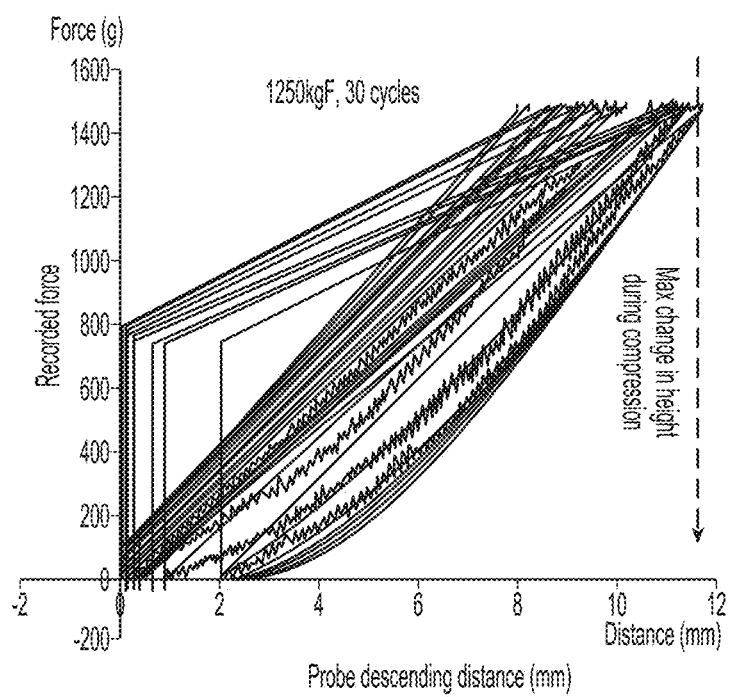

The sample GDRF was attached to a holder (keeping the sample GDRF stagnant). The holder was placed below the Texture analyzer (Stable Microsystem, Corp.). As illustrated in FIG. 41, a probe was attached to a load cell of 5 kgF. Thereafter, the probe descended upon the sample GDRF and contacted the sample GRDF (trigger force of 20 gr) while descending, the force derived and the change in probe position were recorded by the load cell. After reaching the defined force the probe ascended back to the start position. This cycle was applied 30 times with a 5 second recovery in between cycles. The GRDF compression modulus (gr/mm) as well as plasticity after 30 cycles were calculated (see FIGS. 42 and 43 and Table 11 below)

Test Results:

The test results are described in Table 11 below. Some specific results include the following:
1. At t=0 and after 12 hr of exposure to simulated gastric fluids the GRDF had 3% plastic deformation (plasticity) after 30 cycles.
2. At t=0 the GRDF 350 grF compression resulted in less than 6% deformation. Calculated compression modulus was 175 gr/mm.
3. Only by applying 1250 grF did the GRDF have significant plastic deformation (marked in FIGS. 42 and 43)

TABLE 10

| grForce time | % insert tab remaining (visual observation) | Forced applied grFroce | Did part retain on pipe or pass through it? Orientation | | | | comment |
|---|---|---|---|---|---|---|---|
| | | | A | B | C | D (random) | |
| 0 | 100 | 600 | did not pass through pipe | did not pass through pipe | did not pass through pipe | did not pass through pipe | mold remained intact |
| 1 | 95 | 600 | did not pass through pipe | did not pass through pipe | did not pass through pipe | did not pass through pipe | mold remained intact |
| 3 | 90 | 600 | did not pass through pipe | did not pass through pipe | did not pass through pipe | did not pass through pipe | mold remained intact |
| 6 | 80 | 600 | did not pass through pipe | did not pass through pipe | did not pass through pipe | did not pass through pipe | mold remained intact |
| 9 | 70 | 600 | did not pass through pipe | did not pass through pipe | did not pass through pipe | did not pass through pipe | mold remained intact |
| 24 | 10 | 300 | did not pass through pipe | did not pass through pipe | did not pass through pipe | passed* | mold remained intact |
| 24 | 10 | 400-3000 | passed* | did not pass through pipe | did not pass through pipe | passed* | |

*parts disassembled.

TABLE 11

| exposure time to simulation gastric fluids | Force applied [grams] | Maximum change in height during compression after cycle 1 [mm] | Maximum % change in height during compression after cycle 1 [%] | compression modulus after cycle 1 (gr/mm) | deformation % (plasticity) % change compare to T = 0 in initial height at cycle 30 after 5 sec recovery |
|---|---|---|---|---|---|
| 0 hr (T = 0) | 350 | 1.5 | 5.8 | 175 | 0.0 |
|  | 750 | 5 | 19.2 | 150 | −1.9 |
|  | 1250 | 12 | 46.2 | N/A | −15.4 |
| 12 hr | 750 | 6 | 23.1 | 170 | −3.0 | e. Experiment 4—PIG Study-Time Until the GDRF Opens and Safety and Durability of the GRDF Three (3) pigs were given the GRDF which included an insert tablet made according to the formulation provided in Table 12 below. The GRDF was then encapsulated within a gelatin capsule 000* (CAPSUGEL®). As the GRDF was 28 mm in length, the size 000 gelatin capsule was not fully locked.

TABLE 12

| batch R-11206 | detail |
|---|---|
| tablet preparation by | mixing folowed by direct compression |
| ingredients | mg/tab |
| Ethocel 7CPS | 158.4 |
| HPMC E4M | 13.2 |
| Starch 1500 | 88 |
| Lactose SD | 158.4 |
| SSG (sod. Starch glyc) | 4.4 |
| MgS | 17.6 |
| Total Weight | 440 |

The study was conducted in the LAHAV research institute (Israel). Each of the pigs were anesthetized (short term 10 min anesthesia) and given 200 ml at 37° C. After 5 minutes, the pigs were administered the GRDF. Endoscope testing was performed at T=4.5 hr, 9 hr, and 24 hrs.

Figure 44:
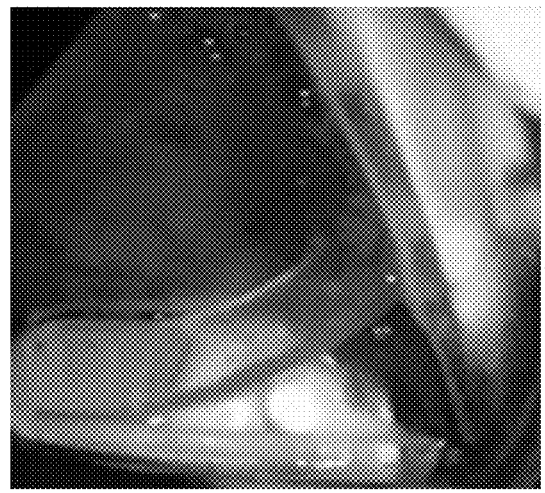
FIGS. 44 and 45 are photographs of the extent of deformation of the GRDF of the Pig Study of Example 9.
Figure 45:
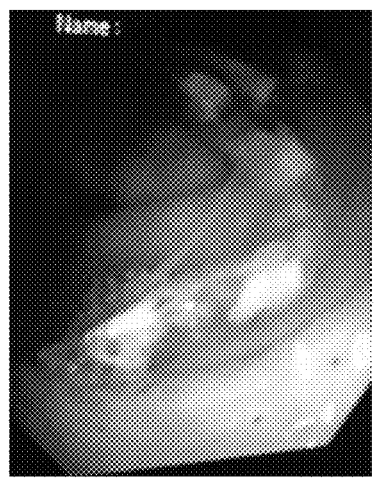

Test Results:
Some specific test results included the following:
1. The rapid unfolding of the product was visualized by endoscope <5 min after administration. See FIG. 44 which shows the GRDF in an unfolded configuration at t=5 min positioned within the pig stomach.
2. The insert eroded gradually from T=0 to 24 hr while the outer portion of the GRDF was maintained.
3. The endoscope pictures provided in FIGS. 44 and 45 exemplified that no significant visualized deformation of the GRDF occurred.
4. The integrity of the stomach tissue was explored by the veterinarian during each endoscope imaging. The vet-erinarian concluded that no tissue damage was observed. Animal behavior, food consumption as well as feces were found normal.

f. Experiment 5—Dog Study in Beagle

The goal of the study was to evaluate the performance of the GRDF in a dog, such as a beagle. The following were evaluated:
1. GRDF opening in the stomach
2. Gastric retention of the GRDF
3. Safety (visual observation of feces, and dog behavior)

Two GRDF samples were chosen having two different release profiles in vitro (see below) by modifying the surface area of the mold holes, as seen in FIGS. 48-51.

a. Sample GRDF Preparation

Figure 46:
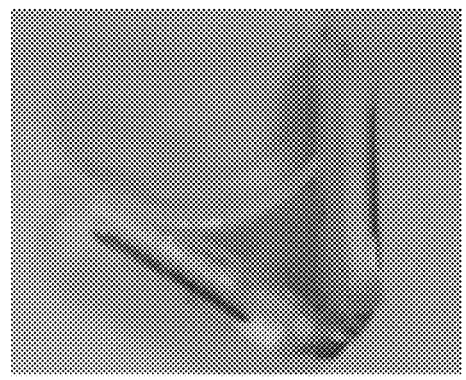
FIG. 46 is a photograph of a GRDF having radio opaque threads (shown in black) attached thereto.

The two GRDFs were prepared as described in Example 4 with a few modifications.
1. Holes were made in each arm by manual drill.
   a. Sample A—4 holes of 1 mm
   b. Sample B—10 holes of 1.2 mm—[SS]—TABLE 13 says 10 holes
2. A radio-opaque thread was attached to each arm by filing a small cut in mold and gluing the thread with a glue made of 3% cellulose acetate in acetone and left to dry for 10 minutes. FIG. 46 depicts a GRDF having radio opaque threads attached thereto (Shown in photo as black lines).

b. In Vitro Dissolution and Test Results

TABLE 13

| | % erosion - visual observation' | | | | | | | erosion rate (%/hr) | Disassembly hr |
|---|---|---|---|---|---|---|---|---|---|
| batch | 0 | 3.5 | 8 | 10 | 12 | 22 | 40 | | |
| Sample A- 1 mm holes × 4 | 0% | 25% | 45% | 55% | 60% | 93% | 100% | 4.1% | 8-12 hr |
| Sample B - 1.2 mm holes × 10 | 0% | 30% | 65% | 80% | 100% | 100% | 100% | 8.2% | 16-20 hr |

Figure 47:
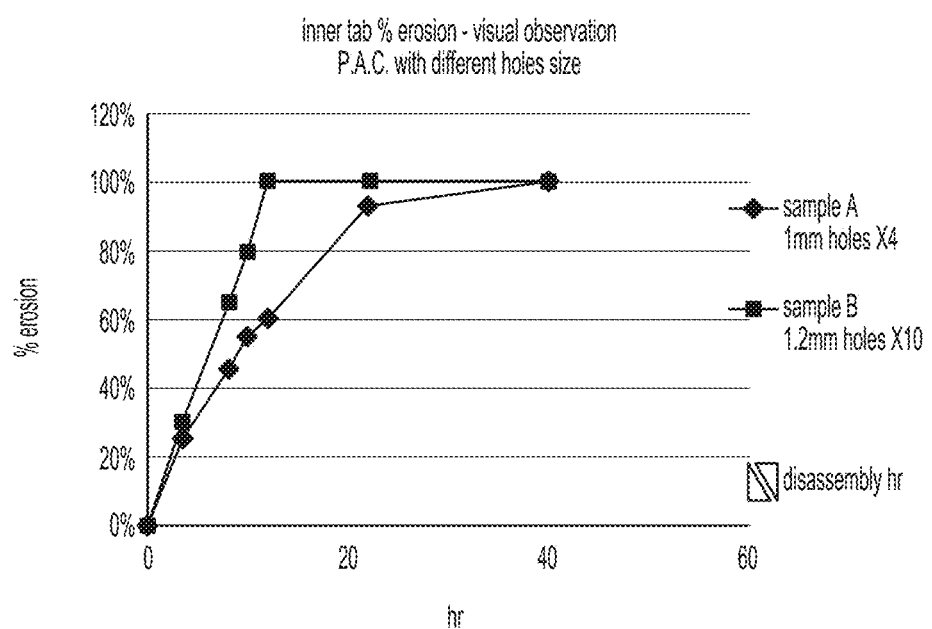
FIG. 47 is a graphical illustration of the percentage of erosion over time of the insert including the API.
Figure 48:
FIGS. 48-51 are X-rays illustrating the gastric retention of the GRDF and the barium impregnated polyethylene spheres (BIPS) at 4 hr, 8 hr, 12 hr, and 24 hr intervals, respectively.
Figure 49:
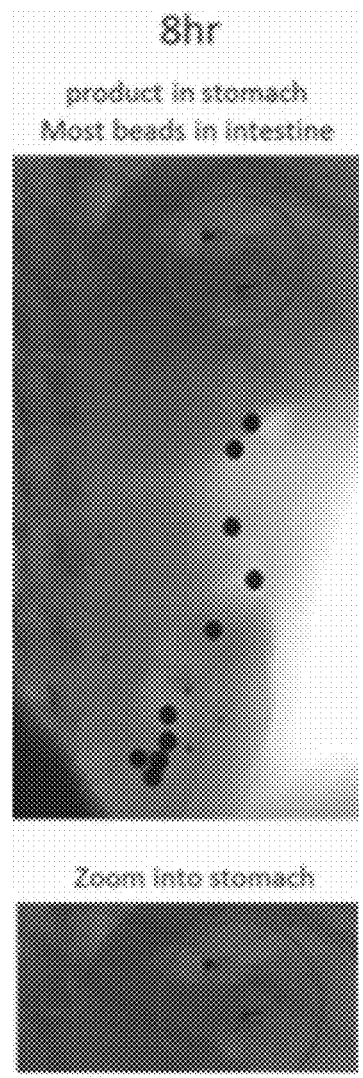
Figure 50:
Figure 51:
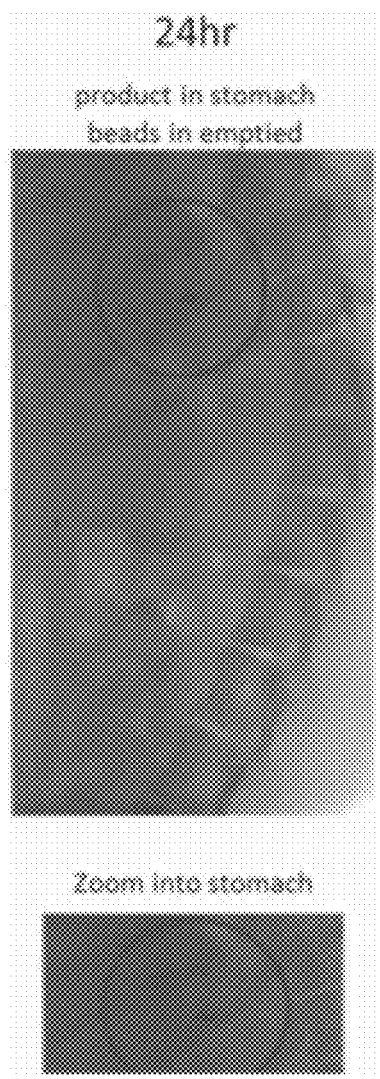

The assembled GRDF dissolution was tested under simulated gastric conditions 5 RPM Rotating apparatus having 37° C., Xanthan gum [0.125 gr/L pH2] with 25 RPM mixing At each interval, the sample GRDF was extracted and the erosion of the insert was visually estimated. The state of disassembly of the GRDF was also evaluated. Work was done in duplicates for each of the samples. The results are described in Table 13 and shown in FIGS. 46 and 47. Disassembly occurred when less than 20% of the insert remained. Sample A which had a reduced surface area of insert exposure displayed a slower release profile than Sample B.

c. Imaging Study

Beagle dogs (9-10 kg weight, age 6 months) were fasted for 12 hrs prior to and after the administering of the GRDF.

Six (6) dogs received Sample A with 5 mm barium impregnated polyethylene spheres (BIPS) meant as a control to observe gastric emptying rate and the intestinal transit time of food. Three (3) dogs received Sample B with control.

The samples were administered utilizing endoscopic device directly into the stomach of lightly anesthetized dogs after administration of pre-warmed water 75-100 cc water. The dogs were fed a 300 gr meal at 12 hours post dose administration. The dosing was repeated in a cross over manner.

The gastric retention was evaluated by Siemens fluoroscopic x-ray imaging that visualized the exact placement of the radiopaque labeled test article and the BIPS, performed at several times. FIGS. 48 to 51 illustrate the gastric retention of the GRDF and the BIPS at 4 hr, 8 hr, 12 hr, and 24 hr intervals, respectively. Animal behavior and feces texture were recorded.

In all dogs, the GRDF expanded in the stomach. The percentage of dogs exhibiting gastric retention is provided in Table 14 below. Note that adjusting the dissolution profile of insert results in the extent of gastric retention.

TABLE 14

| Sample | # of dogs | % of dogs exhibiting gastric retention of GRDF | | | | | | |
|---|---|---|---|---|---|---|---|---|
| | | 4 hr | 8 hr | 12 hr | 16 hr | 24 hr | 30 hr | 40 hr |
| beads | 7 | 100% | 17% | 0% | 0% | 0% | 0% | 0% |
| Sample A | 6 | 100% | 50% | 50% | 50% | 50% | 50% | 0% |
| Sample B | 3 | 100% | 66% | 0% | 0% | 0% | 0% | 0% |

As seen in FIG. 48-51 and Table 14 above, the emptying of the control, i.e., beads, was complete after about 8 hr while Sample A remained in the dog stomach for at least 24 hrs.

Figure 53A:
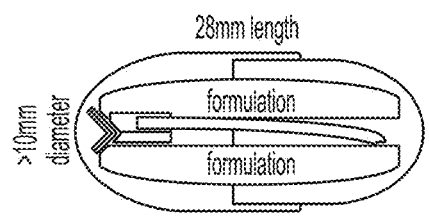
FIG. 53A-53D depict schematic illustrations of an ingestion through disassembly cycle of any one of the GRDFs of the present disclosure.
Figure 53B:
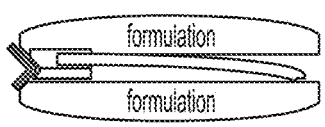
Figure 53C:
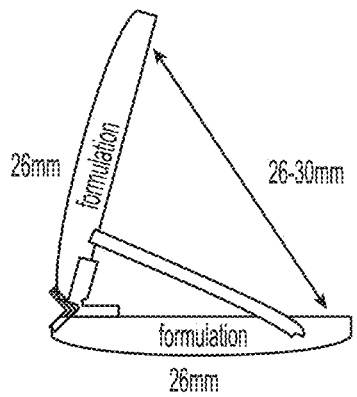
Figure 53D:
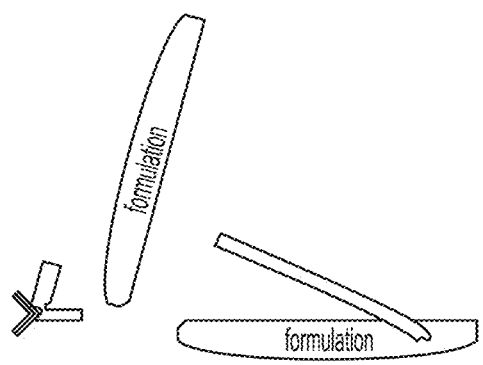

FIGS. 53A-53D show ingestion through disassembly schematic illustrations of a GRDF according to any of the embodiments described herein. During a first stage as shown in FIG. 53A, the GRDF is encapsulated within a retentions mechanism, e.g., capsule 20. After ingestion and after a period of about 1 minute to about 10 minutes, the retention mechanism dissolves allowing the GRDF to expand from a collapsed configuration (FIG. 53B) to an expanded configuration (FIG. 53C) which prevents the GRDF from passing through the pyloric valve of the stomach. In embodiment, the smallest length of the arms and the distance between the tips of the arms to sustain retention is about 26 mm. Over a next predetermined period of time API or diagnostic is released in any of the manners described herein. After a predetermined period of time (as described herein) or upon a sufficient amount of API being released (as described herein) or upon the occurrence of a mechanical event (as described herein), the GRDF disassembles for passage through the pyloric valve.

What is claimed:

1. A gastroretentive dosage form (GRDF) for extended retention in a stomach comprising a body made from a pharmaceutically acceptable material, comprising at least two arms and an active pharmaceutical ingredient (API) or diagnostic, and configured to transform between a collapsed configuration for ingestion, an expanded configuration for retention within the stomach for a predetermined time period, and a third configuration wherein the GRDF disassembles such that each of the disassembled parts of the GRDF is sized for exiting the stomach and wherein at least one of the at least two arms is configured to disassemble as an individual part from the body for exiting the stomach at a pH higher than about 5, wherein in the expanded configuration, the at least two arms and the body each have a center axis, all center axes lying in a single plane, and the at least two arms define an interior angle between adjacent arms from about 45 degrees to about 90 degrees.

2. The GRDF of claim 1, wherein the detachment of at least one of the at least two arms from the body for exiting the stomach is due to erosion of a pH sensitive material at a pH higher than about 5.

3. The GRDF of claim 2, wherein the pH sensitive material erodes at a pH of no more than about 7.5.

4. The GRDF of claim 2, wherein the pH sensitive material erodes in a basic environment.

5. The GRDF of claim 2, wherein the pH sensitive material comprises a polymer.

6. The GRDF of claim 2, wherein the pH sensitive material comprises a polyacrylamide, an acid phthalate of carbohydrate, an amylase acetate phthalate, a cellulose acetate phthalate, a hydroxypropyl cellulose phthalate, a hydroxypropyl ethylcellulose phthalate, a hydroxypropyl methyl cellulose phthalate, a methyl cellulose phthalate, a polyvinyl acetate phthalate, a polyvinyl acetate hydrogen phthalate, a sodium cellulose acetate phthalate, a starch acid phthalate, a styrene-maleic acid dibutyl phthalate copolymer, a styrene-maleic acid polyvinyl acetate phthalate copolymer, a styrene and maleic acid copolymer, a formalized gelatin, gluten, shellac, salol, keratin, a keratin sandaractolu, ammoniated shellac, benzophenyl salicylate, cellulose acetate trimellitate, a cellulose acetate blended with shellac, hydroxypropylmethyl cellulose acetate succinate, oxidized cellulose, a polyacrylic acid derivative, acrylic acid, an acrylic ester copolymer, methacrylic acid or an ester thereof, vinyl acetate, or a crotonic acid copolymer.

7. The GRDF of claim 2, wherein the pH sensitive material represents less than 20% of the total weight of the body of the GRDF.

8. The GRDF of claim 7, wherein the pH sensitive material represents less than 10% of the total weight of the body of the GRDF.

9. The GRDF of claim 2, wherein the erosion of the pH sensitive material results in a partial degradation of at least one of the at least two arms and/or body.

10. The GRDF of claim 2, wherein the body transitions from the collapsed configuration to the expanded configuration upon contact with gastric fluid in the stomach for less than 5 minutes.

11. The GRDF of claim 2, wherein the predetermined time period is 18 hours to 180 days.

12. The GRDF of claim 2, configured for the controlled release of the API in the stomach over a period of 24 hours to 180 days.

13. A gastroretentive dosage form (GRDF) for extended retention in a stomach comprising a body made from a pharmaceutically acceptable material, comprising at least two arms and an active pharmaceutical ingredient (API) or diagnostic, and configured to transform between a collapsed configuration for ingestion, an expanded configuration for retention within the stomach for a predetermined time period, and a third configuration wherein the GRDF disassembles such that each of the disassembled parts of the GRDF is sized for exiting the stomach and wherein at least one of the at least two arms is configured to disassemble as an individual part from the body for exiting the stomach at a pH higher than about 5, wherein in the expanded configuration, the at least two arms and the body each have a center axis, all center axes lying in a single plane, and the at least two arms define an interior angle of between about 45 degrees and about 90 degrees.

14. A method of treating a patient with an API or diagnostic comprising orally administering to the patient the GRDF of claim 1.

15. The method of claim 14, further comprising orally administering an antidote to the patient, wherein the antidote increases the pH of the patient's stomach to higher than 5 so as to achieve erosion of the pH sensitive material and wherein the erosion of the pH sensitive material results in the disassembly and exiting from the stomach of pieces of sufficient size to evacuate the stomach.

* * * * *